United States Patent [19]

Shenvi et al.

[11] Patent Number: 5,654,299
[45] Date of Patent: Aug. 5, 1997

[54] ARYL SUBSTITUTED HETEROCYCLES

[75] Inventors: Ashokkumar Bhikkappa Shenvi; Robert Toms Jacobs, both of Wilmington, Del.

[73] Assignee: Zeneca Limited, London, England

[21] Appl. No.: 228,822

[22] Filed: Apr. 18, 1994

[30] Foreign Application Priority Data

May 24, 1993 [GB] United Kingdom .................. 9310713

[51] Int. Cl.$^6$ .................. A61K 31/445; A61K 31/54; C07D 211/06; C07D 273/04
[52] U.S. Cl. .................. 514/222.5; 514/227.8; 514/231.5; 514/255; 514/278; 514/316; 514/317; 514/318; 514/319; 514/320; 514/321; 514/326; 514/327; 514/329; 514/330; 546/16; 546/17; 546/186; 546/187; 546/188; 546/190; 546/192; 546/194; 546/195; 546/196; 546/198; 546/201; 546/205; 546/206; 546/207; 546/208; 546/213; 546/214; 546/216; 546/217; 546/223; 544/60; 544/66; 544/129; 544/244; 544/360
[58] Field of Search .................. 546/193, 205, 546/217, 223, 16, 17, 186, 187, 188, 190, 192, 194, 195, 196, 198, 201, 206, 207, 208, 213, 214, 216; 514/318, 327, 329, 222.5, 227.8, 231.5, 255, 278, 316, 317, 319, 330; 544/60, 66, 129, 224, 360

[56] References Cited

U.S. PATENT DOCUMENTS

| | | | |
|---|---|---|---|
| 2,891,066 | 6/1959 | Parcell et al. | 260/294.3 |
| 5,236,921 | 8/1993 | Emonds-Alt et al. | 514/252 |
| 5,300,648 | 4/1994 | Emonds-Alt et al. | 546/193 |
| 5,340,822 | 8/1994 | Emonds-Alt et al. | 514/316 |
| 5,411,971 | 5/1995 | Emonds-Alt et al. | 514/318 |

FOREIGN PATENT DOCUMENTS

| | | |
|---|---|---|
| 2029275 | 5/1991 | Canada . |
| 2067924 | 11/1992 | Canada . |
| 2090785 | 9/1993 | Canada . |
| 0428434 | 5/1991 | European Pat. Off. . |
| 0474561 | 3/1992 | European Pat. Off. . |
| 0512901 | 11/1992 | European Pat. Off. . |
| 0512902 | 11/1992 | European Pat. Off. . |
| 0515240 | 11/1992 | European Pat. Off. . |
| 0559538 | 9/1993 | European Pat. Off. . |
| 923178 | 1/1993 | South Africa . |
| 923177 | 3/1993 | South Africa . |
| WO94/10146 | 5/1994 | WIPO . |

OTHER PUBLICATIONS

A. Graham et al., "Isolation and Characterisation of the Human Lung NK-2 Receptor Gene Using Rapid Amplification of cDNA Ends", *Biochemical and Biophysical Research Communications*, (1991), vol. 177, No. 1, 8–16.

X. Emonds–Alt et al., "Pharmacological Profile and Chemical Synthesis of SR 48968, a Non–Peptide Antagonist of the Neurokinin A (NK$_{2-}$) Receptor", *Biorganic & Medicinal Chemistry Letters*, (1993), vol. 3, No. 5, 925–930.

D. Aharony et al., "Pharmacologic Characterization of the Novel Ligand [4,5-$^3$H-LEU$^9$]Neurokinin-A Binding to NK-2 Receptors on Hamster Urinary Bladder Membranes", *Neuropeptides*, (1992), 23, 121–130.

M. Needham et al., "LCR/MEL: A Versatile System for High–Level Expression of Heterologous Proteins in Erythroid Cells", *Nucleic Acids Research*, (1992), vol. 20, No. 5, 997–1003.

G. Lunn, "Preparation of Piperdinylpyridines via Selective Reduction of Bipyridines with Nickel–Aluminum Alloy" *Journal of Organic Chemistry* (Nov. 1992), vol. 57, No. 6, 6317–6320.

*Primary Examiner*—C. Warren Ivy
*Assistant Examiner*—Raymond Covington
*Attorney, Agent, or Firm*—Robert J. Harris

[57] ABSTRACT

The present invention concerns the novel use of aryl substituted heterocycles of formula I, set out below, which antagonize the pharmacological actions of one of ent endogenous neuropeptide tachykinins an the neurokinin 2 (NK2) receptor making them useful whenever such antagonism is desired, such as in the treatment of asthma and related conditions. The invention also provides pharmaceutical compositions containing the aryl substituted heterocycles for use in such treatment. Certain novel aryl substituted heterocycles of formula I and novel intermediates for their manufacture are also provided.

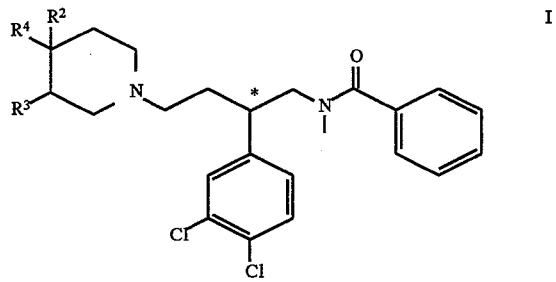

36 Claims, 3 Drawing Sheets

ARYL SUBSTITUTED HETEROCYCLES

This invention concerns novel aryl substituted heterocycles, and, more particularly, novel 1-substituted 4-aryl piperidines which antagonize the pharmacological actions of one or more of the endogenous neuropeptide tachykinins known as neurokinins, particularly at the neurokinin 2 (NK2) receptor. The novel aryl substituted heterocycles are useful whenever such antagonism is desired. Thus, such compounds may be of value in the treatment of those diseases in which an NK2 receptor is implicated, for example, in the treatment of asthma and related conditions. The invention also provides pharmaceutical compositions containing the novel aryl substituted heterocycles for use in such treatment, methods for their use, and processes and intermediates for the manufacture of the novel aryl substituted heterocycles.

The mammalian neurokinins comprise a class of peptide neurotransmitters which are found in the peripheral and central nervous systems. The three principal neurokinins are Substance P (SP), Neurokinin A (NKA), and Neurokinin B (NKB). There are also N-terminally extended forms of at least NKA. At least three known receptor types are known for the three neurokinins. Based upon their relative selectivities favoring the neurokinin agonists SP, NKA and NKB, respectively, the receptors are classified as neurokinin 1 (NK1), neurokinin 2 (NK2) and neurokinin 3 (NK3) receptors, respectively. In the periphery, SP and NKA are localized in C-afferent sensory neurons, which are characterized by non-myelinated nerve endings known as C-fibers, and are released by selective depolarization of these neurons, or selective stimulation of the C-fibers. C-Fibers are located in the airway epithelium, and the tachykinins are known to cause profound effects which clearly parallel many of the symptoms observed in asthmatics. The effects of release or introduction of tachykinins in mammalian airways include bronchoconstriction, increased microvascular permeability, vasodilation and activation of mast cells. Thus, the tachykinins are implicated in the pathophysiology and the airway hyperresponsiveness observed in asthmatics; and blockade of the action of released tachykinins may be useful in the treatment of asthma and related conditions. Peptidic NK2 antagonists have been reported. For example, a cyclic hexapeptide known as L-659,877 has been reported as a selective NK2 antagonist.

Nonpeptidic NK2 antagonists also have been reported; for example, in European Patent Application, Publication Number (EPA) 428434 and EPA 474561 (counterpart U.S. Pat. No. 5,236,921). EPA 428434 discloses a series of 4-substituted piperidino and piperazino derivatives in which the 4-substituent consists of a carbon atom which bears a defined aryl radical and which also may bear a second substituent (selected from hydroxy, oxo and dialkylaminoalkoxyiminio) or be doubly bonded to the 4-carbon of a piperidino radical; the preferred radical (in a specifically claimed compound) is the 4-benzylpiperidino radical. In EPA 474561 (and its counterparts) with a publication date of March 1992, the series of nonpeptidic NK2 antagonists disclosed includes a group of 4,4-disubstituted piperidino derivatives in which [a] the first 4-substituent is selected from a phenyl, pyridyl or thienyl radical, unsubstituted or substituted one or more times with one of the substituents independently selected from hydrogen, halo, hydroxy, (1–4C)alkoxy, trifluoromethyl and (1–4C)alkyl; and [b] the second 4-substituent is selected from a long list of radicals, the radicals hydroxy, acetoxy and (1–6C) alkylcarbonylamino being preferred, or [c] the second substituent forms a double bond with the carbon to which it is linked and with the adjacent carbon atom in the heterocyclic ring. The compound N-[4-(4-acetylamino-4-phenylpiperidino)-2-(3,4-dichlorophenyl)butyl]-N-methylbenzamide (as a racemate or either enantiomer) was identified as particularly preferred in EPA 474561. The (S)-isomer subsequently was identified as the preferred enantiomer and is known as SR 48968, see below. The only exemplification in EPA 474561 of a compound in which the second 4-substituent has the value denoted above as [c] is at Example 41 therein: N-[2-(3,4-dichlorophenyl)-4-[4-(3-trifluoromethylphenyl)-1,2,3,6-tetrahydropyridyl]butyl]-N-methyl-2-thiophenecarboxamide.

We have discovered a series of nonpeptidic NK2 antagonists, which is a series of piperidino derivatives having a different substitution pattern from those disclosed in EPA 428434 and EPA 474561 and this is the basis for our invention. One aspect of the discovery includes monosubstituted piperidino derivatives in which the only 4-substituent is an aryl or heteroaryl group (as defined below). For example, we discovered the 4-phenylpiperidino compound disclosed below at Example 1 to be a potent NK2 antagonist in the in vitro screen described below as Test A and in the functional assay described below as Test B. Subsequent to our discovery (but prior to the 24 May 1993 date of UK application 9310713.4 from which priority is claimed for the instant application) further nonpeptidic tachykinin antagonists were disclosed in EPA 512901, EPA 512902 and EPA 515240 (with counterparts including the Canadian (CA) applications CA 2,067,877; CA 2,067,834 and CA 2,067,924, respectively, each with the publication date of 4 Nov. 1992). The generic disclosure of EPA 512901 includes a structurally different series of compounds, including 4,4-disubstituted piperidino derivatives in which the first 4-substituent is an aryl group defined as noted above under [a] for EPA 474561, and the second 4-substituent is defined as noted above under [b] and [c] for EPA 474561. In addition, EPA 512901 generically discloses monosubstituted 4-arylpiperidino derivatives in which the 4-aryl substituent is defined as noted above under [a] for EPA 474561; however, there is no exemplification of such a compound in EPA 512901. The only examples bearing a single substituent at the 4-position of a piperidino group are 4-benzylpiperidino compounds (the preferred radical in EPA 428434) in which the aryl group is separated from the piperidino ring. The only examples in EPA 512901 bearing an aryl (phenyl) substituent at the 4-position of a piperidino radical also bear a second substituent (hydroxy, acetoxy, acetylamino, as preferred in EPA 474561) at the 4-position, as well. EPA 515240 discloses a further series of compounds structurally related to those of EPA 428434, including 4-substituted piperidino derivatives in which the piperidino 4-substituent is a heteroatom (or substituted heteroatom) further bearing an aryl group.

In a publication closely related to the subject matter of EPA 474561, pharmacological profiles of SR 48968 and other structurally related compounds were disclosed in Edmonds-Alt, X. et al., *Bioorganic and Medicinal Chemistry Letters* (1993), 3(5), 925–930 [hereinafter "Edmonds-Alt (1993)"] with a publication date of 19 Apr. 1993. In Edmonds-Alt (1993), SR 48968 is reported as an NK2 antagonist with an inhibition constant ($K_i$) of 0.5 nM with respect to [$^{125}$I]-NKA binding to its receptor from rat duodenum membranes in an in vitro binding screen similar to that described below as Test A (which employs [$^3$H]-NKA and a recombinant human NK2 receptor). Edmonds-Alt (1993) also discloses the 4-phenylpiperidino species described hereinbelow at Example 1 and reports it to have a $K_i$ in excess of 100 nM. Subsequent to the 24 May 1993 priority date claimed for the instant application, among the compounds generically disclosed, additional 4-arylpiperidino derivatives were disclosed in EPA 559538 (and counterparts including CA 2090785 with a September 1993 publication date, and an earlier Hungarian counterpart HU 9300580, published 28 May 1993). The 4-arylpiperidino compounds included in EPA 559538 are disclosed and claimed generically as being intermediates for preparation of the corresponding compounds in which the nitrogen of the piperidino group is quaternized; the value [d] defined for the "4-aryl" radical is selected from a phenyl radical (which is unsubstituted or substituted one or more times with a substituent independently selected from hydrogen, halo, hydroxy, (1–3C)alkoxy, (1–3C)alkyl, and trifluoromethyl), a (3–7C)cycloalkyl radical, a pyridyl radical or a thienyl radical; only 4-phenylpiperidino is exemplified. Also, EPA 559538 discloses such 4-arylpiperidino compounds, and particularly the 4-phenylpiperidino compounds, as potent antagonists of Substance P at its receptor. In contrast to the lack of biological activity reported in Edmonds-Alt (1993) for the benzamide disclosed herein as Example 1, EPA 559538 discloses the substituted phenylacetamide, N-[2-(3, 4-dichlorophenyl)-4-(4-phenylpiperidino)butyl]-N-methyl-3-isopropoxyphenylacetamide as having a high affinity for neurokinin receptors, but does not disclose such activity for the benzamide, substituted benzamide or 4-fluoro-1-naphthoylamide derivatives exemplified therein, except as antagonists of Substance P. In none of the above mentioned disclosures is there exemplification of a (saturated) piperidino radical which is mono-substituted at the 4-position by a substituted phenyl group or by a heteroaryl group.

According to one feature of the invention, there is provided a method for the treatment of a disease in which NKA is implicated and antagonism of its action is desired, such as, for example, the treatment of asthma or a related disorder, comprising administering to a human or other mammal in need thereof an effective amount of a Compound of the invention which is a compound of formula I (formula set out hereinbelow following the Examples, together with other formulae denoted by Roman numerals) wherein $R^2$ and $R^3$ are each hydrogen or $R^2$ is hydrogen and $R^3$ is hydroxy; and $R^4$ is aryl or heteroaryl which may bear an aryl, aroyl, heteroaryl or heteroaroyl substituent and in which an aromatic or heteroaromatic portion may bear one or more subsitutents on carbon independently selected from halo, cyano, trifluoromethyl, nitro, hydroxy, (1–5C)alkoxy, (1–5C)alkanoyloxy, $NR^AR^B$, $NR^CR^D$, $C(=NR^G)NR^ER^F$, $COOR^K$, $CONR^LR^M$, mercapto, $S(O)_nR^N$, (1–5C)alkyl and (1–5C)alkanoyl wherein $NR^AR^B$ contains zero to about seven carbon atoms and each of $R^A$ and $R^B$ is independently hydrogen, (1–5C)alkyl or (3–6C)cycloalkyl, or $NR^AR^B$ forms a pyrrolidino, piperidino, morpholino, thiomorpholino (or its S-oxide) or piperazinyl group (which piperazinyl group may bear a methyl or ethyl group at the 4-position) any of which cyclic groups may further bear one or more methyl substituents; and wherein $R^C$ is hydrogen or (1–5C)alkyl and $R^D$ is (1–5C)alkanoyl, aroyl or heteroaroyl; or $R^D$ is a group of formula $C(=J)NR^ER^F$ in which J is oxygen, sulfur, $NR^G$ or $CHR^H$; and wherein $NR^ER^F$ contains zero to about seven carbon atoms and each of $R^E$ and $R^F$ is independently hydrogen, (1–5C)alkyl or (3–6C) cycloalkyl, or $NR^ER^F$ forms a pyrrolidino, piperidino, morpholino, thiomorpholino (or its S-oxide) or piperazinyl group (which piperazinyl group may bear a methyl or ethyl group at the 4-position) any of which cyclic groups may further bear one or more methyl substituents; or $R^E$ is hydrogen or (1–5C)alkyl, and $R^F$ together with $R^G$ forms an ethylene or trimethylene group; $R^G$ is hydrogen, (1–5C) alkyl or together with $R^F$ forms an ethylene or trimethylene group; $R^H$ is cyano, nitro or $SO_2R^J$ in which $R^J$ is (1–5C) alkyl or phenyl; $R^K$ is hydrogen, (1–5C)alkyl, aryl, heteroaryl, arylmethyl or heteroarylmethyl; $NR^LR^M$ contains zero to about seven carbon atoms and each of $R^L$ and $R^M$ is independently hydrogen, (1–5C)alkyl or (3–6C) cycloalkyl, or $NR^LR^M$ forms a pyrrolidino, piperidino, morpholino, thiomorpholino (or its S-oxide) or piperazinyl group (which piperazinyl group may bear a methyl or ethyl group at the 4-position) any of which cyclic groups may further bear one or more methyl substituents; $R^N$ is (1–6C) alkyl, (3–6C)cycloalkyl, aryl or heteroaryl, and n is the integer 0, 1 or 2; and wherein a heteroaromatic nitrogen may bear a (1–5C)alkyl substituent; and further wherein a (1–5C) alkyl, (1–5C)alkoxy or (1–5C)alkanoyl substituent or portion of $R^4$ may bear a hydroxy, a (1–3C)alkoxy or one or more halo substituents provided that a carbon bound to nitrogen or oxygen does not bear a hydroxy or alkoxy substituent and that the α-carbon of an alkanoyl group does not bear a chloro, bromo or iodo substituent;

or $R^3$ is hydrogen and $R^2$ and $R^4$ together with a diradical $X^1$ and the piperidino 4-carbon to which they are attached form a spirocyclic ring wherein $R^4$ is phenyl which is joined to $R^2$ by an ortho-substituent diradical $X^1$ in which the phenyl $R^4$ may bear a further substituent selected from halo, (1–3C)alkyl, (1–3C)alkoxy, hydroxy, (1–3C)alkylthio, (1–3C)alkylsulfinyl and (1–3C)alkylsulfonyl; the diradical $X^1$ is methylene, carbonyl or sulfonyl; and $R^2$ is oxy or imino of formula —$NR^Q$— in which $R^Q$ is hydrogen or (1–3C)alkyl;

or a pharmaceutically acceptable salt thereof.

Thus, the present invention also provides a compound of formula I as defined above, or a pharmaceutically acceptable salt thereof, for use in medicine; and in particular for use in the treatment of a disease in which NKA is implicated and antagonism of its action is desired, such as, for example, the treatment of asthma or a related disorder.

According to another feature of the invention, there is provided a pharmaceutical composition comprising a compound of formula I as defined above, or a pharmaceutically acceptable salt thereof, and a pharmaceutically acceptable diluent or carrier.

A further feature of the invention is provided by a novel compound of formula I as defined above, or a pharmaceutically acceptable salt thereof. As noted above, Edmonds-Alt (1993) also discloses the 4-phenylpiperidino species described hereinbelow at Example 1 and reports it to have a $K_i$ in excess of 100 nM; and later published patent applications generically disclose and claim certain 4-arylpiperidino compounds as synthetic intermediates, with exemplification of the 4-phenylpiperidino species described hereinbelow at Example 1.

A particular compound of formula I is one in which $R^2$ and $R^3$ are each hydrogen; and $R^4$ is aryl or heteroaryl which may bear an aryl, aroyl, heteroaryl or heteroaroyl substituent and in which an aromatic or heteroaromatic portion may bear one or more subsitutents on carbon independently selected from halo, cyano, trifluoromethyl, nitro, hydroxy, (1–5C)alkoxy, (1–5C)alkanoyloxy, $NR^AR^B$, $NR^CR^D$, $C(=NRG)NR^ER^F$, $COOR^K$, $CONR^LR^M$, $S(O)_nR^N$, (1–5C)alkyl and (1–5C) alkanoyl wherein $NR^AR^B$ contains zero to about seven carbon atoms and each of $R^A$ and $R^B$ is independently hydrogen, (1–5C)alkyl or (3–6C)cycloalkyl, or $NR^AR^B$ forms a pyrrolidino, piperidino, morpholino, thiomorpholino (or its S-oxide) or piperazinyl group (which piperazinyl group may bear a methyl or ethyl group at the 4-position); and wherein $R^C$ is hydrogen or (1–5C)alkyl and $R^D$ is (1–5C)alkanoyl, aroyl or heteroaroyl; or $R^D$ is a group of formula C(=J)NR$^E$R$^F$ in which J is oxygen, sulfur, NR$^G$ or CHR$^H$; and wherein NR$^E$R$^F$ contains zero to about seven carbon atoms and each of $R^E$ and $R^F$ is independently hydrogen, (1–5C)alkyl or (3–6C)cycloalkyl, or NR$^E$R$^F$ forms a pyrrolidino, piperidino, morpholino, thiomorpholino (or its S-oxide) or piperazinyl group (which piperazinyl group may bear a methyl or ethyl group at the 4-position); or $R^E$ is hydrogen or (1–5C)alkyl, and $R^F$ together with $R^G$ forms an ethylene or trimethylene group; $R^G$ is hydrogen, (1–5C)alkyl or together with $R^F$ forms an ethylene or trimethylene group; $R^H$ is cyano, nitro or SO$_2$R$^J$ in which $R^J$ is (1–5C)alkyl or phenyl; $R^K$ is hydrogen, (1–5C)alkyl, arylmethyl or heteroarylmethyl; NR$^L$R$^M$ contains zero to about seven carbon atoms and each of $R^L$ and $R^M$ is independently hydrogen, (1–5C)alkyl or (3–6C)cycloalkyl, or NR$^L$R$^M$ forms a pyrrolidino, piperidino, morpholino, thiomorpholino (or its S-oxide) or piperazinyl group (which piperazinyl group may bear a methyl or ethyl group at the 4-position); $R^N$ is (1–6C)alkyl, (3–6C)cycloalkyl, aryl or heteroaryl, and n is the integer 0, 1 or 2; and wherein a heteroaromatic nitrogen may bear a (1–5C)alkyl substituent; and further wherein a (1–5C)alkyl, (1–5C)alkoxy or (1–5C)alkanoyl substituent or portion of $R^4$ may bear a hydroxy, a (1–3C)alkoxy or one or more halo substituents provided that a carbon bound to nitrogen or oxygen does not bear a hydroxy or alkoxy substituent and that the α-carbon of an alkanoyl group does not bear a chloro, bromo or iodo substituent;

or a pharmaceutically acceptable salt thereof.

It will be appreciated that the compounds of formula I contain one or more asymmetrically substituted carbon atoms such that such compounds may be isolated in optically active, racemic and/or diastereomeric forms. Some compounds may exhibit polymorphism. It is to be understood that the present invention encompasses any racemic, optically-active, diastereomeric, polymorphic or stereoisomeric form, or mixtures thereof, which form possesses NK2 antagonist properties, it being well known in the art how to prepare optically-active forms (for example, by resolution of the racemic form or by synthesis from optically-active starting materials) and how to determine the NK2 antagonist properties by the standard tests described hereinafter. It may be preferred to use the compound of formula I in a form which is characterized as containing, for example, at least 95%, 98% or 99% enantiomeric excess of the form which is of the (S)-configuration at the center indicated by * in formula I.

In this specification $R^A$, $R^B$, $R^4$ et cetera stand for generic radicals and have no other significance. It is to be understood that the generic term "(1–5C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, alkoxy, alkanoyl, et cetera. Halo is fluoro, chloro, bromo or iodo. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms selected from the group consisting of oxygen, sulfur and nitrogen, as well as a radical of an ortho-fused bicyclic heterocycle of about eight to ten ring atoms derived therefrom, particularly a benz-derivative or one derived by fusing a propenylene, trimethylene or tetramethylene diradical thereto, as well as a stable N-oxide thereof. Aroyl and heteroaroyl refer to arylcarbonyl and heteroarylcarbonyl radicals, respectively.

A pharmaceutically acceptable salt is one made with an acid which provides a physiologically acceptable anion.

Particular values are listed below for radicals, substituents and ranges for illustration only and they do not exclude other defined values or other values within defined ranges for the radicals and substituents. Particular values for $R^4$ include, for example, for aryl: phenyl, indenyl or naphthyl; for heteroaryl: furyl, thienyl, pyrrolyl, pyridyl or pyrimidinyl, as well as 1,3,4-oxadiazol-2-yl, 2-imidazolyl, or benz[d]isoxazol-3-yl. Particular values for an optional substituent on an aromatic or heteroaromatic carbon of $R^4$ include, for example, for halo: fluoro or chloro; cyano; trifluoromethyl; hydroxy; for (1–5C)alkoxy: methoxy or ethoxy; for (1–5C)alkanoyloxy: acetoxy, for NR$^A$R$^B$: amino, methylamino or dimethylamino; for NR$^C$R$^D$: acetamido; for C(=NR$^G$)NR$^E$R$^F$: imidazolin-2-yl; for COOR$^K$: carboxy, methoxycarbonyl or benzyloxycarbonyl, as well as ethoxycarbonyl; for CONR$^L$R$^M$: carbamoyl, N,N-dimethylcarbamoyl or pyrrolidinocarbonyl, as well as N-methylcarbamoyl; for S(O)$_n$R$^N$: methylthio, methylsulfinyl or methylsulfonyl; for (1–5C)alkyl: methyl, ethyl, propyl, butyl, isopropyl or 2-methylpropyl, as well as tert-butyl; and for (1–5C)alkanoyl: formyl, acetyl and propionyl. A particular value for a substituent on a heteroaromatic nitrogen of $R^4$ is, for example, methyl or ethyl. A particular value for a substituent on a (1–5C)alkyl, (1–5C)alkoxy or (1–5C)alkanoyl substituent or portion of $R^4$ is, for example, hydroxy, methoxy, ethoxy, chloro, fluoro or trifluoro.

One particular group of compounds of formula I is one in which $R^2$ and $R^3$ are each hydrogen and $R^4$ is, for example, phenyl which may bear a fluoro, chloro, hydroxy, methoxy, acetoxy, amino, acetamido, methoxycarbonyl, carbamoyl, methyl, ethyl or acetyl substituent; and, more particularly, $R^4$ is phenyl which bears a hydroxy substituent.

Another particular group of compounds of formula I is one in which $R^2$ is hydrogen, $R^3$ is hydroxy which is trans-to $R^4$, and $R^4$ is phenyl which may bear a methoxy, hydroxy, methylthio or methylsulfinyl substituent, or a pharmaceutically acceptable salt thereof.

A further particular group of compounds of formula I is one in which $R^3$ is hydrogen and $R^2$ and $R^4$ together with a diradical $X^1$ and the piperidino 4-carbon to which they are attached form a spirocyclic ring wherein $R^4$ is phenyl which is joined to $R^2$ by an ortho-substituent diradical $X^1$ in which the phenyl $R^4$ may bear a further substituent selected from methoxy, hydroxy, methylthio, and methylsulfinyl; the diradical $X^1$ is methylene or carbonyl; and $R^2$ is oxy; or a pharmaceutically acceptable salt thereof.

Further selected aspects of the invention are based upon surprisingly superior results obtained (and disclosed below) upon oral (p.o.) dosing in the in vivo test described below as Test C for selected groups of compounds of formula I.

Accordingly, as a selected aspect of the invention, there is provided a compound of formula I (in either the (RS)- or, preferably, the (S)-form at the center indicated by * in formula I) in which $R^2$ and $R^3$ are each hydrogen and $R^4$ is phenyl which bears a methylthio or methylsulfinyl (as a mixture of optical isomers or as a single isomer) substituent, or a pharmaceutically acceptable salt thereof. As an additional selected aspect of the invention, there is provided a method for the treatment of a disease in which NKA is implicated and antagonism of its action is desired, such as, for example, the treatment of asthma or a related disorder, comprising administering to a human or other mammal in need thereof an effective amount of such a compound of formula I, or a pharmaceutically acceptable salt thereof. As an additional selected aspect of the invention, there is provided a pharmaceutical composition comprising such a compound of formula I as defined above, or a pharmaceutically acceptable salt thereof, and a pharmaceutically acceptable diluent or carrier.

As another selected aspect of the invention, there is provided a compound of formula I (in either the (RS)- or, preferably, the (S)-form at the center indicated by * in formula I) in which $R^2$ and $R^3$ are each hydrogen and $R^4$ is pyridyl (and more particularly, 3-pyridyl), or a pharmaceutically acceptable salt thereof. As an additional selected aspect of the invention, there is provided a method for the treatment of a disease in which NKA is implicated and antagonism of its action is desired, such as, for example, the treatment of asthma or a related disorder, comprising administering to a human or other mammal in need thereof an effective amount of such a compound of formula I, or a pharmaceutically acceptable salt thereof. As an additional selected aspect of the invention, there is provided a pharmaceutical composition comprising such a compound of formula I as defined above, or a pharmaceutically acceptable salt thereof, and a pharmaceutically acceptable diluent or carrier.

Specific compounds of formula I are described in the accompanying Examples; the species named therein (in either the (RS)- or, preferably, the (S)-form at the center indicated by * in formula I), and their pharmaceutically acceptable salts, provide a further aspect of the invention. Of these, the compounds named at Examples 9, 13, 14, 15, 16 and 17 (and particularly at Examples 14, 15 and 16), or a pharmaceutically acceptable salt thereof, are preferred.

Pharmaceutically acceptable salts of a compound of formula I include those made with a strong inorganic or organic acid which affords a physiologically acceptable anion, such as, for example, hydrochloric, sulfuric, phosphoric, methanesulfonic, or para-toluenesulfonic acid.

A compound of formula I may be made by processes which include processes known in the chemical art for the production of structurally analogous heterocyclic compounds. Such processes and intermediates for the manufacture of a compound of formula I as defined above are provided as further features of the invention and are illustrated by the following procedures in which the meanings of generic radicals are as defined above unless otherwise indicated:

(a) Alkylating a corresponding piperidine of formula II with an aldehyde of formula III, by reductive alkylation, or with an alkylating agent of formula IV in which Y is a leaving group. The alkylation is preferably carried out by a conventional reductive alkylation, for example as described in Example 1, by the in situ, acid-catalyzed formation of an imminum salt, followed by reduction with sodium cyanoborohydride in alcoholic solvent. The reductive alkylation may be carried out in a suitable solvent, such as methanol, tetrahydrofuran or acidic water, using a suitable reducing agent, such as for example sodium cyanoborohydride, conveniently at a temperature in the range of −20° to 50° C., preferably in the range of 0° to 25° C. The compound of formula I is conveniently isolated as an acid addition salt, for example the hydrochloride salt.

(b) For a compound of formula I in which $R^2$ and $R^3$ are each hydrogen, hydrogenation of the double bond of a corresponding compound of formula I in which $R^2$ and $R^3$, together with the existing carbon to carbon bond, form a double bond. Conveniently, the hydrogenation is carried out at atmospheric pressure over palladium on carbon catalyst in an acidic solution in a lower alcohol; and the product is conveniently isolated as its acid addition salt, such as its hydrochloride salt, for example as described in Example 1.

It may be desired to optionally use a protecting group during all or portions of the above described processes; the protecting group then may be removed when the final compound is to be formed.

Whereafter, for any of the above procedures, when a pharmaceutically acceptable salt of a compound of formula I is required, it may be obtained by reacting the compound of formula I with an acid affording a physiologically acceptable counterion or by any other conventional procedure.

If not commercially available, the necessary starting materials for the above procedures may be made by procedures which are selected from standard techniques of heterocyclic chemistry, techniques which are analogous to the synthesis of known, structurally similar compounds, and techniques which are analogous to the above described procedures or the procedures described in the Examples. The starting materials and the procedures for their preparation are additional aspects of the invention.

In general, a starting material of formula II may be prepared from 4-piperidone, using a procedure similar to that described in Example 2, by the sequence of protection of the ring nitrogen with a conventional protecting group, such as a benzyloxycarbonyl group; treatment of the resulting piperidone with an organometallic reagent, such a compound of formula $R^4Li$ or $R^4MgBr$; hydrogenolysis of the resulting tertiary alcohol (for example, by the use of trifluoroacetic acid and triethylsilane in an inert solvent such as dichloromethane); and removal of the nitrogen protecting group to afford the piperidine of formula II. Alternatively, it may be preferable to dehydrate the tertiary alcohol, followed by hydrogenation of the resulting double bond. Some compounds of formula II may be made conveniently by palladium catalyzed addition of the heteroaryl group using a procedure similar to that described in Example 9.g.–9.i. For certain compounds in which $R^4$ is heteroaryl, it may be preferred to use a derivative of piperidine-4-carboxylic acid or piperidine-4-carbonitrile as a starting material and to construct the heteroaryl substituent using a conventional procedure, for example as described under Examples 7 and 8. Other transformations to provide required substituents on the group $R^4$ may be carried out when convenient. For example, an alkylthio substituent may be oxidized to a corresponding alkylsulfinyl substituent using a conventional reagent, including a conventional reagent for the chiral oxidation of an alkylthio group to a chiral alkylsulfinyl group. A 4-hydroxy piperidine of formula Va (which may be prepared using an analogous sequence to that described above, but omitting the hydrogenolysis) may be alkylated with a starting material of formula III or IV using a procedure analogous to that described in process (a) to afford a corresponding starting material of formula V, for example as described in Example 1.h.

Certain compounds of formula II (and their synthetic precursors) are believed to be novel and provide an additional aspect of the invention.

An intermediate aldehyde of formula III may be prepared as outlined in Scheme I and described in Example 1, parts a.–g. Alkylation of the anion of 3,4-dichlorophenylacetonitrile with 1-bromo-2-(2-tetrahydropyranyloxy)ethane (conveniently prepared from 2-bromoethanol and dihydropyran using a strong acid exchange resin as catalyst) gives a nitrile of formula VI. Reduction of the nitrile gives a corresponding amine of formula VII which can be acylated using benzoic anhydride in the presence of a suitable base to give an amide of formula VIII. Alkylation of the amide with methyl iodide followed by hydrolysis of the acetal gives an alcohol of formula IX, which can be oxidized to give an intermediate of formula III. Alternatively, the alcohol of formula IX may be converted into an alkylating agent of formula IV using a conventional procedure.

An intermediate of formula III or of formula IV wherein the center marked with * has the (S) absolute configuration can be prepared from a corresponding compound of formula IX which may be obtained from a racemic compound of formula VII as outlined in Scheme II. Hydrolysis of an acetal of formula VII gives an amine of formula X. Salt formation with D-tartaric acid followed by crystallization, recrystallization and treatment with aqueous base gives the (S)-enantiomer of the compound of formula X. Treatment with ethyl chloroformate followed by reduction of the resulting carbamate gives the (S)-enantiomer of the amine of formula XI. Treatment of the amine with benzoyl chloride gives the (S)-enantiomer of the compound of formula IX, which can be oxidized, for example using oxalyl chloride, dimethyl sulfoxide and triethylamine or using Dess-Martin periodinane (1,1,1-triacetoxy-1,1-dihydro-1,2-benziodoxol-3(1H)-one) to give the (S)-enantiomer of the compound of formula III or can be converted into the (S)-enantiomer of the compound of formula IV.

As will be clear to one skilled in the art, a variety of sequences is available for preparation of the starting materials, and the sequences leading to the starting materials and products of the invention may be altered if appropriate considerations regarding the synthetic methods and radicals present are followed.

The utility of a compound of the invention or a pharmaceutically acceptable salt thereof (hereinafter, collectively referred to as a "Compound") may be demonstrated by standard tests and clinical studies, including those disclosed in Edmonds-Alt (1993) and in the EPA publications noted above, such as EPA 428434 or EPA 474561 (or U.S. Pat. No. 5,236,921), and those described below.

Neurokinin A (NKA) Receptor-binding Assay (Test A)

The ability of a Compound of the invention to antagonize the binding of NKA at the NK2 receptor may be demonstrated using an assay using the human NK2 receptor expressed in Mouse Erythroleukemia (MEL) cells by using MEL cell membranes (ELM) which bear high-affinity and selective NK2 receptors and which is carried out as follows.

MEL CELL EXPRESSION OF HUMAN NK2 RECEPTOR (hNK2R)

Figure 1:
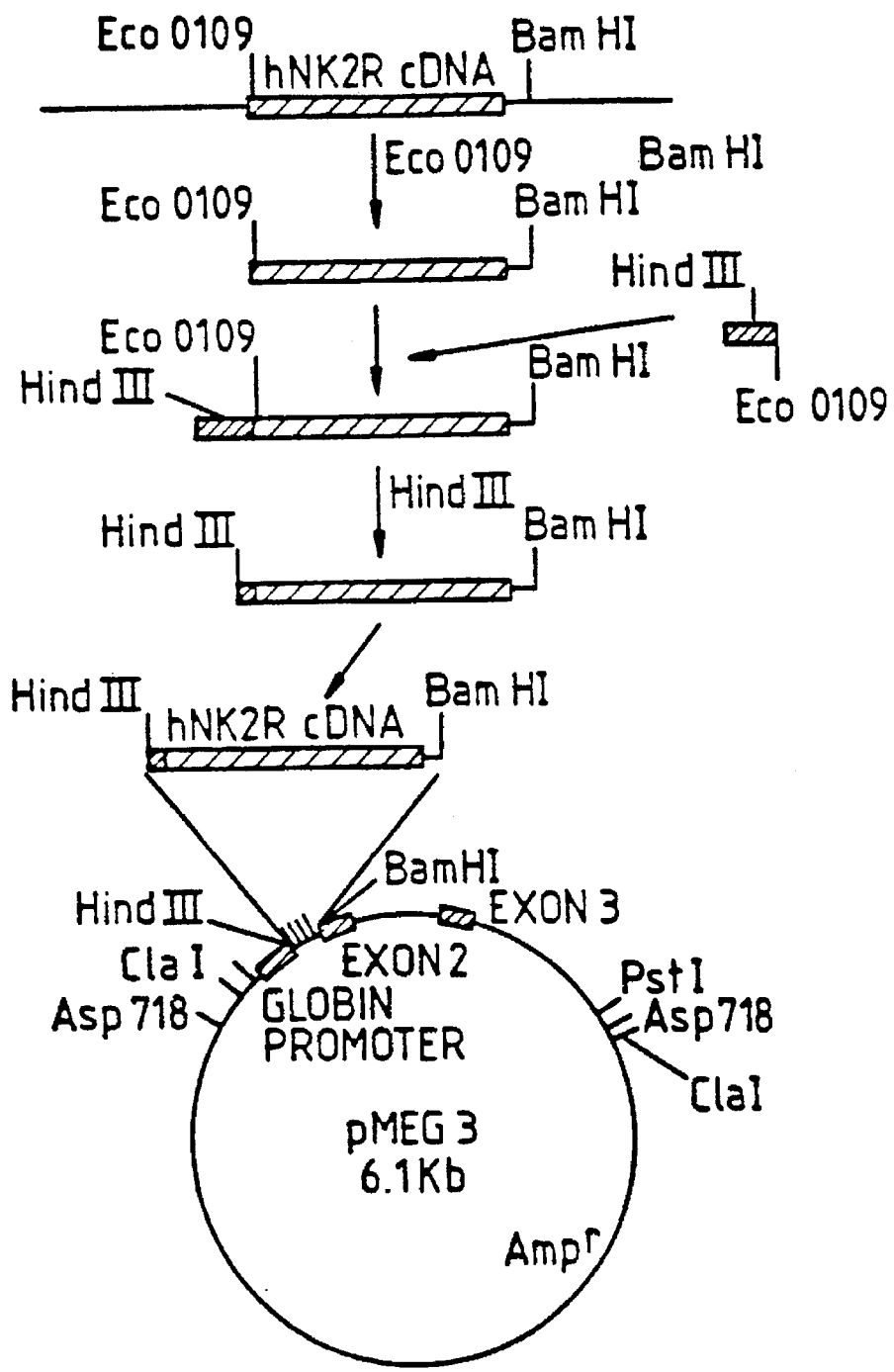
FIG. 1 shows construction of the MEL cell expression vector construct DMEG3/hNK2R.
Figure 2:
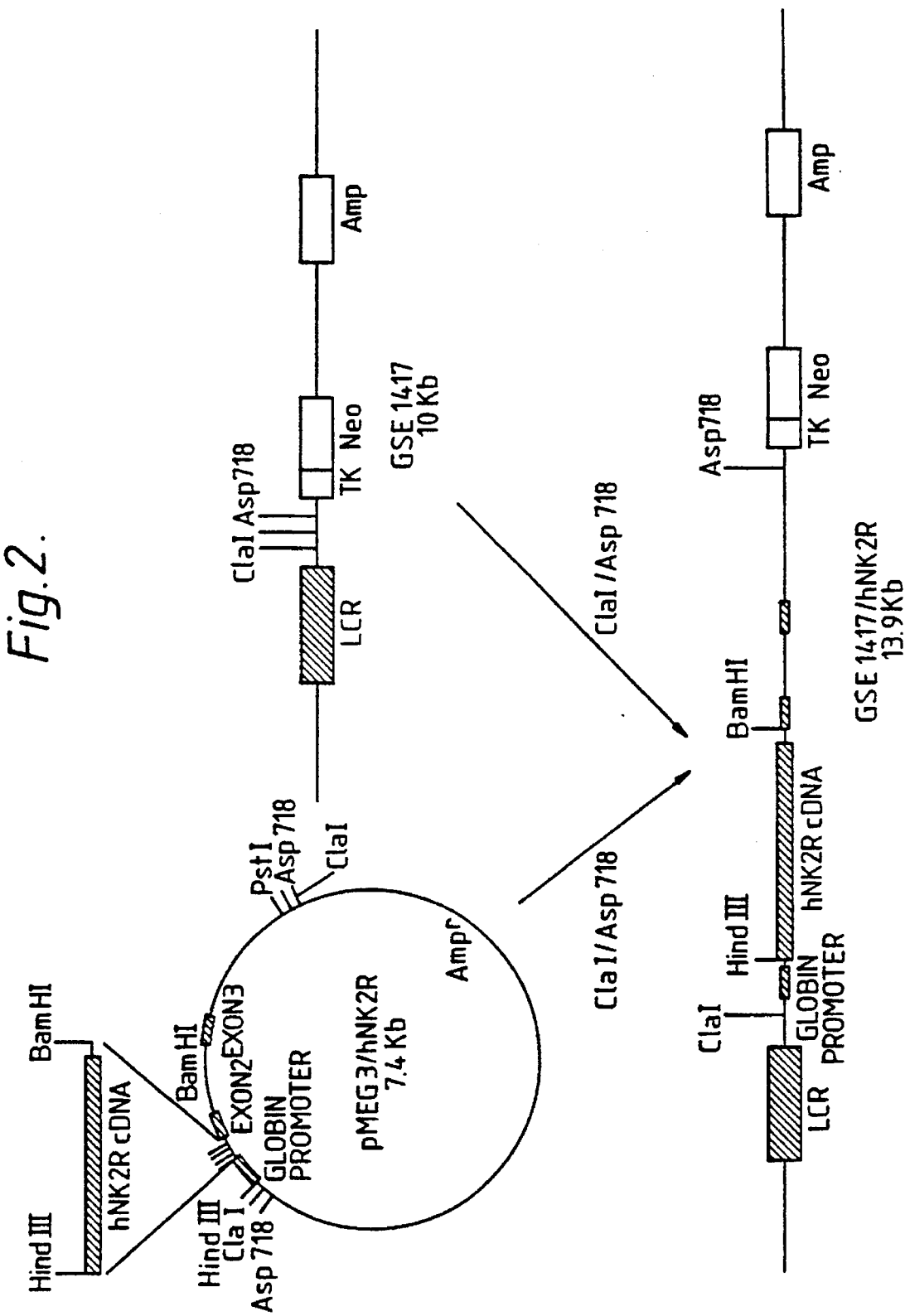
FIG. 2 shows construction of the expression vector construct GSE1417/hNK2R.
Figure 3:
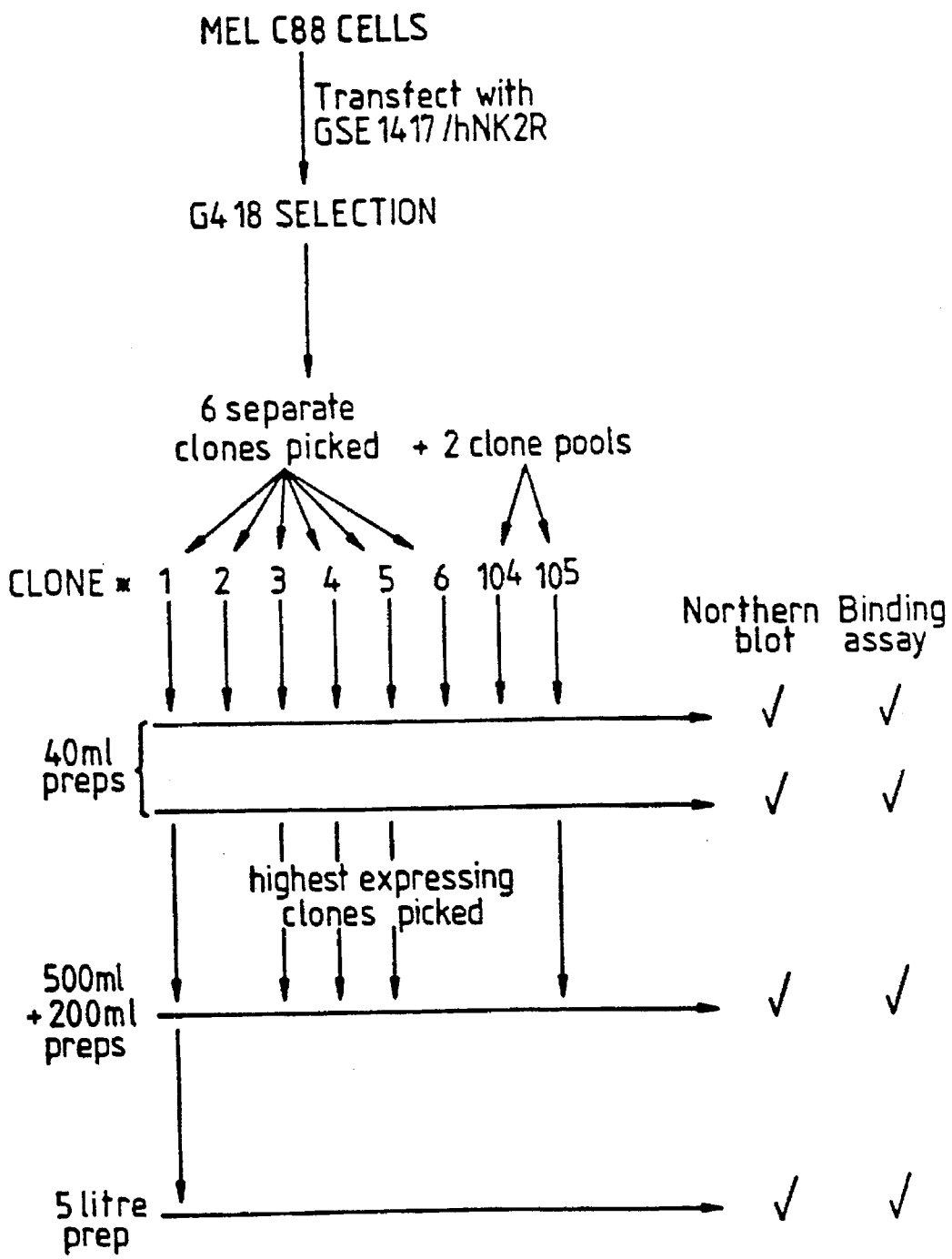
FIG. 3 shows expression of human NK2 receptor in MEL C88 cells.

Heterologous protein expression in Mouse Erythroleukemia (MEL) cells uses the human globin locus control region (LCR) (F. Grosveld et al., Cell (1987) 51, 975–985). The cDNAs are inserted between the human beta-globin promoter and the second intron of the human beta-globin gene, and this expression cassette is then placed downstream of the LCR and transfected into MEL cells (M. Needham et al., Nucl. Acids Res. (1992) 20, 997–1003). Human NK2 receptor cDNA (A. Graham et al., Biochem. Biophys. Res. Commun. (1991) 177, 8–16) was isolated from human lung RNA by polymerase chain reaction and DNA sequenced. Human NK2 receptor cDNA was subcloned into a shuttle vector (pMEG3) containing the beta-globin promoter and the 3' portion of the human beta-globin gene (FIG. 1). Human NK2 receptor cDNA was restricted with Eco 0109 (5' end) and Bam HI (3' end). An oligonucleotide linker-adaptor containing an internal Hind III site and a 3' end Eco 0109 site was ligated to the hNK2R cDNA fragment. The sequence of the top strand oligonucleotide=5'd (GCGCAAGCTTATGGG) (SEQ ID NO:1) and the bottom strand oligonucleotide=5'd (GTCCCCATAAGCTTGCGC) (SEQ ID NO:2). These were annealed and ligated to the hNK2R fragment by standard methods. Following cleavage with Hind III, the resulting fragment was cloned into the Hind III and Bam HI sites in the polylinker of the shuttle vector pMEG3. The construct (pMEG3/hNK2R) was verified by restriction mapping and sequencing the 5' end and 3' end junctions of cDNA/vector. This was then transformed into E. coli DH5 alpha, and plasmid DNA was isolated by standard methods and verified by restriction mapping and DNA sequencing. A ClaI/Asp718 cassette carrying the beta-globin promoter, human NK2 receptor cDNA and the 3' beta-globin gene fragment was excised and subcloned downstream of the LCR in plasmid pGSE1417 (FIG. 2). The pMEG3/hKNK-2R construct was cleaved with ClaI and Asp718 and cloned directly into the ClaI and Asp718 sites (3' of LCR) in the expression vector GSE1417. The construct GSE1417/hNK2R (13.9 kb) was verified by restriction mapping. E. coli DH5 alpha was transformed and recombinant plasmids verified by restriction mapping. MEL C88 cells (A. Deisseroth et al., Cell (1978) 1–5, 55–63) were electroporated (M. Antoniou, Methods Molecular Biology (1991) 7, 421–434) with PvuI linearized pGSE1417/human NK2 receptor DNA. Directly after transfection, cells were diluted in culture medium to $10^4$ and $10^5$ cell per mL and 1 mL aliquots transferred to each well of a 24-well plate. G418 was added to a concentration of 1 mg/mL 24 hours after the transfection to select for stable transfectants. Individual clones were picked or pooled to generate populations seven to ten days after the addition of selective medium. FIG. 3 shows the strategy used to isolate transfected MEL/human NK2 receptor cell line. For expression studies, cells were maintained in exponential growth for a period of four days, and then dimethyl sulfoxide (DMSO) was added to a final concentration of 2% (v/v) to induce differentiation and hence expression. Samples were taken 4 days post induction for mRNA and NKA binding analyses. The results indicated that clone #1 expresses hNK2R at the highest level (both hNK2R mRNA and specific NKA binding). This clone was scaled up and is now routinely fermented at 20 litre scale per month and supplied for use in Test A.

Membrane preparations (MELM) prepared from the MEL cells containing high-affinity NK2 receptors were prepared according to a published protocol (D. Aharony, et al., Neuropeptides (1992) 23, 121–130) with the following minor modifications: (1) Iodoacetamide (1 mM) was included in the homogenization buffer; (2) Homogenization was as published but for a shorter period of 10 seconds once and at a slower speed (setting 10); and (3) The equilibration step with KCl/EDTA was not performed. In a typical preparation, binding of $^3$H-NKA (2.5 nM) to MELM was highly specific (88±4%) and linearly dependent on the protein concentration, with significant binding detected as low as 26 µg protein/mL. Equilibrium-competion experiments demonstrated binding to high-affinity, high-density receptors with $K_D$=1187 nM, $B_{max}$=2229 fmol/mg protein.

The radio ligand $^3$H-neurokinin A ($^3$H-NKA) as [4,5-$^3$H-Leu$^9$]-NKA (typical specific activity, 117 Ci/mmol) is obtained by custom synthesis from Cambridge Research Biochemicals and is >95% pure. Repeated HPLC analysis demonstrated that the ligand is stable under proper storage conditions (silanized vials with 0.2% mercaptoethanol, under argon). Also, no degradation or metabolism is apparent in the receptor-binding assay.

The assay is carried out using an incubation buffer consisting of 50 mM Tris HCl (pH 7.4), 5 mM $Mg^{++}$, 100 µM thiorphan, 1 nM $^3$H-NKA, 0.02% (w:v) BSA, 30 mM $K^+$, and 300 µM dithiothreitol; and the concentration of membrane protein is held at approximately 0.05–0.025 mg per tube. Nonspecific binding is routinely defined with 1 µM NKA. Each tube receives the following: 150 µL incubation buffer, 20 µL $^3$H-NKA, 20 µL Compound, NKA or buffer as appropriate, and 125 µL membrane suspension. The reaction is initiated by the addition of the membranes. The tubes are incubated for 60 min at 25° C. in a shaking water bath. The reaction is terminated by washing the tubes with 10 mL of ice-cold 50 mM Tris HCl using a Brandel cell harvesting system using Whatman GF/B filters which have been soaked at least 4 hours at room temperature in 0.01% (w:v) polyethylenimine to collect the membranes. The filters are deposited in scintillation vials and read in a Beckman LS 6000LL Scintillation Counter. The binding constant $K_i$ is calculated by standard methods and is typically the mean of several such determinations. The $K_i$ values may be converted to negative logarithms and expressed as -log molar K. (i.e. $pK_i$).

In an initial use of this assay, the $IC_{50}$ measured for the standard compound L-659,877 was found to be 30 nM versus $^3$H-NKA binding to MELM. The selectivity of a Compound for binding at the NK2 receptor may be shown by determining its binding at other receptors using standard assays, for example, one using a tritiated derivative of SP in a tissue preparation selective for NK1 receptors or one using a tritiated derivative of NKB in a tissue preparation selective for NK3 receptors.

Guinea Pig Trachea Assay (Test B)

In the test described below either NKA or [β-ala$^8$]-NKA (4–10) is used as an agonist. The chosen agonist is referred to as AG throughout the description. The ability of a Compound of the invention to antagonize the action of AG in a pulmonary tissue maybe demonstrated using a functional assay in guinea pig trachea, which is carried out as follows.

Male guinea pigs are killed by a sharp blow to the back of the head. The trachea are removed, trimmed of excess tissue and divided into two segments. Each segment is suspended as a ring between stainless steel stirrups in water-jacketed (37.5° C.) tissue baths containing a physiological salt solution of the following composition (mM): NaCl, 119; KCl 4.6; $CaCl_2$, 1.8; $MgCl_2$, 0.5; $NaH_2PO_4$, 1; $NaHCO_3$, 25; glucose, 11; thiorphan, 0.001; and indomethacin, 0.005; gassed continuously with 95% $O_2$-%5 $CO_2$. Initial tension placed on each tissue is 1 g, which is maintained throughout a 0.5 to 1.5 hour equilibration period before addition of other drugs. Contractile responses are measured on a Grass polygraph via Grass FT-03 force transducers.

Tissues are challenged repetitively with a single concentration of AG (10 nM) with intervening 30 min periods with washing to allow the tension to return to baseline levels. The magnitude of the contractions to AG reaches a constant level after two challenges, and each Compound is tested for inhibition of responses to AG by addition to the tissue bath 15 minute before the third or subsequent exposure to the agonist. The contractile response to AG in the presence of Compound is compared to that obtained with the second AG challenge (in the absence of Compound). Percent inhibition is determined when a Compound produces a statistically significant (p<0.05) reduction of the contraction and is calculated using the second contractile response as 100%.

Potencies of selected Compounds are evaluated by calculating apparent dissociation constants ($K_B$) for each concentration tested using the standard equation:

$$K_B=[\text{antagonist}]/(\text{dose ratio-1})$$

where dose ratio=antilog[(AG -log molar $EC_{50}$ without Compound)−(AG -log molar $EC_{50}$ with Compound)]. The $K_B$ values may be converted to the negative logarithms and expressed as -log molar $K_B$ (i.e. $pK_B$). For this evaluation, complete concentration-response curves for AG are obtained in the absence and presence of Compound (30 min incubation period) using paired tracheal rings. The potency of AG is determined at 50% of its own maximum response level in each curve. The $EC_{50}$ values are converted to the negative logarithms and expressed as -log molar $EC_{50}$. Maximum contractile responses to AG are determined by expressing the maximum response to AG as a percentage of the contraction caused by carbachol (30 µM), added after the initial equilibration period. When a statistically significant (p<0.05) reduction of the maximum response to AG is produced by a compound, the percent inhibition is calculated relative to the percentage of carbachol contraction in the untreated, paired tissue used as 100%.

Guinea Pig Labored Abdominal Breathing (Dyspnea) Assay (Test C)

Activity of a Compound of the invention as an antagonist of NKA at the NK2 receptor also may be demonstrated in vivo in laboratory animals, for example by adapting a routine guinea pig aerosol test described for evaluation of leukotriene antagonists by Snyder, et al. (Snyder, D. W., Liberati, N. J. and McCarthy, M. M., Conscious guinea-pig aerosol model for evaluation of peptide leukotriene antagonists. *J. Pharmacol. Meth.* (1988) 19, 219). Using the clear plastic chamber described previously by Snyder et al. to secure guinea pigs for a head-only aerosol exposure to bronchoconstrictor agonists, agonist is administered by aerosol to six conscious guinea pigs simultaneously during each maneuver. The tachykinin NK2-selective agonist, [β-ala$^8$]-NKA(4–10), $3\times10^{-5}$M, is aerosolized from a Devilhiss Model 25 ultrasonic nebulizer into an air stream entering the chamber at a rate of 2 L/minute.

Guinea pigs (275–400 g) are fasted for approximately 16 hours prior to experimentation. Compounds to be evaluated for blockade of effects of [β-ala$^8$]-NKA(4–10) or their vehicle (10% PEG400 in saline) are administered p.o. or i.v. at various times before aerosol agonist challenge. All animals are pretreated with atropine (10 mg/kg, i.p., 45 minutes pretreatment) indomethacin (10 mg/kg, i.p., 30 minutes pretreatment), propranolol (5 mg/kg, i.p., 30 minutes pretreatment), and thiorphan (1 mg/ml aerosol for 5 minutes, 15 minutes pretreatment).

Aerosol challenge with the agonist produces an initial increase in respiratory rate followed by a decrease with early signs of minor involvement of the abdominal muscles. The respiratory rate decreases further and the breathing becomes more labored with greater involvement of the abdominal muscles as exposure continues. The distinctly recognizable end point is the point where the breathing pattern of the guinea pig is consistently slow, deep, and deliberate, showing marked involvement of the abdominal muscles. Time, in seconds, from the onset of aerosol challenge to this end point is determined for each animal by using a stopwatch. The animals generally collapse after reaching the end point and do not recover from the agonist-induced respiratory distress. Antagonists result in an increase in the time to reach the end point. Animals receive the aerosol administration of agonist for a maximum time of 780 seconds.

Differences between drug treated groups and corresponding vehicle treated control groups are compared using Student's t-test for unpaired observations.

Clinical studies to demonstrate the efficacy of a Compound of the invention may be carried out using standard methods. For example, the ability of a Compound to prevent or treat the symptoms of asthma or asthma-like conditions may be demonstrated using a challenge of inhaled cold air or allergen and evaluation by standard pulmonary measurements such as, for example, $FEV_1$ (forced expiratory volume in one second) and FVC (forced vital capacity), analyzed by standard methods of statistical analysis.

It will be appreciated that the implications of a Compound's activity in Test A or Test B is not limited to asthma, but rather, that the test provides evidence of general antagonism of NKA. In general, the Compounds of the invention which were tested demonstrated statistically significant activity in Test A with a $K_i$ of 1 μM or much less. For example, nanomolar $K_i$ values of 2.6, 9, 2.8, 21.1, 2.0, 13, 3, and 3.5 typically were measured for the compounds described in Examples 1, 2, 6, 7, 9, 10, 13, and 24, respectively. In Test B, a $pK_B$ of 5 or greater was typically measured for a Compound of the invention. For example, $pK_B$ values of 8.0, 8.3, 8.5, 7.1, 8.6, 8.0, 8.6 and 8.2 were typically measured for the compounds described in Examples 1, 2, 6, 7, 9, 10, 13, and 24, respectively. It should be noted that there may not always be a direct correlation between the activities of Compounds measured as $K_i$ values in Test A and the values measured in other assays, such as the $pK_B$ measured in Test B. No untoward side-effects following i.v. or p.o. dosing of a Compound of the invention in Test C has been noted.

The surprisingly superior results in Test C following oral administration two hours prior to challenge with the agonist for the compounds of selected aspects of the invention compared with the compound of Example 1 are shown below.

| | | Test C (5 μmol/kg p.o., 120 min prior) | |
|---|---|---|---|
| Example Number | Test A $K_i$ (nM) | Test B $pK_B$ | percent protection | (number fully protected/ total number tested) |
| 1 | 2.6 | 8.2 | 17% | (0/6) |
| 9 | 2.0 | 8.6 | 90% | (5/6) |
| 13 | 3 | 8.6 | 78% | (3/6) |
| 14 | 0.3 | 9.5 | 100% | (8/8) |
| 15 | 2 | 8.7 | 100% | (6/6) |
| 16 | 0.6 | 8.2 | 88% | (5/6) |
| 27 | 2 | 7.9 | 54% | (2/6) |

As discussed above, a compound of formula I or a pharmaceutically acceptable salt thereof possesses NKA antagonist properties. Accordingly, it antagonizes at least one of the actions of NKA which are known to include bronchoconstriction, increased microvascular permeability, vasodilation and activation of mast cells. Accordingly, one feature of the invention is the use of a compound of formula I or a pharmaceutically acceptable salt thereof in the treatment of a disease in a human or other mammal in need thereof in which NKA is implicated and antagonism of its action is desired, such as, for example, the treatment of asthma or a related disorder. In addition, another feature of the invention is provided by the use of a compound of formula I or a salt thereof as a pharmacological standard for the development and standardization of new disease models or assays for use in developing new therapeutic agents for treating the diseases in which NKA is implicated or for assays for their diagnosis.

When used in the treatment of such a disease, a compound of the invention is generally administered as an appropriate pharmaceutical composition which comprises a compound of formula I or a pharmaceutically acceptable salt thereof as defined hereinbefore and a pharmaceutically acceptable diluent or carrier, the composition being adapted for the particular route of administration chosen. Such a composition is provided as a further feature of the invention. It may be obtained employing conventional procedures and excipients and binders, and it may be one of a variety of dosage forms. Such forms include, for example, tablets, capsules, solutions or suspensions for oral administration; suppositories for rectal administration; sterile solutions or suspensions for administration by intravenous or intramuscular infusion or injection; aerosols or nebulizer solutions or suspensions for administration by inhalation; or powders together with pharmaceutically acceptable solid diluents such as lactose for administration by insufflation.

For oral administration a tablet or capsule containing up to 250 mg (and typically 5 to 100 mg) of a compound of formula I may conveniently be used. For administration by inhalation, a compound of formula I will be administered to humans in a daily dose range of, for example, 5 to 100 mg, in a single dose or divided into two to four daily doses. Similarly, for intravenous or intramuscular injection or infusion a sterile solution or suspension containing up to 10% w/w (and typically 0.05 to 5% w/w) of a compound of formula I may conveniently be used.

The dose of a compound of formula I to be administered will necessarily be varied according to principles well known in the art taking account of the route of administration and the severity of the condition and the size and age of the patient under treatment. However, in general, the compound of formula I will be administered to a warm-blooded animal (such as man) so that a dose in the range of, for example, 0.01 to 25 mg/kg (and usually 0.1 to 5 mg/kg) is received. It will be understood that generally equivalent amounts of a pharmaceutically acceptable salt of a compound of formula I may be used.

The invention will now be illustrated by the following non-limiting examples in which, unless stated otherwise:

(i) temperatures are given in degrees Celsius (°C.); operations were carried out at room or ambient temperature, that is, at a temperature in the range of 18°–25° C.;

(ii) organic solutions were dried over anhydrous magnesium sulfate; evaporation of solvent was carried out using a rotary evaporator under reduced pressure (600–4000 pascals; 4.5–30 mm with a bath temperature of up to 60° C.;

(iii) chromatography means flash chromatography on silica gel; reversed phase chromatography means chromatography over octadecylsilane (ODS) coated support having a particle diameter of 32–74 μ, known as "PREP-40-ODS" (Art 731740-100 from Bodman Chemicals, Aston, Pa., U.S.A.); thin layer chromatography (TLC) was carried out on silica gel plates;

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory proton nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent; conventional abbreviations for signal shape are used; for AB spectra the directly observed shifts are reported; coupling constants (J) are given in Hz; Ar designates an aromatic proton when such an assignment is made;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the chemical ionization (CI) mode using a direct exposure probe; where indicated ionization was effected by electron impact (EI) or fast atom bombardment (FAB); values for m/z are given; generally, only ions which indicate the parent mass are reported.

EXAMPLE 1

N-[2-(3,4-Dichlorophenyl)-4-(4-phenylpiperidino)butyl]-N-methylbenzamide hydrochloride A solution of N-[2-(3,4-dichlorophenyl)-4-(4-phenyl-1,2,3,6-tetrahydropyridin-1-yl)butyl]-N-methylbenzamide (0.28 g) in methanol (10 mL) was treated with methanolic hydrogen chloride (2 mL), and 10% (w/w) palladium on carbon (0.03 g) was added. The reaction mixture was subjected to hydrogenation at atmospheric pressure for 2.5 hours. At the end of this period, the reaction mixture was treated with additional 10% palladium on carbon (0.03 g); and the hydrogenation was continued for an additional 16 hours. The reaction mixture was filtered through diatomaceous earth and evaporated. The resulting material was treated with ether and evaporated; and the process was repeated twice. The residue was crystallized from a mixture of ethyl acetate, methanol, ether and hexane; washed with a mixture of ether and hexane; and dried under vacuum to afford the title compound as a white solid (0.11 g); mp 142°–148° C.; NMR (CD$_3$OD): 1.8–2.4 (m, 6), 2.6–3.2 (m, 9), 3.5–3.9 (m, 4), 7.0–7.6 (m, 13); MS: m/z=495(M+1). Analysis for C$_{29}$H$_{32}$Cl$_2$N$_2$O·HCl·H$_2$O: Calculated: C, 63.33; H, 6.41; N, 5.09; Found: C, 63.46; H, 6.12; N, 5.13.

The intermediate N-[2-(3,4-dichlorophenyl)-4-(4-phenyl-1,2,3,6-tetrahydropyridin-1-yl)butyl]-N-methylbenzamide was prepared as follows.

a. 2-Tetrahydropyran-2-yloxyethyl bromide

To a mechanically stirred solution of dihydropyran (1000 mL) and a strong acid resin (10.0 g) in hexane (2000 mL) was added 2-bromoethanol (985 g) dropwise over a period of 1.5 hours in a cold water bath to maintain an internal temperature of 35°–40° C. After being stirred overnight at room temperature, the reaction mixture was chromatographed, with hexane as the eluent. The hexane was evaporated to give an amber liquid which was distilled through a 2 inch (5 cm) diameter vigreux cole, collecting the material boiling between 75°–95° C. (3,300–4,700 Pa). This material was redistilled to give the ether as an oil (1195.5 g); bp 80°–90° C. (2666 Pa); NMR: 4.68 (m, 1), 4.01 (m, 1), 3.89 (m, 1), 3.77 (m, 1), 3.52 (m, 3), 1.75–1.50 (m, 6).

b. α-[2-(Tetrahydropyran-2-yloxy)ethyl]-3,4-dichlorophenylacetonitrile

To a solution of sodium hydride (218.0 g of a 55% oil suspension) in tetrahydrofuran (4 L) at 10° C. in an ice/water bath was added 3,4-dichlorophenylacetonitrile (893.0 g) in tetrahydrofuran (2 L) over a period of 45 minutes, and the resulting solution was allowed to stir for 2 hours at room temperature. The mixture was cooled in an ice/water bath and 2-tetrahydropyran-2-yloxyethyl bromide (1076.0 g) was dropped in as a neat oil over a period of 25 minutes. The mixture was stirred overnight at room temperature and divided into four 2-liter portions. Each portion was diluted with saturated ammonium chloride (3 L) and extracted with ether (500 mL). The combined organic layers were washed (aqueous ammonium chloride), dried, and evaporated. The resulting material was chromatographed, with hexane:dichloromethane (gradient 100:0, 0:100) as eluent, to give the nitrile as an oil (932 g); NMR: 7.47 (m, 4), 7.20 (m, 2), 4.57 (m, 2), 4.08 (m, 2), 3.85 (m, 4), 3.54 (m, 3), 3.37 (m, 1), 2.15 (m, 4), 1.77 (m, 4), 1.56 (m, 8).

c. 2-(3,4-Dichlorophenyl)-4-(tetrahydropyran-2-yloxy)butylamine

To a solution of the above nitrile (128.3 g) in 95% ethanol (1.1 L) and concentrated ammonium hydroxide (550 mL) was added Raney Nickel (25.0 g). The mixture was hydrogenated under a hydrogen atmosphere (3.65 bar) at room temperature for 1.5 days. The mixture was filtered through diatomaceous earth to remove the catalyst, and the resulting filtrate was evaporated. The resulting material was chromatographed, with dichloromethane:methanol (gradient 100:0, 95:5) as eluent, to give the amine (91 g) as an oil; NMR: 7.40 (s, 1), 7.38 (s, 1), 7.32 (d, 1, J=2.1), 7.28 (d,1, J=2.0), 7.07 (dd, 1, J=2.1, 4.9), 7.04 (dd, 1, J=2.1, 4.9), 4.50 (m, 1), 4.43 (m, 1), 3.70 (m, 4), 3.45 (m, 2), 3.27 (m, 1), 3.17 (m, 1), 2.97–2.75 (m, 6), 2.00 (m, 2), 1.82–1.66 (m, 6), 1.53 (m, 8), 1.18 (broad s, 4); MS: m/z=318(M+1).

d. N-[2-(3,4-Dichlorophenyl)-4-(tetrahydropyran-2-yloxy)butyl]benzamide

To a solution of 2-(3,4-dichlorophenyl)-4-(tetrahydropyran-2-yloxy)butylamine (2.5 g) in dichloromethane (35 mL) was added triethylamine (1.1 mL) and benzoic anhydride (1.85 g), and the resulting solution was allowed to stir for 45 minutes. The mixture was washed (0.2N hydrochloric acid, 1N sodium hydroxide, water), dried, and evaporated to give the amide as an oil (3.3 g); NMR: 7.63 (m, 4), 7.46 (m, 2), 7.37 (m, 8), 7.09 (m, 2), 6.22 (m, 2), 4.50 (m, 1), 4.43 (m, 1), 3.8 (m, 5), 3.63 (m, 1), 3.5 (m, 4), 3.36 (m, 1), 3.23 (m, 1), 3.11 (m, 2), 2.06 (m, 2), 1.90–1.77 (m, 4), 1.68 (m, 2), 1.51 (m, 8); MS: m/z=338[(M+1)-tetrahydropyranyl].

e. N-[2-(3,4-Dichlorophenyl)-4-(tetrahydropyran-2-yloxy)butyl]-N-methylbenzamide To a solution of N-[2-(3,4-dichlorophenyl)-4-(tetrahydropyran-2-yloxy)butyl]benzamide (3.3 g) in dimethyl sulfoxide (20 mL) was added powdered potassium hydroxide (1.6 g), followed by iodomethane (1.0 mL) after 15 minutes. After 1 hour, the mixture was diluted with water (330 mL) and extracted with dichloromethane. The combined organic extracts were dried and evaporated to give the N-methylbenzamide (3.1 g) as an oil; MS: m/z=352[(M+1)-tetrahydropyranyl].

f. N-[2-(3,4-Dichlorophenyl)-4-hydroxybutyl]-N-methylbenzamide

To a solution of N-[2-(3,4-dichlorophenyl)-4-(tetrahydropyran-2-yloxy)butyl]-N-methylbenzamide (10.5 g) in tetrahydrofuran (100 mL) was added 6N hydrochloric acid (50 mL), and the resulting solution was allowed to stir overnight. The mixture was neutralized with 10N sodium hydroxide, diluted with water, and extracted with dichloromethane. The organic layer was dried and evaporated. The resulting yellow solid was suspended in ether and filtered to give the alcohol as a white solid (8.4 g); MS: m/z=352(M+1).

g. N-[2-(3,4-Dichlorophenyl)-4-oxobutyl]-N-methylbenzamide

A solution of oxalyl chloride (878 mg) in dichloromethane (5 mL) was cooled to −78° C. and was treated dropwise with a solution of dimethyl sulfoxide (595 mg) in dichloromethane (2 mL). The resulting mixture was stirred at −78° C. for 15 minutes, and was treated dropwise with a solution of N-[2-(3,4-dichlorophenyl)-4-hydroxybutyl]-N-methylbenzamide (1.22 g) in dichloromethane (10 mL)/dimethyl sulfoxide (2 mL). The mixture was stirred at −78° C. for 1 hour, was treated with triethylamine (1.75 g), warmed to room temperature and stirred for 1 hour. The mixture was then poured into water and extracted with dichloromethane. The organic extract was washed (water, brine), dried, filtered through activated magnesium silicate [Florisil (trademark)] and evaporated to afford the aldehyde as a pale yellow oil (1.18 g); MS: m/z=350[(M+1), $^{35}Cl_2$].

h. N-[2-(3,4-Dichlorophenyl)-4-(4-hydroxy-4-phenylpiperidino)butyl]-N-methylbenzamide A solution of 4-hydroxy-4-phenyl-piperidine (1.99 g) in methanol (20 mL) was cooled to 0° C. and the pH was adjusted to 8 by adding acetic acid. To this solution was added N-[2-(3,4-dichlorophenyl)-4-oxobutyl]-N-methylbenzamide (3.57 g) in methanol (20 mL), and the resulting reaction mixture was treated with sodium cyanoborohydride (0.765 g). Upon warming to the room temperature, the reaction mixture was stirred for 16 hours and treated with saturated sodium bicarbonate solution. The solution was extracted with dichloromethane, dried (anhydrous sodium sulfate) and evaporated. The resulting material was purified by chromatography, with dichloromethane:methanol (90:10) as the eluent, to give the piperidine (2.42 g); NMR (CDCl$_3$): 1.5–2.5 (m, 10), 2.68 (broad, 4), 3.47 (s, 3), 3.5–3.57 (m, 1), 6.8–7.5 (m, 13); MS: m/z=511(M+1). This material was used in the next step without further purification.

i. N-[2-(3,4-Dichlorophenyl)-4-(4phenyl-1,2,3,6-tetrahydropyridin-1-yl)butyl]-N-methylbenzamide A mixture of the alcohol described above at Example 1.h. (2.5 g) and concentrated hydrochloric acid (20 mL) was heated to 100° C. for 2 hours. The reaction mixture was cooled to room temperature, poured into saturated sodium bicarbonate solution, and extracted with dichloromethane. The organic extracts were dried (anhydrous sodium sulfate) and evaporated. The resulting material was purified by chromatography, with methanol:dichloromethane (1:12) as the eluent, to give the tetrahydropyridine (0.81 g); NMR (CD$_3$OD): 1.5–1.9 (broad, 3), 2.3 (broad, 1), 2.7–2.4 (m, 3), 2.76 (s, 2), 3.04 (s, 3), 3.14 (broad, 1), 3.8–3.7 (m, 2), 6.08 (d, 1, J=18), 6.9–7.6 (m, 13); MS: m/z=493(M+1). This material was used in the next step without further characterization.

EXAMPLE 1

(Alternative Preparation)

The title compound was also prepared as follows.

A solution of 4-phenylpiperidine (0.48 g) in methanol (18 mL) was treated with 18 drops of acetic acid followed by a solution of N-[2-(3,4-dichlorophenyl)-4-oxobutyl]-N-methylbenzamide (1.04 g) in methanol (20 mL). The mixture was treated with sodium cyanoborohydride (0.28 g) and stirred at the ambient temperature for 16 hours. The mixture was treated with water and evaporated. The residue was diluted with dichloromethane and washed (saturated solution of sodium bicarbonate). The organic layer was dried (anhydrous sodium sulfate) and evaporated. Chromatography, with dichloromethane:methanol (95:5) as the eluent, afforded an oil (1.6 g). This material was converted to the corresponding hydrochloride salt as follows: The oil was dissolved in dichloromethane (6 mL), treated with ethereal hydrogen chloride (6 mL), and diluted with ether (100 mL). The resulting suspension was stirred for 26 hours, and the precipitate was collected by filtration to afford the title compound (0.98 g); mp 102°–141° C. (dec). This material was identical to the 4-phenylpiperidine compound described above in Example 1.

EXAMPLE 2

N-[2-(3,4-Dichlorophenyl)-4-[4-(2-methoxyphenyl)piperidino]butyl]-N-methylbenzamide hydrochloride N-(2-Methoxyphenyl)piperidine (0.19 g) and N-[2-(3,4-dichlorophenyl)-4-oxobutyl]-N-methylbenzamide (0.35 g) were subjected to a procedure similar to that described in Example 1 (alternative preparation) to give crude material. This material was transformed to the hydrochloride salt to afford the title compound as a white solid (0.42 g); mp 85°–100° C. (dec); NMR (CD$_3$OD): 1.29–1.38 (broad, 2), 2.05 (broad, 5), 2.2 (broad, 1), 2.7 (s, 2), 2.7–3.3 (broad, 5), 3.4–3.7 (broad, 2), 3.7–3.9 (broad, 5), 6.9–7.0 (m, 3), 7.15–7.24 (m, 4), 7.36–7.45 (m, 4), 7.56–7.62 (m, 1); MS: m/z=509(M+1). Analysis for $C_{30}H_{34}Cl_2N_2O_2 \cdot HCl \cdot 0.75 H_2O$: Calculated: C, 62.61; H, 6.39; N, 4.87; Found: C, 62.73; H, 6.78; N, 4.76.

The intermediate 4-(2-methoxyphenyl)piperidine was prepared as follows:

a. 1-Benzyloxycarbonyl-4-piperidone

A suspension of 4-piperidone hydrochloride (11.96 g) in tetrahydrofuran (150 mL) was cooled to 0° C. and treated with benzyl chloroformate (14.3 mL). The reaction mixture was treated, dropwise, with 67 mL of an aqueous solution of sodium hydroxide (7.84 g in 76 mL of water) and allowed to stir for 2 hours. The reaction mixture was extracted with ethyl acetate, the organic layer was washed with water, dried and evaporated to afford the piperidone as a pale yellow oil (20.58 g); NMR (CDCl$_3$): 2.45 (t,4, J=6), 3.79 (t,4, J=6), 5.18 (s, 2), 7.32–7.38 (m, 5); MS: m/z=234(M+1). This material was used in the next step without further purification.

b. 1-Benzyloxycarbonyl-4-hydroxy-4-(2-methoxyphenyl)piperidine

A solution of anisole (2.19 g) in tetrahydrofuran (50 mL) was cooled to −78° C. and treated with tert-butyl lithium (12 mL of a 1.7M solution in pentane). The resulting reaction mixture was warmed to −15° C. and stirred for 45 minutes. The reaction mixture was cooled back to −78° C. and treated with a solution of 1-benzyloxycarbonyl-4-piperidone (4.67 g) in tetrahydrofuran (5 mL). The reaction mixture was warmed to −15° C. and stirred for 1 hour before it was allowed to reach ambient temperature and stirred for 72 hours. The reaction mixture was diluted with water, and extracted several times with ethyl acetate. The combined organic layers were dried and evaporated to afford the crude product. Chromatography, with hexane:ethyl acetate (2:1) as the eluent, gave a mixture of the alcohol and starting material (2.98 g); NMR (CDCl$_3$): 1.95–2.04 (m, 4), 2.9 (broad, 2), 3.90 (s, 3), 5.15 (s, 2), 6.93–6.99 (m, 2), 7.21–7.36 (m, 7); MS: m/z=342(M+1). This material was used in the next step without further purification.

c. 1-Benzyloxycarbonyl-4-(2-methoxyphenyl)piperidine

A solution of 1-benzyloxycarbonyl-4-hydroxy-4-(2-methoxyphenyl)piperidine (2.59 g) in dichloromethane (45 mL) was treated with trifluoroacetic acid (8.6 g) followed by triethylsilane (17.5 g). The resulting brown reaction mixture was stirred for 5 minutes and then poured into a saturated solution of sodium bicarbonate. The bicarbonate solution was extracted with dichloromethane. The dichloromethane solution was dried and evaporated to give the des-hydroxy compound (2.1 g); NMR (CDCl$_3$): 1.55–1.66 (m, 2), 1.78–1.82 (br, 2), 2.91, (m, 2), 3.11 (m, 1), 3.8 and 3.82 (s, 3), 4.32 (br, 2), 5.12–5.28 (m, 2), 6.84 (d, 4, J=9), 6.87–6.95 (m, 1), 7.11–7.25 (m, 2), 7.29–7.38 (m, 5); MS: m/z=326 (M+1). This material was used in the next step without further purification.

d. 4-(2-Methoxyphenyl)piperidine

A solution of 1-benzyloxycarbonyl-4-(2-methoxyphenyl)piperidine (0.67 g) in ethanol (10 mL) was treated with cyclohexene (4.2 mL) followed by 10% palladium on carbon (0.13 g). After heating to reflux for 2 hours, the reaction mixture was cooled to room temperature, diluted with ether and extracted with 1N hydrochloric acid. The aqueous layer was made basic with sodium bicarbonate and extracted with dichloromethane. The organic layers were dried over anhydrous sodium sulfate and evaporated to afford the piperidine (0.2 g); NMR (CDCl$_3$): 1.60 (d of q, 2, J$_1$=12, J$_2$=4), 1.73–1.82 (broad, 2), 2.74–2.83 (d of t, 2, J$_1$=12, J$_2$=2), 3.02–3.2 (m, 3), 3.82 (s, 3), 6.85 (d, 1, J=8), 6.9 (m, 1), 7.15–7.26 (m, 2); MS: m/z=192(M+1). This material was used in the next step without further purification.

EXAMPLE 3

N-[2-(3,4-Dichlorophenyl)-4-[4-(4-methoxyphenyl)piperidino]butyl]-N-methylbenzamide hydrochloride Using a procedure similar to that described in Example 1 (alternative preparation) except using 4-(4-methoxyphenyl)piperidine, the N-methylbenzamide was prepared. The resulting product was chromatographed, with dichloromethane:methanol (19:1) as the eluent, and converted to the hydrochloride salt to provide the title compound as a white solid; mp 167°–169° C.; NMR (CD$_3$OD): 1.92–2.05 (m, 3), 2.24 (br, 1), 2.79 (s, 3), 2.8–3.3 (m, 4), 3.3–3.6 (m, 3), 3.7–3.9 (m, 4), 6.88 (m, 2), 7.0 (d, 1, J=8), 7.16–7.22 (m, 4), 7.37–7.45 (m, 4), 7.57–7.64 (m, 1); MS: m/z=525(M+1). Analysis for C$_{30}$H$_{34}$Cl$_2$N$_2$O$_2$·HCl·0.75 H$_2$O: Calculated: C, 62.13; H, 6.43; N, 4.83; Found: C, 62.39; H, 6.20; N, 4.82.

The intermediate 4-(4-methoxyphenyl)piperidine was prepared as follows:

a. 1-Benzyloxycarbonyl-4-hydroxy-4-(4-methoxyphenyl)piperidine

4-Bromoanisole was subjected to a procedure similar to that described in Example 2.b., except that the reaction was not warmed above −78° C., to give the alcohol. The product was contaminated with the starting piperidone (4:3 by NMR); NMR (CDCl$_3$): 1.7 (d, 2, J=13), 1.8–2.1 (broad, 2), 3.2 (broad, 2), 3.8 (m, 3), 4.1 (broad, 2), 5.1 (s, 2), 6.87–6.9 (m, 2), 7.25–7.4 (m, 7); MS: m/z=324(M-18). This material was used in the next step without further purification.

b. 1-Benzyloxycarbonyl-4-(4-methoxyphenyl)piperidine

1-Benzyloxycarbonyl-4-hydroxy-4-(4-methoxyphenyl)piperidine was subjected to a procedure similar to that described in Example 2.c. The resulting product was chromatographed, with hexane:ethyl acetate (3:1) as the eluent, to give the des-hydroxy compound; NMR (CDCl$_3$): 2.61 (m, 1), 2.81 (broad, 2), 3.78 (s, 3), 4.32 (broad, 2), 5.15 (s, 2), 6.84 (d, 2, J=7), 7.1 (d, 2, J=8), 7.31–7.38 (m, 5); MS: m/z=326(M+1). This material was used in the next step without any further purification.

c. 4-(4-Methoxyphenyl)piperidine

A solution of 1-benzyloxycarbonyl-4-(4-methoxyphenyl)piperidine (0.42 g) in ethanol (5 mL) was treated with 10% palladium on carbon (0.04 g) and hydrogenated for 16 hours at atmospheric pressure. The reaction mixture was filtered through diatomaceous earth and evaporated to afford 4-(4-methoxyphenyl)piperidine as a colorless oil (0.22 g); NMR (CDCl$_3$): 1.59–1.71 (m, 2), 1.85 (d, 2, J=12), 2.71–2.81 (d of t,2, J=12), 3.19–3.23 (broad, 2), 3.79 (s, 3), 6.83–6.87 (m, 2), 7.12–7.26 (m, 2); MS: m/z=192(M+1). This material was used in the next step without further purification.

EXAMPLE 4

N-[2-(3,4-Dichlorophenyl)-4-[4-(3-methoxyphenyl)piperidino]butyl]-N-methylbenzamide hydrochloride Using a procedure similar to that described in Example 1 (alternative preparation), except using 4-(3-methoxyphenyl)piperidine, the N-methylbenzamide was prepared. The resulting product was chromatographed, with dichloromethane:methanol (19:1) as the eluent, and converted to the hydrochloride salt to provide the title compound as a white solid (0.25 g); mp 172°–176° C.; NMR (CD$_3$OD): 1.85–2.14 (broad, 3), 2.15–2.36 (broad, 1), 2.6–2.95 (broad, 4), 2.9–3.3 (m, 4), 3.4–3.7 (m, 2), 3.7–3.9 (broad, 1), 3.96 (s, 3), 6.78–6.83 (m, 3), 6.99 (d, 1, J=7), 7.1–7.3 (m, 3), 7.36–7.43 (m, 4), 7.56–7.63 (m, 1); MS: m/z=525(M+1). Analysis for C$_{30}$H$_{34}$Cl$_2$N$_2$O$_2$·HCl·0.5 H$_2$O: Calculated: C, 63.11; H, 6.35; N, 4.91; Found: C, 63.01; H, 6.21; N, 4.80.

The intermediate 4-(3-methoxyphenyl)piperidine was prepared as follows:

a. 1-Benzyloxycarbonyl-4-hydroxy-4-(3-methoxyphenyl)piperidine

Using a method similar to that described in Example 2.b., except that the reaction was not warmed above −78° C. and 3-bromoanisole was used instead of anisole, the alcohol was prepared. The product was contaminated with the starting piperidone (2:1 as indicated by NMR); NMR (CDCl$_3$): 1.72–1.77 (broad, 2), 2.04 (broad, 2), 3.25 (broad, 2), (s, 3), 4.0–4.25 (broad, 2), 5.1 (s, 2), 6.83 (m, 2), 7.02–7.4 (m, 2), 7.26–7.39 (m, 6); MS: m/z=324(M+18). This material was used in the next step without further purification.

b. 1-Benzyloxycarbonyl-4-(3-methoxyphenyl)piperidine

1-Benzyloxycarbonyl-4-hydroxy-4-(3-methoxyphenyl)piperidine (1.79 g) was subjected to a procedure similar to that described in Example 2.c. The crude product was chromatographed, with hexane:ethyl acetate (2:1) as the eluent, to give the des-hydroxy compound (1.29 g); MS: m/z=326(M+1); NMR of this material was complex. This material was used in the next step without any further purification.

c. 4-(3-Methoxyphenyl)piperidine

A procedure similar to that described in Example 3.c. was used. 1-Benzyloxycarbonyl-4-(3-methoxyphenyl)piperidine (0.42 g) upon catalytic hydrogenation in the presence of 10% palladium on carbon afforded 4-(3-methoxyphenyl)piperidine as a pale yellow oil (0.19 g); NMR (CDCl$_3$): 1.64–1.77 (m, 2), 1.85 (broad, 2), 2.74 (m, 2), 3.21–3.25

(broad, 2), 3.80 (s, 3), 6.73–6.83 (m, 3), 7.21–7.26 (t,1, J=8); MS: m/z=192(M+1). This material was used in the next step without further purification.

EXAMPLE 5

N-[2-(3,4-Dichlorophenyl)-4-[4-(4-hydroxyphenyl) piperidino]butyl]-N-methylbenzamide hydrochloride Using a procedure similar to that described in Example 1 (alternative preparation), except using 4-(4-hydroxyphenyl) piperidine, the N-methylbenzamide was prepared. The product was chromatographed, with dichloromethane:methanol (9:1) as the eluent, and converted to the hydrochloride salt to provide the title compound as a white solid (0.28 g); mp 148°–154° C. (dec); NMR (CD$_3$OD): 1.8–2.14 (br, 4), 2.1–2.2 (broad, 2), 2.7–3.1 (m, 8), 3.5–3.7 (broad, 2), 3.81–3.85 (m, 2), 6.7 (d, 2, J=8), 6.9–7.2 (m, 5), 7.3–7.44 (m, 4.5), 7.5–7.6 (m, 1.5); MS: m/z=511(M+1). Analysis for C$_{29}$H$_{32}$Cl$_2$N$_2$O$_2$·HCl·0.5 H$_2$O: Calculated: C, 62.53; H, 6.15; N, 5.03; Found: C, 62.53; H, 6.20; N, 4.95.

The intermediate 4-(4-hydroxyphenyl)piperidine was prepared as follows:

a. 4-Benzyloxybromobenzene

A solution of 4-bromophenol (17.3 g) in dimethylformamide (200 mL) was treated with potassium carbonate (15.2 g) followed by benzyl bromide (17.1 g 11.9 mL). After stirring for 16 hours at ambient temperature, the reaction mixture was diluted with water and hexane. The aqueous layer was extracted with hexane:ether (5:1). The organic extracts were washed (water, 1N sodium hydroxide, brine), dried and evaporated to give the bromobenzene as a white solid (23.4 g); NMR (CDCl$_3$): 5.03 (s, 2), 6.85 (dd, 2, J$_1$=5, J$_2$=2), 7.3–7.4 (m, 7); MS: m/z=263(M+1). This material was used in the next step without further purification.

b. 1-Benzyloxycarbonyl-4-hydroxy-4-(4-benzyloxyphenyl) piperidine

A solution of 4-benzyloxybromobenzene (6.6 g) in tetrahydrofuran (125 mL) was cooled to −78° C. and treated with n-butyl lithium (10 mL of a 2.5M solution in hexane). After stirring for 20 minutes at −78° C., a solution of 1-benzyloxycarbonyl-4-piperidone (5.85 g) in tetrahydrofuran (5 mL) was added; and the reaction mixture was stirred at −78° C. for 1 hour followed by 2 hours at 0° C. The resulting solution was treated with water (10 mL) and extracted with ethyl acetate. The organic layer was washed with brine, dried and evaporated to afford a crude product which was chromatographed, with hexane:isopropanol (9:1) as the eluent, to give two fractions (1.91 and 4.05 g each). The first fraction was a 1:1 mixture of the alcohol and the starting ketone as indicated by NMR, while the second fraction was the alcohol (39% yield); NMR (CDCl$_3$): 1.74 (d, 2, J=13), 2.04 (broad, 1), 3.32 (m, 2), 4.09 (broad, 2), 5.05 (s, 2), 5.14 (s, 2), 6.96 (m, 2), 7.29–7.49 (m, 12); MS: m/z=450(M+18).

c. 1-Benzyloxycarbonyl-4-(4-benzyloxyphenyl)piperidine

1-Benzyloxycarbonyl-4-hydroxy-4-(4-benzyloxyphenyl) piperidine was subjected to a procedure similar to that described in Example 2.c. The resulting product was chromatographed, with hexane:ethyl acetate (2:1) as the eluent, to give the des-hydroxy compound contaminated with the corresponding alkene (3.48 g); MS: m/z=402(M+1); NMR of this material was complex. This material was used in the next step without any further purification.

d. 4-(4-Hydroxyphenyl)piperidine

1-Benzyloxycarbonyl-4-(4-benzyloxyphenyl)piperidine (0.65 g) was subjected to a procedure similar to that described in Example 3.c. to give 4-(4-hydroxyphenyl) piperidine as a brown solid (0.28 g); NMR (CDCl$_3$): 1.3–1.5 (m, 2), 1.6 (broad, 2), 2.9–3.0 (broad, 2), 6.66 (d, J=8 ), 6.99 (d, 2, J=8); MS: m/z=178(M+1). This material was used in the next step without further purification.

EXAMPLE 6

N-[2-(3,4-Dichlorophenyl)-4-[4-(2-hydroxyphenyl) piperidino]butyl]-N-methylbenzamide hydrochloride Using a procedure similar to that described in Example 1 (alternative preparation) except using 4-(2-hydroxyphenyl) piperidine, the N-methylbenzamide was prepared. The resulting product was chromotographed, with dichloromethane:methanol (19:1) as the eluent, and converted to the hydrochloride salt to provide the title compound as a white solid (0.33 g); mp 225°–228° C.; NMR (CD$_3$OD): 1.9–2.1 (broad, 5), 2.3 (broad, 2), 2.79 (s, 3), 3.6 (broad, 2), 3.81–3.85 (m, 2), 6.79 (m, 2), 7.0–7.3 (m, 5), 7.3–7.5 (m, 4.5), 7.6 (m, 1.5); MS: m/z=511(M+1). Analysis for C$_{29}$H$_{32}$Cl$_2$N$_2$O$_2$·HCl·0.5 H$_2$O: Calculated: C, 62.53; H, 6.15; N, 5.03; Found: C, 62.58; H, 6.13; N, 4.94.

The intermediate 4-(2-hydroxyphenyl)piperidine was prepared as follows:

a. 2-Benzyloxybromobenzene

A solution of 2-bromophenol (17.3 g) in dimethylformamide (200 mL) was treated with potassium carbonate (15.2 g) followed by benzyl bromide (17.1 g, 11.9 mL). After stirring for 3 hours at the room temperature, the reaction mixture was diluted water and hexane. The aqueous layer was extracted with hexane; and the organic layers were washed (water, 1N sodium hydroxide, brine), dried and evaporated to give the product as a colorless oil (22.94 g). This material was fractionally distilled under reduced pressure to afford the bromobenzene (16.52 g); bp 110°–145° C. (1333 Pa); NMR (CDCl$_3$): 5.17 (s, 2), 6.65 (d of t,1, J=8, J=1), 6.92–6.96 (d of d, 1, J=8, J=1), 7.19–7.26 (m, 1), 7.33–7.42 (m, 3), 7.46–7.50 (m, 2), 7.55 (d of d, 1, J=9, J=2). This material was used in the next step without further purification.

b. 1-Benzyloxycarbonyl-4-hydroxy-4-(2-benzyloxyphenyl) piperidine

Using a procedure similar to that described in Example 5.b., except using 2-benzyloxybromobenzene, the crude hydroxy compound was prepared. The resulting product was chromatographed, with hexane:isopropanol (9:1) as the eluent, to give the hydroxy compound (2.86 g); NMR (CDCl$_3$): 2.04 (m, 4), 3.4 (broad, 2), 4.0–4.1 (broad, 3), 5.13–5.16 (m, 4), 6.96–7.02 (m, 2), 7.22–7.27 (m, 3), 7.30–7.41 (m, 9); MS: m/z=418(M+1).

c. 1-Benzyloxycarbonyl-4-(2-benzyloxyphenyl)piperidine

1-Benzyloxycarbonyl-4-hydroxy-4-(2-benzyloxyphenyl) piperidine was subjected to a procedure similar to that described in Example 2.c. The resulting product was chromatographed, with hexane:ethyl acetate (3:1) as the eluent, to give the piperidine (1.67 g, contaminated with an impurity); NMR (CDCl$_3$): 1.60–1.64 (m, 2), 1.84 (broad, 2), 2.89 (broad, 2), 3.15–3.2 (m, 1), 4.31 (s, 2), 5.09 (d, 2, J=7), 5.17 (d, 2), 6.91–7.15 (m, 2), 7.17–7.21 (m, 2), 7.25–7.41 (m, 10); MS: m/z=402(M+1). This material was used in the next step without any further purification.

d. 4-(2-Hydroxyphenyl)piperidine

1-Benzyloxycarbonyl-4-(2-benzyloxyphenyl)piperidine was subjected to a procedure similar to that described in Example 3.c. to give 4-(2-hydroxyphenyl)piperidine as a brown solid (0.36 g); NMR (CDCl$_3$): 1.7–1.9 (m, 4), 2.77–2.86 (m, 2), 2.99–3.04 (m, 1), 3.23 (d, 2, J=12), 4.17 (s, 2), 6.72 (d, 1, J=8), 6.84 (t,1, J=7), 7.05 (m, 1); MS: m/z=178(M+1). This material was used in the next step without further purification.

EXAMPLE 7

N-[2-(3,4-Dichlorophenyl)-4-[4-(5-methyl-1,3,4-oxadiazol-2-yl)piperidino]butyl]-N-methylbenzamide hydrochloride Using a procedure similar to that described in Example 1 (alternative preparation), except using 4-(5-methyl-1,3,4-oxadiazol-2-yl)piperidine, the title compound was obtained as a white solid; mp 121°–124° C.; NMR: 7.61–7.19 (m, 8), 3.82–3.75 (m, 2), 3.07, 2.77 (2s, 3, N—$CH_3$), 2.51 (s, 3), 2.40–2.00 (broad m, 8); MS: m/z=529(M+1+28), m/z=501 [(M+1), $^{35}Cl_2$]. Analysis for $C_{26}H_{30}Cl_2N_4O_2 \cdot 1.0$ HCl·0.25 $H_2O$: Calculated: C, 57.57; H, 5.85; N, 10.33; Found: C, 57.53; H, 6.01; N, 10.06.

The intermediate piperidine was prepared as follows.

a. Ethyl 1-(benzyloxycarbonyl)-4-piperidinecarboxylate

A solution of ethyl 4-piperidinecarboxylate (14.71 g) and triethylamine (12.04 g) in chloroform (200 mL) was cooled to 0° C. and treated dropwise with benzyl chloroformate (17.91 g). The resulting mixture was stirred at 0° C. for 1 hour, then was warmed to room temperature and was stirred for 12 hours. The mixture was then washed (1N hydrochloric acid, brine), dried, filtered and evaporated to yield a pale yellow oil (26.4 g). The oil was purified by chromatography, with dichloromethane:methanol (95.5) as the eluent, to afford the urethane as a colorless syrup (22.15 g); NMR: 7.35 (m, 5), 5.07 (s, 2), 4.06 (q,2, J=7.0), 3.91 (broad d, 2, J=13.3), 2.95 (broad, 2), 2.53 (m, 1), 1.82 (broad d, 2, J=13.3), 1.41 (m, 2), 1.18 (t, 3, J=7.0).

b. 1-Benzyloxycarbonyl-4-piperidinecarbohydrazide

A solution of ethyl 1-(benzyloxycarbonyl)-4-piperidinecarboxylate (2.50 g) and hydrazine hydrate (0.65 g) in ethanol (30 mL) was heated under reflux for 16 hours. Additional hydrazine hydrate (1.29 g) was then added, and the mixture heated for an additional 24 hours. The reaction mixture was then cooled and evaporated. The residue was diluted with dichloromethane and washed sequentially with water and brine. The organic extract was dried, filtered and evaporated. The solid was suspended in ether, filtered and dried to afford the carbohydrazide as a white solid (1.69 g); mp 123°–125° C.; NMR: 7.35 (m, 5), 5.11 (s, 2), 4.21 (broad, 2), 2.82 (broad, 2), 2.25 (m, 1), 1.85–1.60 (m, 4); MS: m/z=308(M+1+28).

c. 1-Benzyloxycarbonyl-4-(5-ethoxy-5-methyl-1,3,4-oxadiazolin-2-yl)piperidine

A suspension of 1-benzyloxycarbonyl-4-piperidinecarbohydrazide (0.66 g) and ethyl acetimidate hydrochloride (0.35 g) in ethanol (5 mL) was heated under reflux for 3 hours, then was cooled to room temperature and the solvent was evaporated. The residue was dissolved in dichloromethane, washed (water, brine), dried and evaporated to afford the oxadiazolin-2-yl piperidine as a white solid (0.66 g); mp 129°–131° C.; NMR (CDCl$_3$): 8.66 (s, 1), 7.35 (m, 5), 5.13 (s, 2), 4.21–4.15 (m, 2), 4.04 (q,2, J=7.0), 3.10 (m, 1), 2.89 (m, 2), 1.98 (s, 3), 1.80–1.60 (m, 4), 1.28 (t,3, J=7.0). Analysis for $C_{18}H_{25}N_3O_4$: Calculated: C, 62.23; H, 7.25; N, 12.10; Found: C, 62.03; H, 7.11; N, 12.00.

d. 1-Benzyloxycarbonyl-4-(5-methyl-1,3,4-oxadiazol-2-yl) piperidine

A solution of 1-benzyloxycarbonyl-4-(5-ethoxy-5-methyl-1,3,4-oxadiazolin-2-yl)piperidine (200 mg) in toluene (5 mL) containing pyridine (0.25 mL) was heated under reflux for 20 hours. The mixture was cooled to room temperature, and the solvent was evaporated. The residue was purified by chromatography, eluting with chloroform:methanol:ammoniumhydroxide (98:2:1), to give the 1,3,4-oxadiazole derivative (0.143 g) as a clear oil; NMR (CDCl$_3$): 7.35 (m, 5), 5.13 (s, 2), 4.16 (broad d, 2, J=12.8), 3.05 (m, 1), 2.50 (s, 3), 2.04 (m, 2), 1.83 (m, 2).

e. 4-(5-Methyl-1,3,4-oxadiazol-2-yl)piperidine

A solution of 1-benzyloxycarbonyl-4-(5-methyl-1,3,4-oxadiazol-2-yl)piperidine (0.18 g) in ethanol (5 mL) was hydrogenated over 10% palladium on carbon (0.050 g) at a hydrogen pressure of 1 bar for 2 hours. The catalyst was then removed by filtration through diatomaceous earth, the filter cake was washed with ethanol and the solvent evaporated to afford the piperidine as a white crystalline solid (0.98 g); mp 64°–66° C.; NMR (CDCl$_3$): 3.17 (m, 2), 2.98 (m, 1), 2.75 (dr,2, J=2.6, 12.0), 2.51 (s, 3), 2.01 (m, 2), 1.75 (m, 2); MS: m/z=196(M+1+28).

EXAMPLE 8

N-[2-(3,4-Dichlorophenyl)-4-[4-(4-ethoxycarbonylimidazol-2-yl)piperidino]butyl]-N-methylbenzamide Using a procedure similar to that described in Example 1 (alternative preparation), except using 4-(4-ethoxycarbonylimidazol-2-yl)piperidine, the title compound was obtained as a white solid; mp 96°–102° C.; NMR: 7.60–7.05 (m, 9), 4.30 (q,2, J=7.2), 3.78 (m, 2), 3.04, 2.77 (2s, 3, N—$CH_3$), 2.20–1.75 (m, 8), 1.34 (t, 3, J=7.2); MS: m/z=585[(M+1+28), $^{35}Cl$], m/z=559[(M+1), $^{37}Cl$], m/z=557 [(M+1), $^{35}Cl$]. Analysis for $C_{29}H_{34}Cl_2N_4O_3 \cdot 0.5$ $H_2O$: Calculated: C, 61.48; H, 6.23; N, 9.89; Found: C, 61.69; H, 6.35; N, 9.59.

The starting piperidine was prepared as follows.

a. 1-Benzyloxycarbonyl-4-cyanopiperidine

A solution of 4-cyanopiperidine (5.00 g) in 10% aqueous sodium carbonate solution (100 mL) was cooled to 0° C. and treated dropwise with benzyl chloroformate (9.30 g). The resulting mixture was warmed to room temperature and stirred for 16 hours. The biphasic mixture was extracted with ethyl acetate. The organic extracts were washed with water and brine, combined, dried, filtered and evaporated. The resulting oil was purified by chromatography, with ethyl acetate:hexane (gradient 1:4, 1:2) as eluent, to give the protected piperidine as a clear oil (9.64 g); MS: m/z=245 (M+1); NMR (CDCl$_3$): 7.35 (m, 5), 5.13 (s, 2), 3.71 (m, 2), 3.44 (m, 2), 2.81 (m, 1), 1.88–1.60 (m, 4).

b. 1-Benzyloxycarbonyl-4-piperidinecarboxamideoxime

A solution of hydroxylamine hydrochloride (0.340 g) in water (5 mL) was treated with sodium carbonate (0.26 g), followed by a solution of 1-benzyloxycarbonyl-4-cyanopiperidine (1.00 g) in ethanol (10 mL). The resulting mixture was heated under reflux for 3 hours. Additional hydroxylamine hydrochloride (0.340 g) and sodium carbonate (0.26 g) were added, and the mixture was heated at reflux for an additional 14 hours. The mixture was cooled and evaporated. The semisolid residue was suspended in dichloromethane, filtered and the solid product dried to afford the carboxamideoxime as a white solid (0.70 g); mp 111°–113° C.; NMR: 8.83 (s, 1), 7.35 (m, 5), 5.33 (broad s, 2), 5.07 (s, 2), 4.02 (broad d, 2, J=13.1), 2.80 (broad, 2), 2.19 (m, 1), 1.69 (broad d, 2, J=11.0), 1.55–1.42 (m, 2); MS: m/z=278(M+1).

c. 1-Benzyloxycarbonyl-4-piperidinecarboxamide O-((E/Z) -2-ethoxycarbonylvinyl)oxime A solution of 1-benzyloxycarbonyl-4-piperidinecarboxamide oxime (1.50 g) and ethyl propiolate (0.633 g) in methanol (15 mL) was heated under reflux for 16 hours, then was evaporated. The resulting amber syrup was purified by chromatography, eluting with dichloromethane:ethyl acetate (2:1), to afford the vinyl oxime as a mixture of isomers (1.68 g) ; NMR (CDCl$_3$): 7.80 (d, 0.3, J=12.2), 7.35 (m, 5), 7.20 (d, 0.7, J=7.0), 5.59 (d, 0.3, J=12.2), 5.12 (s, 2), 4.84 (d, 0.7, J=7.0), 4.24–4.08 (m, 4), 2.84 (broad, 2), 2.30 (m, 1), 1.83 (broad m, 2), 1.54 (broad m, 2), 1.25 (m, 3).

d. 1-Benzyloxycarbonyl-4-(4-ethoxycarbonylimidazol-2-yl) piperidine

A solution of 1-benzyloxycarbonyl-4-piperidinecarboxamide O-((E/Z)-2-ethoxycarbonylvinyl) oxime (1.68 g) in mesitylene (50 mL) was heated under reflux for 3 hours. The solvent was evaporated and the residue was purified by chromatography, with chloroform::methanol:ammonium hydroxide (970:30:1) as eluent, to yield the imidazole derivative as a tan foam (0.85 g); NMR: 7.75 (d, J=2.1), 7.35 (m, 5), 5.09 (s, 2), 4.21 (q, 2, J=7.1), 4.04 (broad d, 2, J=13.2), 2.91 (m, 3), 1.88 (m, 2), 1.62 (m, 2), 1.24 (t,3, J=7.1); MS: m/z=386(M+1+28).

e. 4-(4-Ethoxycarbonylimidazol-2-yl)piperidine

A solution of 1-benzyloxycarbonyl-4-(4-ethoxycarbonylimidazol-2-yl)piperidine (0.82 g) in ethanol (20 mL) was hydrogenated over 10% palladium on carbon (0.10 g) at a hydrogen pressure of 3.45 bar for 1 hour. The mixture was filtered through diatomaceous earth and the filter cake was washed with ethanol. The filtrate was evaporated to leave the piperidine derivative as a white foam (0.510 g); NMR: 7.65 (s, 1), 4.18 (q, 2, J=7.1), 2.99 (broad d, 2, J=12.2 H), 2.75 (m, 1), 2.55 (m, 2), 1.80 (broad d, 2, J=12.6), 1.57 (m, 2), 1.25 (t, 3, J=7.1); MS: m/z=252(M+1+28).

EXAMPLE 9

(S)-N-[2-(3,4-Dichlorophenyl)-4-[4-(3-pyridyl)piperidino] butyl]-N-methylbenzamide hydrochloride Using a procedure similar to that described in Example 1 (alternative procedure), 4-(3-pyridyl)piperidine was alkylated using (S)-N-[2-(3,4-dichlorophenyl)-4-oxobutyl]-N-methylbenzamide. Chromatography of the crude product, with dichloromethane:methanol (9:1) as the eluent, followed by conversion to the hydrochloride salt gave the title compound as a white solid (0.253 g); mp 70°–140° C. (dec); NMR: 1.8–2.4 (m, 6), 2.73 (s, 3), 2.8–3.2 (broad s, 5), 7.0–7.2 (m, 3), 7.4 (s, 4), 7.5–7.7 (m, 2), 7.9 (m, 1), 8.2 (broad s, 1), 8.7 (d, 2 J=5); MS: m/z=496(M+1). Analysis for $C_{28}H_{31}ClN_3O \cdot 2.2$ HCl·3 $H_2O$: Calculated: C, 53.94; H, 6.31; N, 6.74; Found: C, 53.53; H, 6.16; N, 6.65.

The (S)-N-[2-(3,4-dichlorophenyl)-4-oxobutyl]-N-methylbenzamide was prepared as follows:

a. 2- (3,4-Dichlorophenyl) -4-hydroxybutylamine

To a mechanically stirred solution of 2-(3,4-dichlorophenyl)-4-(tetrahydropyran-2-yloxy)butylamine (550 g) in methanol (3300 mL) was added in one portion 6.0N hydrochloric acid (352 mL), resulting in a slight exotherm. After being stirred for 3 hours, the reaction mixture was evaporated, and the residue was diluted with water to 3 L volume. This solution was extracted with ether (2 times 500 mL), basified with sodium hydroxide pellets (100 g), and extracted with ethyl acetate (4 times 500 mL). The combined ethyl acetate extracts were washed (800 mL saturated sodium chloride), dried, and evaporated to give the alcohol as an amber oil (367 g) that solidified under high vacuum; NMR: 7.39 (d, 1, J=8.2), 7.28 (d, 1, J=2.0), 7.04 (dd, 1, J=8.2, 2.0), 3.65 (m, 1), 3.50 (m, 1), 2.90 (m, 2), 2.71 (m, 1), 2.25 (m, 2), 1.86 (m, 2).

b. (S)-2-(3,4-Dichlorophenyl)-4-hydroxybutylamine

To a mechanically stirred solution of D-tartaric acid (222 g) in methanol (4 L) at reflux was added the above amino alcohol (342 g) in warm methanol (2 L) in one portion and washed down with additional methanol (1 L). The mixture was heated to reflux. Crystals began to form before attaining the boiling point. After 1.5 hours at reflux, the solution was gradually cooled to room temperature and stirred for 3 days. The first crop of tartrate salt was collected by suction filtration and dried in a vacuum oven at 60° C. to give the product (232 g). This material was taken up in methanol (13.5 L) at boiling, and held at reflux for 1 hour allowing 1 L of methanol to distil off. The mixture was allowed to cool gradually to room temperature and stirred for 4 days. The first crop of crystals was collected by suction filtration and dried to give a solid (178.8 g). The methanol filtrate was evaporated to approximately 3 L volume. The resulting suspension was heated back to reflux to give a clear solution that was allowed to cool gradually to room temperature with stirring. A second crop of crystals (43.8 g) was collected. The combined crops of resolved amino alcohol tartrates (222.6 g) were taken up in 1.0N sodium hydroxide (1.5 L) and extracted with dichloromethane (4 times 500 mL). The combined organic extracts were washed with brine, dried, and evaporated to give the optically enriched amino alcohol as an off-white solid (135.4 g); mp 80°–2° C.; NMR ($CD_3OD$): 7.47 (d, 1, J=8.3), 7.42 (d, 1, J=2.1), 7.17 (dd, 1, J=8.2, 2.1), 3.47 (m, 1), 3.34 (m, 1), 2.83 (m, 3), 1.92 (m, 1), 1.74 (m, 1); MS: m/z=324(M+1).

c. Ethyl (S)-N-[2-(3,4-dichlorophenyl)-4-hydroxybutyl] carbamate

Ethyl chloroformate (25.5 g) was added dropwise over 20 minutes to a mechanically stirred solution of the above amino alcohol (50.0 g) and triethylamine (24.9 g) in dichloromethane (600 mL) cooled to -30° C. The internal temperature was maintained at -20° to -25° C. during the addition. The reaction mixture was then allowed to warm gradually to room temperature over a 4 hour period, and washed (1 N hydrochloric acid, saturated aqueous sodium bicarbonate, and saturated aqueous sodium chloride). The separated dichloromethane phase was dried and evaporated to give the carbamate as a yellow oil (65.3 g); NMR ($CD_3OD$): 7.44 (d, 1, J=8.3), 7.38 (d, 1, J=2.1), 7.15 (dd, 1, J=8.3, 2.1), 3.99 (q, 2, J=7.1), 3.45 (m, 1), 3.29 (m, 3), 2.97 (m, 1), 1.92 (m, 1), 1.75 (m, 1), 1.16 (t,3, J=7.1); MS: m/z=306(M+1).

d. (S)-N-[2-(3,4-dichlorophenyl)-4-hydroxybutyl]-N-methylamine

The above carbamate (65.3 g) in tetrahydrofuran (500 mL) was added dropwise over 30 minutes to a mechanically stirred suspension of lithium aluminum hydride (16.0 g) in tetrahydrofuran (200 mL). The internal temperature rose to 45° C. during the addition. The reaction mixture was heated at reflux for 1 hour, then cooled to room temperature and stirred overnight. The mixture was cooled in an ice bath, and saturated aqueous sodium sulfate (50 mL) was added dropwise over 45 minutes. After an additional hour of stirring, solid anhydrous sodium sulfate (50 g) was added. After being stirred for 30 minutes, the mixture was filtered through diatomaceous earth, and the filtrate was evaporated to give the methylamine as a yellow oil (52.9 g); NMR: 7.37 (d, 1, J=8.2), 7.27 (d, 1, J=2.0), 7.01 (dd, 1, J=8.2, 2.1), 3.69 (m, 1), 3.53 (m, 1), 3.40 (m, 2), 2.76 (m, 3), 2.45 (m, 3), 1.89 (m, 2); MS: m/z=248(M+1).

e. (S)-N-[2-(3,4-Dichlorophenyl)-4-hydroxybutyl]-N-methylbenzamide

Benzoyl chloride (31.5 g) in dichloromethane (200 mL) was added dropwise over 45 minutes to a mechanically stirred solution of the above amine (52.9 g) and triethylamine (54.0 g) in dichloromethane (1 L) cooled in an ice bath to maintain an internal temperature of 5°–8° C. The reaction mixture was allowed to stir for 3 hours at room temperature, and then washed (1N hydrochloric acid, brine). The separated dichloromethane layer was evaporated to give a yellow oil which was chromatographed, with dichloromethane:methanol (gradient 100:0, 95:5) as eluent, to give the benzamide as a white solid (65.6 g); mp 123°–5° C.; MS: m/z=352(M+1); [a]$_D$=–18.3° (c=2.46, CH$_3$OH).

f. (S)-N-[2-(3,4-Dichlorophenyl)-4-oxobutyl]-N-methylbenzamide

The above alcohol (12.9 g) in dichloromethane (150 mL) was cannulated into a solution of Dess-Martin periodinane (18.6 g) and tert-butanol (4.5 mL) in dichloromethane (150 mL). After being stirred for 5 minutes, the reaction mixture was diluted with ether (600 mL) and a solution of sodium bicarbonate (19.7 g) and sodium thiosulfate pentahydrate (64.5 g) in water (825 mL). The biphasic system was vigorously stirred until both layers became clear (approximately 30 minutes). The separated organic layer was washed (saturated aqueous sodium bicarbonate), dried, and evaporated. The crude material was chromatographed, with dichloromethane:ether (1:1) as eluent, to give the aldehyde as a white solid (9.7 g) by precipitation and filtration from ether; MS: m/z=350(M+1).

The intermediate 4-(3-pyridyl)piperidine was prepared as follows:

g. 1-Benzyloxycarbonyl-1,2,3,6-tetrahydropyridine

A solution of 1,2,3,6-tetrahydropyridine (5.0 g) in dichloromethane (200 mL) was cooled to 0° C. and treated with triethylamine (10.1 mL) followed by benzylchloroformate (10.3 mL). The reaction mixture was stirred for 1 hour at 0° C., diluted with dichloromethane, washed (dilute hydrochloric acid, sodium bicarbonate solution), dried and evaporated. The crude product was distilled to give the N-protected derivative (11.01 g); bp 160°–165° C. (26.7 Pa); NMR (CDCl$_3$): 2.15 (broad, 2), 3.5 (t,2, J=6), 3.96 (m, 2), 5.15 (s, 2), 5.8 (2 broad peaks, 2), 7.4(m, 5); MS: m/z=218(M+1).

h. 1-Benzyloxycarbonyl-4-(3-pyridyl)-1,2,3,4-tetrahydropyridine

A solution of 1-benzyloxycarbonyl-1,2,3,4-tetrahydropyridine (8.69 g) in dimethylsulfoxide (50 mL) was treated with 3-bromopyridine (6.32 g), triethylamine (5.6 mL) and palladium(II) acetate (0.499 g). The reaction mixture was heated to 100° C. for 16 hours, cooled to the room temperature, diluted with water, and extracted with ether. The organic layer was washed with water; the combined organic layers were dried and evaporated to produce the crude product. This material was distilled under reduced pressure and the volatile material distilling at 120° C. (66.7 Pa) was removed. The remaining residue was chromatographed, with hexane:ethyl acetate (1:1) as eluent, to afford the coupled product (0.714 g); NMR (CDCl$_3$): 1.7 (broad s, 2), 2.16 (broad m, 1), 3.5–3.7 (m, 2), 4.9–5.1 (d of m, 2), 5.2 (m, 2), 7.0–7.5 (m, 8), 8.5 (m, 2); MS: m/z=295 (M+1).

i. 4-(3-Pyridyl)piperidine

A solution of 1-benzyloxycarbonyl-4-(3-pyridyl)-1,2,3,4-tetrahydropyridine (0.714 in ethanol (50 mL) was treated with 10% palladium on carbon (0.1 g) and hydrogenated under a hydrogen atmosphere at room temperature and 3.44 bar for 16 hours. The reaction mixture was filtered through diatomaceous earth to remove the catalyst, and the resulting filtrate was evaporated to afford the piperidine (0.393 g); NMR (CDCl$_3$): 1.7 (m, 4), 2.8 (m, 4), 3.2 (m, 2), 7.3 (m, 1), 7.5 (m, 1), 8.5 (m, 2); MS: m/z=162(M+1).

EXAMPLE 10

N-[2-(3,4-Dichlorophenyl)-4-[(3R*,4R*)-3-hydroxy-4-phenylpiperidino]butyl-N-methylbenzamide hydrochloride A solution of (3R*,4R*)-3-hydroxy-4-phenylpiperidine (0.16 g) in methanol (5 mL) was treated with acetic acid (6 drops), cooled to 0° C. and treated with a solution of N-[2-(3,4-dichlorophenyl)-4-oxobutyl]-N-methylbenzamide (0.28 g) in methanol (5 mL) followed by sodium cyanoborohydride (0.08 g). After stirring for 16 hours at room temperature, the reaction mixture was evaporated before being dissolved in dichloromethane. That solution was washed (sodium carbonate, sodium chloride solution), dried, and evaporated to afford the crude product. This product was converted to the hydrochloride salt by dissolving in dichloromethane and treating with anhydrous hydrogen chloride in ether. Upon dilution with ether and stirring for 2 hours, the solid was collected to afford the title compound as a white solid (0.36 g); mp 105°–141° C.; MS: m/z=511(M+1); NMR: 1.8–2.2 (m, 4), 2.5 (s, 3), 4.1 (br, 1), 6.98–7.70 (m, 13). Analysis for C$_{29}$H$_{32}$Cl$_2$N$_2$O$_2$·HCl·H$_2$O: Calculated: C, 61.54; H, 6.23; N, 4.95; Found: C, 61.63; H, 6.24; N, 5.00.

The intermediate (3R*,4R*)-3-hydroxy-4-phenylpiperidine was prepared as follows:

a. 1-Benzyloxycarbonyl-4-hydroxy-4-phenylpiperidine

A suspension of 4-hydroxy-4-phenylpiperidine (10 g) in dichloromethane (90 mL) was treated with triethylamine (5.71 g) and cooled to –6° C. This reaction mixture was treated with benzyl chloroformate (9.62 g) in 1 mL portions, stirred for 3 hours and diluted with chloroform (100 mL), washed with 1N HCl, and extracted with chloroform. The organic layers were washed with brine, dried and evaporated to afford the crude material. Chromatography, with methanol:dichloromethane (1:30) as the eluent, gave the benzyloxycarbonylpiperidine (9.4 g); MS: m/z=312(M+1); NMR: 1.6 (d, 2, J=10), 1.77–1.89 (m, 2), 3.91 (m, 2), 5.09 (s,2), 7.18–7.48 (m, 10).

b. 1-Benzyloxycarbonyl-4-phenyl-1,2,3,6-tetrahydropyridine

A solution of 1-benzyloxycarbonyl-4-hydroxy-4-phenylpiperidine (8.89 g) in concentrated hydrochloric acid (60 mL) was heated to 100° C. for 15 minutes. After cooling to the room temperature, the reaction mixture was neutralized with a sodium carbonate solution (77 g in 250 mL water) and extracted with dichloromethane. The organic layers were washed with brine, dried over anhydrous potassium carbonate and evaporated to afford the crude product. Chromatography, with methanol:dichloromethane (1:99) as eluent, afforded the tetrahydropyridine as a viscous liquid (6.3 g); MS: m/z=294(M+1); NMR: 2.07–2.36 (m, 2), 4.0 (m, 2), 5.12 (two peaks 2), 7.26–7.69 (m, 10).

c. (3R*,4R*)-1-Benzyloxycarbonyl-3-hydroxy-4-phenylpiperidine

A solution of 1-benzyloxycarbonyl-4-phenyl-1,2,3,6-tetrahydropyridine (1.0 g) in tetrahydrofuran (20 mL) was cooled to 0° C. and treated with borane:tetrahydrofuran (3.75 mL of 1M solution in tetrahydrofuran). The reaction mixture was stirred for 16 hours at ambient temperature, diluted with methanol (50 mL), and treated with 3N sodium hydroxide (1.25 mL). The resulting reaction mixture was cooled to 0° C. and treated with 30% hydrogen peroxide solution (0.58 mL). After refluxing for 2 hours, the reaction mixture was cooled to room temperature, diluted with water and extracted with ethyl acetate. The combined organic layers were washed with water and the aqueous layer was extracted with ethyl acetate. Combined organic layers were dried and evaporated to afford the crude product (0.88 g). Chromatography, eluting with hexane:ethyl acetate (3:1) afforded the trans-1-benzyloxycarbonyl-3-hydroxy-4-phenylpiperidine (0.31 g); MS: m/z=312(M+1); NMR: 1.54–1.72 (m, 2), 3.51 (m, 1), 4.02 (m, 1), 4.17 (m, 1), 4.86 (d, 1, J=5), 5.1 (s, 2), 7.17–7.37 (m, 10).

d. (3R*,4R*)-3-Hydroxy-4-phenylpiperidine

A solution of (3R*,4R*)-1-benzyloxycarbonyl-3-hydroxy-4-phenylpiperidine (0.3 g) in methanol (30 mL) was treated with 10% palladium on carbon (0.03 g) and hydrogenated at atmospheric pressure for 2 hours. The reaction mixture was filtered through diatomaceous earth and evaporated to afford (3R*,4R*)-3-hydroxy-4-phenylpiperidine (0.2 g); MS: m/z=178(M+1); NMR: 1.44–1.58 (m, 2), 2.23–2.5 (m, 9), 4.36 (broad, 1), 7.13–7.29 (m, 5).

EXAMPLE 11

N-[(2R)-(3,4-Dichlorophenyl)-4-[(3S,4S)-3-hydroxy-4-phenylpiperidino]butyl]-N-methylbenzamide hydrochloride Using a procedure similar to that described in Example 10, but using (3S,4S)-3-hydroxy-4-phenylpiperidine (approximately 80% S,S-isomer) and (R)-N-[2-(3,4-dichlorophenyl)-4-oxobutyl]-N-methylbenzamide, the title compound (approximately 80% S,S-isomer) was prepared; MS: m/z=511(M+1); NMR (DMSO-$d_6$+CF$_3$COOD): 1.9–2.2 (br, 4), 2.76 (s, 3), 3.74 (br, 1), 3.98(br, 1), 7.02–7.72 (m, 13). Analysis for $C_{29}H_{32}Cl_2N_2O_2 \cdot HCl \cdot H_2O$: Calculated: C, 61.54, H, 6.23, N, 4.95; Found: C, 61.75; H, 6.20, N, 4.89.

The intermediate (3S,4S)-3-hydroxy-4-phenylpiperidine (approximately 80% S,S-isomer) was prepared as follows:

a. (3S,4S)-1-Benzyloxycarbonyl-3-hydroxy-4-phenylpiperidine

A solution of N,N'-bis(monoisopinocamphenylborane)-N,N,N',N'-tetra-methylethylenediamine [R-Alpine-Boramine (trademark)] (1.0 g) in 20 mL of tetrahydrofuran was treated with boron trifluoride etherate (0.59 mL) and stirred at the room temperature for 1.5 hours. The stirring was stopped and the precipitate formed was allowed to settle. The supernate was withdrawn with a syringe and added to 1-benzyloxycarbonyl-4-phenyl-1,2,3,6-tetrahydropyridine (1.41 g). The resulting reaction mixture was allowed to stand at −25° C. for 16 hours. At the end of this period, the reaction mixture was warmed to room temperature, stirred for 16 hours, treated with methanol (0.49 mL) followed by 3N sodium hydroxide solution (1.76 mL) and finally 30% hydrogen peroxide (1.47 mL). The resulting reaction mixture was heated to 60° C. for 1 hour, cooled to the room temperature, diluted with 100 mL ethyl acetate and water. The aqueous layer was separated and extracted with ethyl acetate. The organic layers were dried and evaporated to afford the crude product. Chromatography, with ethyl acetate:hexane (1:4) as eluent, afforded the product (0.32 g); MS: m/z=312(M+1); NMR (DMSO-$d_6$+CF$_3$COOD): 1.62–1.73 (m, 2), 2.56 (br, 1), 2.55 (br, 1), 3.57 (m, 1), 4.09 (d, 1, J=13), 4.25 (d,d, 1, J=12, J=4), 5.13 (s, 2), 7.16–7.41 (m, 10). Analysis of this material by high pressure liquid chromatography on a column of 10 µ particles of a silica gel supported cellulose derivative in which the cellulose hydroxy groups have been derivatized as N-3,5-dimethylbenzyl carbamates (Chiralcel OD, obtained from J. T. Baker Inc.) [Chiralcel is trademark of Daicel Chemical Industries], using ethanol:hexane (1:7) as eluent, showed it to be 81% of one of the two possible optical isomers. This material was used in the next step without further purification or characterization.

b. (3S,4S)-3-hydroxy-4-phenylpiperidine (3S,4S)-1-Benzyloxycarbonyl-3-hydroxy-4-phenylpiperidine (0.3 g) was subjected to a procedure similar to that described in Example 10.d. to give the piperidine (0.18 g); MS: m/z=178(M+1). This material was used in the next step without further characterization or purification.

The (R)-N-[2-(3,4-dichlorophenyl)-4-oxobutyl]-N-methylbenzamide was obtained by oxidation of (R)-N-[2-(3,4-dichlorophenyl)-4-hydroxybutyl]-N-methylbenzamide which was obtained by resolution of N-[2-(3,4-dichlorophenyl)-4-hydroxybutyl]-N-methylbenzamide by preparative high pressure liquid chromatography using a 50mm×50 cm column of 10 µ particles of a silica gel supported cellulose derivative in which the cellulose hydroxy groups have been derivatized as 4-methylbenzoates (Chiralcel OJ obtained from J. T. Baker Inc.) [Chiralcel (trademark, see above)], eluting with hexane:ethanol (3:1) at a flow rate of 54 mL/minute and uv detection at 230 nm.

EXAMPLE 12

N-[(2S)-(3,4-Dichlorophenyl)-4-[(3S,4S)-3-hydroxy-4-phenylpiperidino]butyl]-N-methylbenzamide hydrochloride Using a procedure similar to that described in Example 10, but using (3S,4S)-3-hydroxy-4-phenylpiperidine (approximately 80% S,S-isomer) and (S)-N-[2-(3,4-dichlorophenyl)-4-oxobutyl]-N-methylbenzamide, the title compound (approximately 80% S,S-isomer) was prepared; MS: m/z=511(M+1); NMR (DMSO-$d_6$+CF$_3$COOD): 1.8–2.4 (m, 4), 2.74 (s, 3), 3.4–3.7 (m, 3), 6.91–7.68 (m, 8), 9.55 (two peaks, 1). Analysis for $C_{29}H_{32}Cl_2N_2O_2 \cdot HCl \cdot H_2O$: Calculated: C, 61.54, H, 6.23, N, 4.95; Found: C, 61.65; H, 6.13, N, 4.89.

The (S)-N-[2-(3,4-dichlorophenyl)-4-oxobutyl]-N-methylbenzamide was obtained by oxidation of (S)-N-[2-(3,4-dichlorophenyl)-4-hydroxybutyl]-N-methylbenzamide which was obtained by resolution of N-[2-(3,4-dichlorophenyl)-4-hydroxybutyl]-N-methylbenzamide by preparative high pressure liquid chromatography as described above after Example 11.b.

EXAMPLE 13

N-[2-(3,4-Dichlorophenyl)-4-[4-(2-methylthiophenyl)-piperidino]butyl]-N-methylbenzamide hydrochloride Using a procedure similar to that described in Example 1 (alternative preparation), except using 4-(2-methylthiophenyl)piperidine, the title compound was prepared. Chromatography with dichloromethane:methanol followed by conversion to the hydrochloride salt gave a white solid; mp 98°–118° C.; MS: 541; NMR (CD$_3$OD): 1.9–2.3 (m, 6), 2.4 (s, 1), 2.7–2.8 (two s, 3), 2.9–3.4 (br, 6), 3.5–3.9 (m, 4), 7.0 (m, 4), 7.3–7.6 (m, 7), 7.5–7.6 (m, 2). Analysis for $C_{30}H_{34}Cl_2NO_2S \cdot 1.0 \text{ HCl} \cdot 1.0 \text{ H}_2O$: Calculated: C, 60.45; H, 6.26; N, 4.70; Found: C, 60.43; H, 5.91; N, 4.63.

The intermediate 4-(2-methylthiophenyl)piperidine was prepared as follows:

a. 1-Benzyloxycarbonyl-4-hydroxy-4-(2-methylthiophenyl) piperidine

A solution of 2-bromothioanisole (1.05 g) in 20 mL of anhydrous tetrahydrofuran was cooled to −78° C. and treated with 2 mL of 2.5M hexane solution of n-butyl lithium. After the addition was complete the reaction mixture was stirred for 30 minutes and then treated with a solution of N-benzyloxycarbonyl-4-oxopiperidine (1.17 g) in 1 mL of tetrahydrofuran. After stirring at −78° C. for 30 minutes the reaction mixture was allowed to warm to 6° C. and treated with 10 mL of water. Upon extracting with ethyl acetate, drying and evaporation, the organic layer afforded the crude product. This material was purified by chromatography; elution with 6:4 hexane:ethyl acetate afforded the named material (0.27 g); MS: 358; NMR: 1.9–2.1 (b, 4), 2.5 (s, 3), 3.4 (b, 2), 4.1b (b, 2), 5.1 (s, 2), 7.1–7.5 (m, 9).

b. 1-Benzyloxycarbonyl-4-(2-methylthiophenyl)piperidine

A solution of 1-benzyloxycarbonyl-4-hydroxy-4-(2-methylthiophenyl)piperidine (2.89 g) in dichloromethane (80 mL) was treated with 6.2 mL of trifluoroacetic acid followed by 25.7 mL of triethylsilane and stirred for 16 hours. At the end of this period, the volatile material was distilled under reduced pressure and the resulting residue was chromatographed. Elution with 3:1 hexane:ethyl acetate afforded the named material (2.02 g); MS: 342(M+1); NMR: 1.5–1.6 (br, 2), 1.8–1.9 (m, 2), 2.45 (s, 3), 2.8–2.9 (m, 2), 3.1–3.2 (m, 1), 4.3 (br, 2), 5.1 (s, 2), 7.1–7.2 (m, 2), 7.2–7.3 (m, 2), 7.3–7.4 (m, 5).

c. 4-(2-Methylthiophenyl)piperidine

A mixture of 1-benzyloxycarbonyl-4-(2-methylthiophenyl)piperidine (0.34 g) and thioanisole (0.58 mL) was treated with trifluoroacetic acid (5 mL) and the mixture was heated to 60° C. for 30 minutes. At the end of this period, the reaction mixture was evaporated and diluted with ether. Extraction with water, neutralization of the aqueous layer with sodium bicarbonate and extraction with ethyl acetate afforded the crude product. This material was purified by column chromatography; elution with 19:1 dichloromethane:methanol containing 5% triethylamine afforded the named product (0.13 g); MS: 208 (M+1); NMR: 1.4–1.8 (q, d, $J_1$=25, $J_2$=12, 2), 1.8–1.9 (m, 2), 2.46 (s, 3), 2.8–2.9 (d, t, $J_1$=12, $J_2$=2.7, 2), 3.1–3.2 (m, 1), 3.3 (br, 2), 4.0 (br, 1), 7.1–7.3 (m, 4).

EXAMPLE 14

(S)-N-[2-(3,4-Dichlorophenyl)-4-[4-(2-methylsulfinylphenyl)piperidino]butyl]-N-methylbenzamide hydrochloride Using a procedure similar to that described in Example 1 (alternative preparation), except using 4-(2-methylsulfinylphenyl)piperidine and (S)-N-[2-(3,4-dichlorophenyl)-4-oxobutyl]-N-methyl-benzamide, the title compound was prepared. Chromatography with dichloromethane:methanol followed by conversion to the hydrochloride salt gave a white solid; mp 71°–144° C.; MS: 557; NMR (CD$_3$OD): 1.9–2.3 (m, 6), 2.4 (s, 1), 2.7–2.8 (two s, 3), 2.9–3.4 (br, 6), 3.5–3.9 (m, 4), 7.0 (m, 4), 7.3–7.6 (m, 7), 7.5–7.6 (m, 2). Analysis for $C_{30}H_{34}Cl_2NO_2S \cdot 1.0$ HCl$\cdot 1.0$ H$_2$O: Calculated: C, 60.45; H, 6.26; N, 4.70; Found: C, 60.43; H, 5.91; N, 4.63.

The intermediate 4-(2-methylsulfinylphenyl)piperidine was prepared as follows:

a. 1-Benzyloxycarbonyl-4-(2-methylsulfinylphenyl)piperidine

A solution of 1-benzyloxycarbonyl-4-(2-methylthiophenyl)piperidine (prepared as described in Example 13) (3.27 g) in 60 mL of chloroform was cooled in ice and treated with trans-2-(phenylsulfonyl)-3-phenyloxaziridine (2.5 g) (Vishwakarma et al., Org. Syn, 66, 203–210). The reaction mixture was allowed to warm to room temperature over 1 hour and the solvent was evaporated. The residue was chromatographed; elution with ethyl acetate:methanol (9:1) afforded the named compound (1.71 g); MS: 358; NMR: 1.6–1.9 (m, 4), 2.7 (s, 3), 2.8–3.0 (br, 3), 4.4–4.5 (br, 2), 5.2 (s, 2), 7.2–7.3 (m, 1), 7.3–7.4 (m, 5), 7.4–7.5 (m, 2), 8.0 (m, 1).

b. 4-(2-Methylsulfinylphenyl)piperidine

A solution of 1-benzyloxycarbonyl-4-(2-methylsulfinylphenyl)piperidine (1.66 g) in 8 mL of trifluoroacetic acid was heated to reflux for 45 minutes. At the end of this period, the reaction mixture was evaporated and the residue was treated with toluene. Upon evaporating the solvent, the residue was treated with an additional portion of toluene and the process was repeated. The final residue was dried under reduced pressure and purified by chromatography; elution with dichloromethane:methanol:triethylamine (19:1:1) afforded the named product (0.87 g); MS: 224; NMR: 1.6–2.4 (m, 4), 2.7 (two peaks, 3), 2.9–3.2 (m, 3), 3.3–3.5 (m, 2), 5.3–5.7 (br, 1), 7.4–7.5 (m, 3), 7.9–8.0 (m, 1).

EXAMPLE 15

(S)-N-[2-(3,4-Dichlorophenyl)-4-[4-(4-methylthiophenyl)piperidino]butyl]-N-methylbenzamide hydrochloride Using a procedure similar to that described in Example 1 (alternative preparation), except using 4-(4-methylthiophenyl)piperidine and (S)-N-[2-(3,4-dichlorophenyl)-4-oxobutyl]-N-methylbenzamide, the title compound was prepared. Chromatography with dichloromethane:methanol followed by conversion to the hydrochloride salt gave a white solid; mp 73–92(dec) °C.; MS: 541; NMR (CD$_3$OD): 1.8–2.2 (m, 6), 2.4 (s, 1), 2.7 (s, 3), 2.6–3.2 (m, 6), 3.4–3.8 (m, 4), 6.9 (d, J=7, 1), 7.1–7.2 (m, 6), 7.3 (m, 5), 7.5(m, 1). Analysis for $C_{30}H_{34}Cl_2NO_2S \cdot 1.0$HCl$\cdot 1.0$ H$_2$O: Calculated: C, 60.45; H, 6.26; N, 4.70; Found: C, 60.23; H, 5.85; N, 4.70.

The intermediate 4-(4-methylthiophenyl)piperidine was prepared as follows.

a. 1-Benzyloxycarbonyl-4-hydroxy-4-(4-methylthiophenyl)piperidine

Using a procedure similar to that described in Example 13.a., except using 4-bromothioanisole, the named compound was prepared; MS: 358; NMR: 1.7 (d, J=13, 2), 2.0 (br, 2), 2.5–(s, 3), 3.2 (br, 2), 4.1 (br, 2), 5.1 (s, 2), 7.2–7.4 (m, 9).

b. 1-Benzyloxycarbonyl-4-(4-methylthiophenyl)piperidine

Using a procedure similar to that described in Example 13.b., except using 1-benzyloxycarbonyl-4-hydroxy-4-(4-methylthiophenyl)piperidine, the title compound was obtained as an impure mixture which exhibited the expected MS: 342; NMR: 1.6 (br, 2), 1.8 (br, 2), 2.6–(m, 1), 2.9–3.0 (br, 2), 4.4 (br, 2), 7.1–7.4 (m, 4). Additional peaks corresponding to an impurity were also seen. This material was used further without purification.

c. 4-(4-Methylthiophenyl)piperidine

Using a procedure similar to that described in Example 13.c., except using 1-benzyloxycarbonyl-4-(4-methylthiophenyl)piperidine, the named compound was prepared; MS: 208; NMR: 1.7–1.8 (d, q, $J_1$=12, $J_2$=4, 2), 1.8 (d, J=10, 2), 2.46 (s, 3), 2.5–2.6 (m, 1), 2.7–2.8 (m, 3), 3.2 (d, J=12, 2), 7.1–7.2 (m, 2).

EXAMPLE 16

(S)-N-[2-(3,4-Dichlorophenyl)-4-[4-(4-methylsulfinylphenyl)piperidino]butyl]-N-methylbenzamide hydrochloride Using a procedure similar to that described in Example 1 (alternative preparation), except using 4-(4-methylsulfinylphenyl)piperidine and (S)-N-[2-(3,4-dichlorophenyl)-4-oxobutyl]-N-methylbenzamide, the title compound was prepared. Chromatography with dichloromethane:methanol followed by conversion to the hydrochloride salt gave a white solid; mp 94°–125° C.; MS: 557; NMR (CD$_3$OD): 1.8–2.3 (m, 6), 2.8 (s, 6), 2.8–3.3 (br, 6), 3.4–3.9 (m, 4), 7.9–7.7 (m, 12). Analysis for $C_{30}H_{34}Cl_2NO_2S \cdot 1.0$ HCl$\cdot 1.5$ H$_2$O: Calculated: C, 58.02; H, 6.17; N, 4.51; Found: C, 57.74; H, 6.00; N, 5.01.

The intermediate 4-(4-methylsulfinylphenyl)piperidine was prepared as follows.

a. 1-Benzyloxycarbonyl-4-(4-methylsulfinylphenyl)piperidine

Using a procedure similar to that described in Example 14.a., except using 4-(4-methylthiophenyl)piperidine, the named compound was prepared. Chromatography with ethyl acetate:methanol gave a white solid; MS: 358; NMR: 1.6–1.7 (m, 2), 1.86 (d, J=12, 2), 2.7–2.8 (m, 4), 2.9 (br, 2), 4.3 (br, 2), 5.2 (s, 2), 7.2–7.7 (m, 9).

b. 4-(4-Methylsulfinylphenyl)piperidine

Using a procedure similar to that described in Example 14.b., except using 1-benzyloxycarbonyl-4-(4-methylsulfinylphenyl)piperidine, the named compound was prepared; MS: 224; NMR: 1.6–1.8 (d, q, $J_1$=12, $J_2$=4, 2), 1.9 (d, J=12, 2), 2.5 (s, 1), 2.6–2.8 (m, 6), 3.25 (d, J=12, 2), 7.4 (d, J=8, 2), 7.6 (t, d, $J_1$=8, $J_2$=2, 2).

EXAMPLE 17

(S)-N-[2-(3,4-Dichlorophenyl)-4-[4-(2-hydroxyphenyl) piperidino]butyl]-N-methylbenzamide hydrochloride Using a procedure similar to that described in Example 1 (alternative preparation), except using 4-(2-hydroxyphenyl) piperidine and (S)-N-[2-(3,4-dichlorophenyl)-4-oxobutyl]-N-methylbenzamide, the title compound was prepared. Chromatography, eluting with dichloromethane:methanol, followed by conversion to the hydrochloride salt gave a white solid; mp 205°–210° C.; MS: 511; NMR (CD$_3$OD): 1.7–2.3 (m, 6), 2.7 (s, 1), 2.8–3.1 (m, 6), 3.2–3.8 (m, 5), 6.7–6.8 (m, 2), 7.0 (t, J=7, 3), 7.2 (br, 2), 7.4 (br, 2), 7.4 (br, 4), 7.5–7.7 (m, 2), 9.5 (s, 10), 10.5 (s, 1). Analysis for $C_{29}H_{32}Cl_2N_2O_2$·1.0 HCl·0.75 H$_2$O: Calculated: C, 62.04; H, 6.19; N, 4.99; Found: C, 62.24; H, 6.15; N, 5.08.

The intermediate 4-(2-hydroxyphenyl)piperidine was prepared as follows:

a. Benzyl 2-bromophenyl ether

A suspension of potassium carbonate (15.2 g) in 200 mL of dimethylformamide containing 2-bromophenol (14.9 g) was treated with benzyl bromide (17.1 g). After stirring for 3 hours, the reaction mixture was diluted with water and extracted with hexane. The hexane layer was washed with water, 1N sodium hydroxide solution and brine, dried over sodium sulfate and evaporated to afford the crude product as an oil. This material was purified by fractional distillation under reduced pressure to afford the pure ether (16.52 g); bp 110°–145° C. (133 Pa); MS: 269; NMR: 5.2 (s, 2), 6.8–6.9 (d, t, $J_1$=7.5, $J_2$=1.3, 1), 6.9–7.0 (d,d, $J_1$=8, $J_2$=1.3, 1), 7.2–7.4 (m, 7), 7.5 (m, 2), 7.5–7.6 (d,d, $J_1$=8, $J_2$=1.6, 1).

b. 1-Benzyloxycarbonyl-4-hydroxy-4-(2-benzyloxyphenyl) piperidine

A solution of benzyl 2-bromophenyl ether (3.5 g) in 50 mL of anhydrous tetrahydrofuran was cooled to –78° C. and treated with 5.3 mL of 2.5M n-butyl lithium solution in hexane followed by a solution of 1-benzyloxycarbonyl-4-oxopiperidine (3.1 g) in 3 mL of anhydrous tetrahydrofuran. After stirring at –78° C. for 1 hour the reaction mixture was warmed to 0° C., stirred for 2 hours and then allowed to warm to room temperature. Addition of water, extraction with ethyl acetate, drying the organic layer over magnesium sulfate and evaporation afforded the crude product. This material was purified by chromatography: elution with hexane:isopropanol (9:1) afforded the named compound (2.86 g) as a solid; MS: 418; NMR: 2.0 (br, 4), 3.3–3.4 (br, 2), 3.9–4.1 (s, 3), 5.1 (two s, 4), 6.9–7.0 (m, 2), 7.2–7.3 (m, 2), 7.3–7.4 (m, 10).

c. 1-Benzyloxycarbonyl-4-(2-benzyloxyphenyl)piperidine

Using a procedure similar to that described in Example 13.b., except using 1-benzyloxycarbonyl-4-hydroxy-4-(2-benzyloxyphenyl)piperidine, the named compound was prepared. This material was purified by chromatography; elution with 2:1 hexane:ethyl acetate afforded the named compound containing an impurity; MS: 402; NMR: 1.5–1.7 (m, 2), 1.8 (d, J=12, 2), 2.9 (br, 2), 3.2 (m, 1), 4.3 (br, 2), 5.0–5.2 (m, 4), 6.9–7.0 (m, 2), 7.1–7.2 (m, 2), 7.3–7.4 (m, 10). Additional NMR signals corresponding to the impurity were also seen. This material was used in the next step without further purification.

d. 4-(2-Hydroxyphenyl)piperidine

A solution of 1-benzyloxycarbonyl-4-(2-benzyloxyphenyl)piperidine (1.22 g) in 20 mL of tetrahydrofuran was treated with 10% palladium on carbon catalyst (0.12 g) and hydrogenated at the atmospheric pressure for 16 hours. Upon filtration and evaporation of the filtrate the named product was obtained (0.36 g) as a solid; MS: 178; NMR: 1.8–1.9 (m, 4), 2.7–2.8 (m, 2), 3.0 (m, 1), 3.2 (d, J=12, 2), 5.4 (br, 2), 6.7 (d, J=8, 1), 6.8 (t, J=7, 1), 7.0–7.1 (m, 1), 7.1 (d, J=7, 2).

EXAMPLE 18

(S)-N-[2-(3,4-Dichlorophenyl)-4-[4-(3-hydroxyphenyl) piperidino]butyl]-N-methylbenzamide hydrochloride Using a procedure similar to that described in Example 1 (alternative preparation), except using 4-(3-hydroxyphenyl) piperidine and (S)-N-[2-(3,4-dichlorophenyl)-4-oxobutyl]-N-methylbenzamide, the title compound was prepared. Chromatography with dichloromethane:methanol followed by conversion to the hydrochloride salt gave a white solid; mp 178°–182° C.; MS: 511; NMR (CD$_3$OD): 1.8–2.3 (m, 6), 2.8 (s, 3), 2.8–3.3 (m, 6), 3.4–3.9 (m, 4), 6.6–6.7 (m, 3), 7.0 (d, J=7, 1), 7.1–7.2 (m, 3), 7.3–7.6 (m, 6); $[\alpha]_D$=–40.3°, c=0.645 (methanol). Analysis for $C_{29}H_2Cl_2N_2O_2$·1.0 HCl·0.5 H$_2$O: Calculated: C, 62.54; H, 6.15; N, 5.03; Found: C, 62.19; H, 6.10; N, 5.0.

The intermediate 4-(3-hydroxyphenyl)piperidine was prepared as follows.

a. Benzyl 3-bromophenyl ether

Using a procedure similar to that described in Example 17.a., except using 3-bromophenol, the named compound was prepared as a white solid. MS: 263; NMR: 5.0 (s, 2), 6.9 (m, 1), 7.0–7.2 (m, 3), 7.3–7.4 (m, 5).

b. 1-Benzyloxycarbonyl-4-hydroxy-4-(2-benzyloxyphenyl) piperidine

Using a procedure similar to that described in Example 17.b., except using benzyl 3-bromophenyl ether, the named compound was prepared. This material was purified by chromatography; elution with hexane:isopropanol (9:1) afforded the named material (2.44 g) as a solid; MS: 400 (M-18); NMR: 1.6–1.7 (m, 3), 2.0 (br, 2) 3.3 (br, 2), 4.1 (br, 2), 5.0 (s, 2), 5.1 (s, 2), 6.9 (m, 1), 7.0 (m, 1), 7.1 (m, 2) 7.2–7.5 (m, 11).

c. 1-Benzyloxycarbonyl-4-(2-benzyloxyphenyl)piperidine

Using a procedure similar to that described in Example 13.b., except using 1-benzyloxycarbonyl-4-hydroxy-4-(3-benzyloxyphenyl)piperidine, the named compound was prepared. This material was purified chromatography; elution with 3:1 hexane:ethyl acetate afforded the named material containing an impurity; MS: 402; NMR: 1.5–1.7 (m, 2), 1.8 (d, J=12, 2), 2.6 (m, 1), 2.9 (br, 2), 4.3 (br, 2), 5.0 (s, 2), 5.1 (s, 2), 6.7–7.4 (m, 14). Additional NMR signals corresponding to the impurity were also seen. This material was used in the next step without further purification.

d. 4-(2-Hydroxyphenyl)piperidine

Using a procedure similar to that described in Example 17.d., except using 1-benzyloxycarbonyl-4-(3-hydroxyphenyl)piperidine, the named compound was prepared: MS: 178; NMR: 1.6–1.7 (m, 2), 1.8–1.9 (m, 2), 2.0–2.4 (m, 4), 2.5–2.6 (m, 1), 2.7–2.8 (d, q, $J_1$=12, $J_2$=2.6, 1), 3.2 (br,d, J=12, 1), 6.6–6.7 (m, 1), 6.7–6.8 (m, 1), 7.0 (d, J=0.5, 1), 7.1–7.2 (t, J=7.7, 1).

EXAMPLE 19

(S)-N-[2-(3,4-Dichlorophenyl)-4-[4-(4-hydroxyphenyl) piperidino]butyl]-N-methylbenzamide hydrochloride Using a procedure similar to that described in Example 1 (alternative preparation), except using 4-(4-hydroxyphenyl) piperidine and (S)-N-[2-(3,4-dichlorophenyl)-4-oxobutyl]-N-methylbenzamide, the title compound was prepared. Chromatography with dichloromethane:methanol followed by conversion to the hydrochloride salt gave a white solid; mp 144°–160° C.; MS: 511; NMR (CD$_3$OD): 1.8–2.2 (m, 6), 27 (s, 3), 2.8–3.3 (m, 5), 3.4–3.9 (m, 3), 6.7 (d, J=8, 2), 7.0–7.2 (m, 5), 7.3–7.6 (m, 5); [α]$_D$=−36.8°, c=1.06 (methanol). Analysis for C$_{29}$H$_{32}$Cl$_2$N$_2$O$_2$·1.0 HCl·0.5 H$_2$O: Calculated: C, 62.54; H, 6.15; N, 5.03; Found: C, 62.16; H, 6.20; N, 4.74.

The intermediate 4-(4-hydroxyphenyl)piperidine was prepared as follows:

a. Benzyl 4-bromophenyl ether. Using a procedure similar to that described in Example 17.a. except using 4-bromophenol, the named compound was prepared as a white solid; MS: 263; NMR: 5.0 (s, 2), 6.8 (d, d, J$_1$=7, J$_2$=2.2, 2), 7.3–7.4 (m, 7).

b. 1-Benzyloxycarbonyl-4-hydroxy-4-(4-benzyloxyphenyl) piperidine

Using a procedure similar to that described in Example 17.b., except using benzyl 4-bromophenyl ether, the named compound was prepared. This material was purified by chromatography; elution with hexane:isopropanol (9:1) afforded the named material (2.44 g) as a solid; MS: 418; NMR: 1.7 (d, J=13, 2), 1.9–2.0 (br, 2), 3.3 (br, 2), 4.1 (br, 2), 5.05 (s, 2), 5.14 (s, 2), 6.9–7.0 (m, 2), 7.3–7.5 (m, 12).

c. 1-Benzyloxycarbonyl-4-(4-benzyloxyphenyl)piperidine

Using a procedure similar to that described in Example 13.b., except using 1-benzyloxycarbonyl-4-hydroxy-4-(4-benzyloxyphenyl)piperidine, the named compound was prepared. This material was purified by chromatography; elution with 3:1 hexane:ethyl acetate afforded the named material containing an impurity; MS: 402; NMR: 1.5 (m, 2), 1.8 (br, 2), 2.6 (m, 1), 2.9 (br, 2), 4.4 (br, 2), 5.0–5.2 (s, 4), 6.9 (m, 2), 7.1 (m, 1), 7.2–7.5 (m, 11). Additional NMR signals corresponding to the impurity were also seen. This material was used in the next step without further purification.

d. 4-(4-Hydroxyphenyl)piperidine

Using a procedure similar to that described in Example 17.d., except using 1-benzyloxycarbonyl-4-(4-hydroxyphenyl)piperidine, the title compound was prepared: MS: 178; NMR: 1.3–1.5 (m, 2), 1.6 (d, J=11, 2), 2.3–2.5 (m, 3), 3.0 (d, J=12, 2), 6.6 (d, J=8, 2), 7.0 (d, J=8, 2).

EXAMPLE 20

N-[2-(3,4-Dichlorophenyl)-4-[4-(2,4-dihydroxyphenyl) piperidino]butyl]-N-methylbenzamide hydrochloride Using a procedure similar to that described in Example 1 (alternate procedure), except using 4-(2,4-dihydroxyphenyl) piperidine, the title compound was prepared. Chromatography with dichloromethane:methanol followed by conversion to the hydrochloride salt gave a white solid; mp 184°–190° C.; MS: 527; NMR (CD$_3$OD): 1.8–2.0 (m, 5), 20–2.1 (br, 1), 2.6 (s, 2), 2.6–3.2 (m, 7), 3.3–3.5 (m, 2), 3.7–3.8 (m, 2), 6.1 (m, 2), 6.7(m, 1), 6.9(m, 1) 7.0–7.1 (m, 2), 7.2–7.6 (m, 7). Analysis for C$_{29}$H$_{32}$Cl$_2$N$_2$O$_3$·1.0 HCl·1.0 H$_2$O: Calculated: C, 59.85; H, 6.00; N, 4.81; Found: C, 59.7; H, 5.89; N, 4.73.

The intermediate 4-(2,4-dihydroxyphenyl)piperidine was prepared as follows:

a. 2,4-Dibenzyloxybromobenzene

Using a procedure similar to that described in Example 17.a., except using 4-bromoresorcinol and using two equivalents of benzyl bromide and potassium carbonate, the named compound was prepared as a white solid; MS: 369; NMR: 5.0 (s, 2), 5.1(s, 2), 6.47(d, d, J$_1$=8, J$_2$=2.6, 1), 6.6 (d, J=2.7, 1), 7.2–7.5 (m, 11).

b. 1-Benzyloxycarbonyl-4-hydroxy-4-(2,4-dibenzyloxyphenyl)piperidine

Using a procedure similar to that described in Example 17.b., except using 2,4-dibenzyloxybromobenzene, the named compound was prepared. This material was purified by chromatography; elution with hexane:isopropanol (9:1) afforded the named material (2.44 g) as an oil; MS: 524; NMR: 1.8–2.1 (m, 4), 3.3 (b, 2), 3.9 (s, 1), 4.0–4.1 (br, 2), 5.03 (s, 2), 5.09 (s, 2), 5.13 (s, 2), 6.5 (d, d, J$_1$=9, J$_2$=2.4, 1), 6.7 (d, J=2.4, 1), 7.1 (d, J=8, 1), 7.2–7.5 (m, 18)

c. 1-Benzyloxycarbonyl-4-(4-benzyloxyphenyl)piperidine

Using a procedure similar to that described in Example 13.b., except using 1-benzyloxycarbonyl-4-hydroxy-4-(2,4-dibenzyloxyphenyl)piperidine, the named compound was prepared. This material was purified by chromatography; elution with 3:1 hexane:ethyl acetate afforded the named material containing an impurity; MS: 508; NMR: 1.5–1.7 (m, 2), 1.7–1.9 (br, 2), 2.8 (m, 2), 3.0 (m, 2), 4.3–4.4 (br, 2), 5.0 (s, 2), 5.05 (s, 2), 5.17 (s, 2), 6.54 (d,d, J$_1$=8, J$_2$=2.4, 1), 6.0 (d, J=2, 2), 7.0 (d, J=8, 1), 7.2–7.4 (m, 15). Additional NMR signals corresponding to the impurity were also seen. This material was used in the next step without further purification.

d. 4-(2,4-Dihydroxyphenyl)piperidine

Using a procedure similar to that described in Example 17.d., except using 1-benzyloxycarbonyl-4-(2,4-dihydroxyphenyl)piperidine, the named compound was prepared: MS: 194; NMR: 1.5–1.7 (m, 2), 1.7–1.9 (m, 2), 2.7–2.8 (m, 2), 2.9- 3.0 (m, 1), 3.0–3.1 (m, 2), 6.2 (m, 2), 6.88 (d, J=8, 1).

EXAMPLE 21

N-[2-(3,4-Dichlorophenyl)-4-[4-(2,5-dimethoxyphenyl) piperidino]butyl]-N-methylbenzamide hydrochloride Using a procedure similar to that described in Example 1 (alternate procedure), except using 4-(2,5-dimethoxyphenyl)piperidine, the title compound was prepared. Chromatography, eluting with dichloromethane:methanol (9:1), followed by conversion to the hydrochloride salt gave a white solid; mp 85°–110° C. (dec); MS: 555; NMR (CD$_3$OD): 1.9–2.2 (m, 6), 2.8 (s, 3), 2.8–3.2 (m, 6), 3.5–3.6 (m, 3), 3.75 (s, 3), 3.79 (s, 3), 3.8–3.9 (m, 1), 6.7–6.8 (m, 2), 6.9 (d, J=9, 1), 7.0–7.2 (m, 3), 7.4–7.5 (m, 4), 7.6 (m, 1). Analysis for C$_{31}$H$_{36}$Cl$_2$N$_2$O$_3$·1.0 HCl·1.5 H$_2$O: Calculated: C, 60.15; H, 6.51; N, 4.53; Found: C, 60.23; H, 6.12; N, 4.51.

The intermediate 4-(2,5-dimethoxyphenyl)piperidine was prepared as follows.

a. 1-Benzyloxycarbonyl-4-hydroxy-4-(2,5-dimethoxyphenyl)piperidine

Using a procedure similar to that described in Example 13.a., except using 2,5-dimethoxybromobenzene, the title compound was prepared. This material was crystallized from ethyl acetate:hexane as a white solid; MS: 372; NMR: 1.9–2.0 (m, 4), 3.4 (br, 2), 3.76 (s, 3), 3.86 (s, 3), 4.1 (br, 2), 4.2 (s, 1), 5.1 (s, 2), 6.7–6.8 (m, 3), 7.2–7.4 (m, 5).

b. 1-Benzyloxycarbonyl-4-(2,5-dimethoxyphenyl) piperidine

Using a procedure similar to that described in Example 13.b., except using 1-benzyloxycarbonyl-4-hydroxy-4-(2,5- dimethoxyphenyl)piperidine, the named compound was prepared. This material was purified by chromatography; elution with 3:1 hexane:ethyl acetate afforded the named material containing an impurity; MS: 556; NMR: 1.5–1.6 (m, 2), 1.8 (d, J=12, 2), 2.9 (m, 2), 3.1 (m, 1), 4.3–4.3 (m, 2), 5.1 (s, 1), 6.7–6.8 (m, 3), 7.2–7.8 (m, 5). Additional NMR signals corresponding to the impurity were also seen. This material was used in the next step without further purification.

c. 4-(2,5-Dimethoxyphenyl)piperidine

Using a procedure similar to that described in Example 17.c., except using 1-benzyloxycarbonyl-4-(2,5-dimethoxyphenyl)piperidine, the named compound was prepared: MS: 222; NMR: 1.6 (d, q, $J_1$=12, $J_2$=3.9, 2), 1.7–1.8 (m, 2.7–2.8 (d, t, $J_1$=12, $J_2$=2.5, 2), 3.0–3.1 (m, 1), 3.1(d, J=12, 2), 3.7 (s, 3), 3.8 (s, 3), 6.65(d,d, $J_1$=9, $J_2$=3,1), 6.8 (m, 2).

EXAMPLE 22

N-[2-(3,4-Dichlorophenyl)-4-[4-(2,5-dihydroxyphenyl)piperidino]butyl]-N-methylbenzamide hydrochloride Using a procedure similar to that described in Example 1 (alternate procedure), except using 4-(2,5-dihydroxyphenyl)piperidine, the title compound was prepared. Chromatography with dichloromethane:methanol:triethylamine (19:1:1) followed by conversion to the hydrochloride salt gave a white solid; mp 168°–175° C.; MS: 527; NMR (CD$_3$OD): 1.8–2.2 (m, 6), 2.7 (s, 2), 2.7–3.3 (m, 7), 3.4–3.8 (m, 4), 6.4–6.6 (m, 3), 6.9–7.2 (m, 3), 7.3–7.6 (m, 5). Analysis for $C_{29}H_{32}Cl_2N_2O_3 \cdot 1.0$ HCl·1.0 $H_2O$: Calculated: C, 59.85; H, 6.06; N, 4.81; Found: C, 59.63; H, 5.88; N, 4.77.

The intermediate 4-(2,5-dihydroxyphenyl)piperidine was prepared as follows.

a. 4-(2,5-Dihydroxyphenyl)piperidine

A solution of 1-benzyloxycarbonyl-4-(2,5-dimethoxyphenyl)piperidine (0.54 g), prepared as described in Example 21.b., in 10 mL of dichloromethane, was cooled to 0° C. and treated with a solution of boron tribromide in dichloromethane (1.0M, 9 mL). After stirring for 1 hour at 0° C., the reaction mixture was allowed to warm to room temperature. At the end of the period, the reaction mixture was cooled to 0° C. and quenched with methanol. The resulting solution was evaporated and then treated with additional amounts of methanol. After evaporation the product was obtained as a yellow solid (0.42 g); MS: 194; NMR: 1.6–1.9 (m, 4), 3.0 (m, 2), 3.3 (br, 2), 6.4–6.5 (m, 2), 6.6 (d, J=8, 1), 8.3–8.8 (m, 3).

EXAMPLE 23

N-[2-(3,4-Dichlorophenyl)-4-(spiro[isobenzofuran-1(3H), 4'-piperidin]-1'-yl)butyl]1-N-methylbenzamide hydrochloride Using a procedure similar to that described in Example 1 (alternate procedure), except using spiro[isobenzofuran-1(3H),4'-piperidine], the title compound was prepared. Chromatography, eluting with dichloromethane:methanol, followed by conversion to the hydrochloride salt gave a white solid; mp 120°–126° C.; MS: 523; NMR (CD$_3$OD): 1.9 (br, 3), 1.9–2.3 (m, 3), 2.8 (s, 3), 2.8–3.5 (br, 5), 3.5 (m, 2), 3.8 (m, 2), 5,1 (s, 2), 7.0 (br, 1), 7.2–7.6 (m, 11). Analysis for $C_{30}H_{32}Cl_2N_2O_2 \cdot 1.0$ HCl·1.5 $H_2O$: Calculated: C, 61.39; H, 6.18; N, 4.77; Found: C, 61.24; H, 5.82; N, 4.76.

The intermediate spiro[isobenzofuran-1(3H),4'-piperidine] was prepared as follows.

a. 1'-Benzyloxycarbonyl-3-oxospiro[isobenzofuran-1(3H), 4'-piperidine]

A solution of N-methylbenzamide (0.38 g) in 200 mL of anhydrous tetrahydrofuran was cooled to −78° C. and treated with tert-butyl lithium (30 mL, 1.7M). At the end of the addition, the reaction mixture was allowed to warm to 0° C. and stirred at this temperature for 1 hour and then cooled back to −78° C. After treatment with a solution of 1-benzyloxycarbonyl-4-piperidone (5.83 g) in 2 mL of tetrahydrofuran, the reaction mixture was stirred at −78° C. for 40 minutes and then quenched with 300 mL of saturated ammonium chloride solution. Extraction with ethyl acetate, washing the organic layer with brine, drying over magnesium sulfate and evaporation afforded the crude product. This material was partially purified by column chromatography; elution with ethyl acetate:hexane (6:4) afforded the named material (5.25 g); MS: 238 (M-99); NMR: 1.6–1.7 (m, 2), 2.0–2.1 (m, 2), 3.4 (br., 2), 4.0–4.1 (br, 2), 5.2(s, 1), 7.2–7.4 (m, 5), 7.5 (m, 1), 7.7 (m, 1), 7.9 (m, 1).

b. 3-Oxospiro[isobenzofuran-1(3H),4'-piperidine]

Using a procedure similar to that described in Example 17.d., except using 1'-benzyloxycarbonyl-3-oxospiro [isobenzofuran-1(3H),4'-piperidine], the named compound was prepared; MS: 204; NMR: 1.6–1.7 (m, 2), 2.0–2.1 (m, 2), 3.0–3.2 (m, 4), 7.4 (d, J=7,1), 7.5 (d, t, $J_1$=7.5, $J_2$=0.9, 1), 7.7 (m, 1), 7.9 (m, 1).

c. Spiro[isobenzofuran-1(3H), 4' -piperidine]

A solution of lithium aluminum hydride (7.5 mL 1M in ether) diluted with 35 mL of tetrahydrofuran was cooled to 0° C. and added to a suspension of 3-oxospiro [isobenzofuran-1(3H),4'-piperidine] (0.38 g) in 40 mL of anhydrous tetrahydrofuran containing boron trifluoride etherate (6.9 mL). The reaction mixture was allowed to warm to room temperature and then refluxed for 3 hours. At the end of this period, the reaction mixture was cooled in ice and treated with 5% HCl (8 mL) followed by water (8 mL). After concentrating under reduced pressure, the reaction mixture was treated with concentrated HCl (8 mL) and heated to reflux, cooled to room temperature, the pH was adjusted to 5 by adding sodium hydroxide solution and extracted with ether. The aqueous layer was made basic (pH 11) with sodium hydroxide and extracted with two portions of dichloromethane. The dichloromethane layer was dried and evaporated to afford the named product (0.28 g) which was used in the next step without further purification; MS: 190; NMR: 7–1.1.9 (m, 4), 2.9–3.1 (m, 4), 5.1 (s, 2), 7.1–7.3 (m, 4).

EXAMPLE 24

N-[2-(3,4-Dichlorophenyl)-4-(3-oxospiro[isobenzofuran-1 (3H),4'-piperidin]-1'-yl)butyl]-N-methylbenzamide hydrochloride Using a procedure similar to that described in Example 1 (alternative preparation), except using 3-oxospiro [isobenzofuran-1(3H),4'-piperidine] (prepared as described in Example 23.b.), the title compound was prepared. Conversion to the hydrochloride salt gave a white solid; mp 163°–168° C.; MS: 537; NMR (CD$_3$OD): 2.0 (b, 3), 2.3 (m, 1), 2.6 (m, 2), 2.8 (s, 2), 3.0 (m, 2), 3.2–3.4(m, 3), 3.5–3.9(m, 5). Analysis for $C_{30}H_{30}Cl_2N_2O_3 \cdot 1.0$ HCl·0.5 $H_2O$: Calculated: C, 61.81; H, 5.53; N, 4.81; Found: C, 61.55; H, 5.54; N, 4.91.

EXAMPLE 25

N-[2-(3,4-Dichlorophenyl)-4-[4-(4-N-methylcarbamoylphenyl)piperidino]butyl]-N-methylbenzamide hydrochloride Using a procedure similar to that described in Example 1 (alternative preparation), except using 4-(4-N-methylcarbamoylphenyl)piperidine, the title compound was prepared. Chromatography with dichloromethane:methanol followed by conversion to the hydrochloride salt gave a white solid; mp 247°–249° C.; MS: 552; NMR (CD$_3$OD): 2.0–2.3 (m, 6), 2.7–3.5 (m, 3), 3.5–3.9 (m, 4), 7.0 (br, 1), 7.2 (m, 2), 7.3–7.6 (m, 7), 7.8 (d, J=8, 2). Analysis for C$_{31}$H$_{35}$Cl$_2$N$_3$O$_2$·1.0 HCl·1.0 H$_2$O: Calculated: C, 61.34; H, 6.31; N, 6.92; Found: C, 61.43; H, 6.12; N, 6.93.

The intermediate 4-(4-N-methylcarbamoylphenyl) piperidine was prepared as follows.

a. 4-Bromobenzoyl chloride

A mixture of 4-bromobenzoic acid (5 g) and thionyl chloride (15 mL) was stirred at the room temperature for 16 hours, heated to reflux for 6 hours and then stirred at room temperature for 16 hours. At the end of this period, the reaction mixture was diluted with chloroform and evaporated. The residue was treated with toluene, evaporated and the process was repeated three times. The product was obtained as a solid (5.63 g); MS: 221; NMR: 7,5 (m, 2), 7.9–8.1 (m, 2).

b. 4-Bromo-N-methylbenzamide

A solution of 4-bromobenzoyl chloride (5.6 g) in 50 mL of tetrahydrofuran was cooled to 0° C. and treated with aqueous methylamine (5 mL of 40%). After the addition was complete, the reaction mixture was allowed to warm to room temperature and stirred for 16 hours. At the end of this period, the reaction mixture was diluted with water, extracted with ethyl acetate and the organic layer was washed with 10% HCl followed by sodium carbonate. Upon drying over magnesium sulfate and evaporation, a white solid was obtained (4.64 g); MS: 214; NMR: 3.0 (d, J=5, 3), 6.2 (br, 1), 7.5–7.6 (m, 2), 7.6–7.7 (m, 2).

c. 1-Benzyloxycarbonyl-4-hydroxy-4-(4-N-methylcarbamoylphenyl)piperidine

Using a procedure similar to the one described in Example 17.b., except using 4-bromo-N-methybenzamide, the named compound was prepared. This material was purified by column chromatography; elution with hexane-:ethyl acetate (1:1) afforded the named product; MS: 369; NMR: 1.7 (m, 2), 2.0 (br, 2), 2.2 (s, 1), 3.0 (d, J=5, 3), 3.3 (br, 2), 4.1 (br, 2), 6.2 (d, J=4, 1), 5.1 (s, 2), 7.3–7.4 (m, 5), 7.5 (d, J=8, 2), 7.7 (d, J=8, 2).

d. 4-(4-N-Methylcarbamoylphenyl)-1,2,3,6-tetrahydropyridine

A solution of 1-benzyloxycarbonyl-4-hydroxy-4-(4-N-methylcarbamoylphenyl)piperidine (0.37 g) in 7.7 mL of trifluoroacetic acid was treated with 8.0 mL of triethylsilane and refluxed for 16 hours. At the end of this period, the volatile material was distilled under reduced pressure and the resulting residue was suspended in hexane to obtain the named product as a solid (0.3 g) together with an impurity; MS: 219; NMR: 1.7–1.9 (m, 2), 1.9 (br, 2), 2.8 (m, 3), 2.9–3.0 (m, 4), 7.3 (d, J=4, 2), 7.5–7.6 (m, 2). Additional peaks corresponding to the impurities were seen.

e. 4-(4-N-Methylcarbamoylphenyl)piperidine

A mixture of 4-(4-N-methylcarbamoylphenyl)-1,2,3,6-tetrahydropyridine (0.3 g), thioanisole (0.58 mL), methanol 15 mL, concentrated HCl (0.25 mL), and platinum oxide (5 mg) was hydrogenated (3.4 bar hydrogen pressure) for 16 hours. At the end of this period, the reaction mixture was filtered through diatomaceous earth, evaporated, and purified by chromatography. Elution with dichloromethane:methanol:triethylamine (8:2:0.5) afforded the named product as a yellow solid (0.19 g) MS: 219; NMR: 1.2 (m, d, 2), 1.5–1.8 (m, 2), 2.5–2.7 (m, 3), 2.7 (d, t, J=4, 2), 3.0 (d, J=12, 2), 7.3 (d, J=8, 2), 7.76 (d, J=8, 2), 8.36 (b, 1).

EXAMPLE 26

(S) -N-[2-(3,4-Dichlorophenyl)-4-[4-(2-fluoropyrid-3-yl) piperidino]butyl]-N-methylbenzamide hydrochloride Using a procedure similar to that described in Example 1 (alternative preparation), except using 4-(2-fluoropyrid-3-yl)piperidine and (S)-N-[2-(3,4-dichlorophenyl)-4-oxobutyl]-N-methylbenzamide, the title compound was prepared. Conversion to the hydrochloride salt gave a white solid; mp 74°–95° C.; MS: 514; NMR (CD$_3$OD): 1.9–2.3 (b, 6), 2.7–3.2 (m, 9), 3.4–3.9 (m, 4), 7.0–7.2 (m, 3), 7.3–7.4 (m, 5), 7.6 (m, 2), 7.8–7.9 (t, J=8, 1), 8.1 (d, J=4, 1). Analysis for C$_{28}$H$_{30}$Cl$_2$FN$_3$O·1.0 HCl·0.5 H$_2$O: Calculated: C, 60.06; H, 5.76; N, 7.50. Found: C, 60.13; H, 6.06; N, 7.02.

The intermediate 4-(2-fluoropyrid-3-yl)piperidine was prepared as follows:

a. 1-Benzyloxycarbonyl-4-hydroxy-4-(2-fluoropyrid-3-yl)piperidine

To a solution of lithium diisopropylamide (0.31 mol) in 300 mL of anhydrous tetrahydrofuran:hexane at −78° C. was added a solution of 2-fluoropyridine (24.6 mL) in 40 mL of anhydrous tetrahydrofuran. The reaction mixture was allowed to warm to −50° C., cooled back to −74° C. and treated dropwise with a solution of lithium bromide (55.5 g) and 1-benzyloxycarbonyl-4-oxopiperidine (55.5 g) in 300 mL of anhydrous tetrahydrofuran so that the temperature of the reaction mixture remained below −70° C. After the addition was complete, the reaction mixture was allowed to warm to −30° C. and then treated with water. The organic layer was separated and the aqueous layer was extracted with two portions of ether. Combined organic layers were dried and evaporated to afford the crude product. This material was purified by column chromatography to afford the pure product.

b. 1-Benzyloxycarbonyl-4-(2-fluoropyrid-3-yl)-1,2,3,6-tetrahydropyridine. A solution of 1-benzyloxycarbonyl-4-hydroxy-4-(2-fluoropyrid-3-yl)piperidine (3.3 g) in 50 mL of dichloromethane was cooled to 0° C. and treated with 10 mL of pyridine followed by thionyl chloride (0.80 mL). After stirring at room temperature for 16 hours, the reaction mixture was diluted with water and treated with sodium carbonate solution. Extraction with two portions of dichloromethane, drying of the organic layer with sodium sulfate and evaporation afforded the crude product. This material was purified by chromatography; elution with hexane:ethyl acetate (4:1) afforded the named material (2.35 g); MS: 313; NMR: 2.5 (br, 2), 3.7 (t, J=5.6, 2), 4.1–4.2 (d, d, J$_1$=5.6, J$_2$=2.7, 2), 5.2 (s, 2), 6.0 (br, 1), 7.2 (m, 1), 7.3–7.4 (m, 5), 7.6–7.7 (m, 1), 8.1 (d, d, J$_1$=3.4, J$_2$=1.4, 1).

c. 1-Benzyloxycarbonyl-4-(2-fluoropyrid-3-yl)piperidine

A solution of 1-benzyloxycarbonyl-4-(2-fluoropyrid-3-yl) -1,2,3,6-tetrahydropyridine (2.04 g) in 50 mL of ethanol was treated with platinum oxide (0.22 g) and the mixture was hydrogenated (3.4 bar hydrogen pressure) for 16 hours. At the end of this period, the reaction mixture was filtered through a pad of diatomaceous earth and the filtrate was evaporated to afford the named material as a white solid (2.0 g); MS: 315; NMR: 1.6 (br, 2), 1.8–1.9 (d, J=14, 2), 2.8–3.1 (m, 3), 4.3 (b, 2), 5.1 ( s, 2), 7.1–7.2 (m, 1), 7.2–7.4 (m, 5), 7.6 (m, 1), 8.1 (m, 1).

d. 4-(2-Fluoropyrid-3-yl)piperidine

A solution of 1-benzyloxycarbonyl-4-(2-fluoropyrid-3-yl) piperidine (0.36 g) in 5 mL of trifluoroacetic acid was heated to reflux for 30 minutes and evaporated. The residue thus obtained was dissolved in chloroform and evaporated. After repeating this process three times, the named product was obtained as an oil (0.64 g); MS: 181; NMR: 1.6–2.1 (m, 4), 3.0–3.4 (m, 5), 7.2–7.5 (m, 2), 7.8–7.9 (m, 4), 8.1 (m, 1), 8.2–8.8 (br, 2).

EXAMPLE 27

(S)-N-[2-(3,4-Dichlorophenyl)-4-[4-(2-pyridyl) piperidino]butyl]-N-methylbenzamide hydrochloride Using a procedure similar to that described in Example 1 (alternative preparation), except using 4-(2-pyridyl) piperidine and (S)-N-[2-(3,4-dichlorophenyl)-4-oxobutyl]-N-methylbenzamide, the title compound was prepared. Conversion to the hydrochloride salt Gave a white solid; mp 200°–202° C.; MS: 496; NMR: 2.14 (b, 8), 2.7 (s, 3), 3.4–3.9 (m, 8), 6.9–7.7 (m, 12), 8.16 (m, 1), 8.68 (m, 1), 10.4 (br, 1). Analysis for $C_{28}H_{31}Cl_2N_3O\cdot2.0$ HCl·0.5 $H_2O$: Calculated: C, 58.14; H, 5.92; N, 7.26 Found: C, 58.00; H, 5.90; N, 7.56.

The intermediate 4-(2-pyridyl)piperidine was prepared as follows:

a. 1-Benzyloxycarbonyl-4-hydroxy-4-(2-pyridyl)piperidine

To a solution of 2-bromopyridine (1.58 g) in 50 mL of anhydrous tetrahydrofuran at −78° C. was added tert-butyl lithium (6.5 mL of 1.7M) and the reaction mixture was stirred at −78° C. for 1 hour. At the end of this period, a solution of 1-benzyloxycarbonyl-4-oxopiperidine (2.34 g) in 20 mL of anhydrous tetrahydrofuran was added and the reaction mixture was allowed to stir at −78° C. for an additional 1 hour. Upon warming the reaction mixture to room temperature, aqueous ammonium chloride was added and the resulting mixture was extracted with ethyl acetate. The organic layer was washed with sodium chloride, dried over magnesium sulfate and evaporated to afford the crude product. This a material was purified by column chromatography; elution with 1:1 hexane:ethyl acetate afforded the named product (1.0 g); MS: 313; NMR: 6.63 (m, 3), 1.94 (m, 2), 3.37 (m, 2), 4.13 (m, 2).

b. 1-Benzyloxycarbonyl-4-(2-pyridyl)-1,2,3,6-tetrahydropyridine

A solution of 1-benzyloxycarbonyl-4-hydroxy-4-(2-pyridyl)piperidine (0.8 g) in 20 mL of dichloromethane at 0° C. was treated with pyridine (2 mL) followed by thionyl chloride (0.22 mL). The reaction mixture was allowed to warm to the room temperature and stirred for 16 hours. At the end of this period, the reaction mixture was diluted with water and extracted twice with ethyl acetate. The organic layer was washed with a solution of copper sulfate, dried over magnesium sulfate and concentrated under reduce pressure to obtain the crude material. This material was purified by column chromatography; elution with 1:1 hexane:ethylacetate afforded the named product (0.48 g); MS: 295; NMR: 2.67 (m, 2), 3.74 (m, 2), 4.2 (m, 2), 5.18 (s, 2), 6.6 (m, 1), 7.18 (m, 1), 7.36 (m, 6), 7.68 (m, 1), 8.56 (m, 1).

c. 4-(2-Pyridyl)piperidine

Using a procedure similar to that described in Example 17.c., except using 1-benzyloxycarbonyl-4-(2-pyridyl)-1,2,3,6-tetrahydropyridine, the named compound was prepared; MS: 163; NMR: 1.66 (m, 2), 2.0 (m, 2), 2.4 (m, 2), 2.7 (m, 2), 3.7 (m, 1). The presence of an impurity was also seen.

Formulae

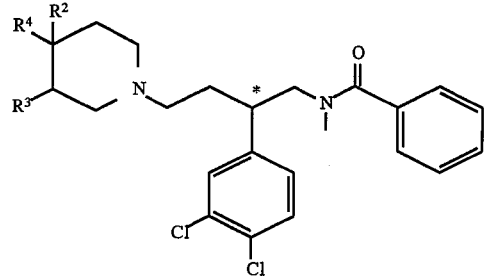

I

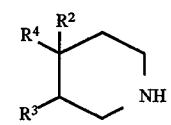

II

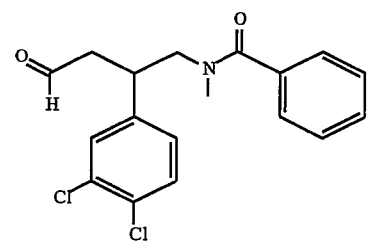

III

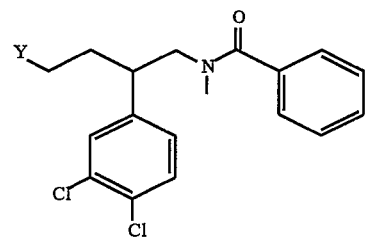

IV

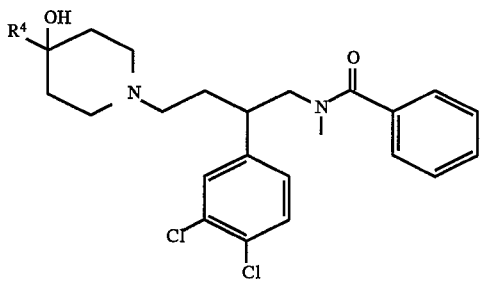

V

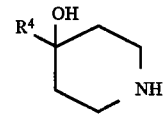

Va

Scheme I
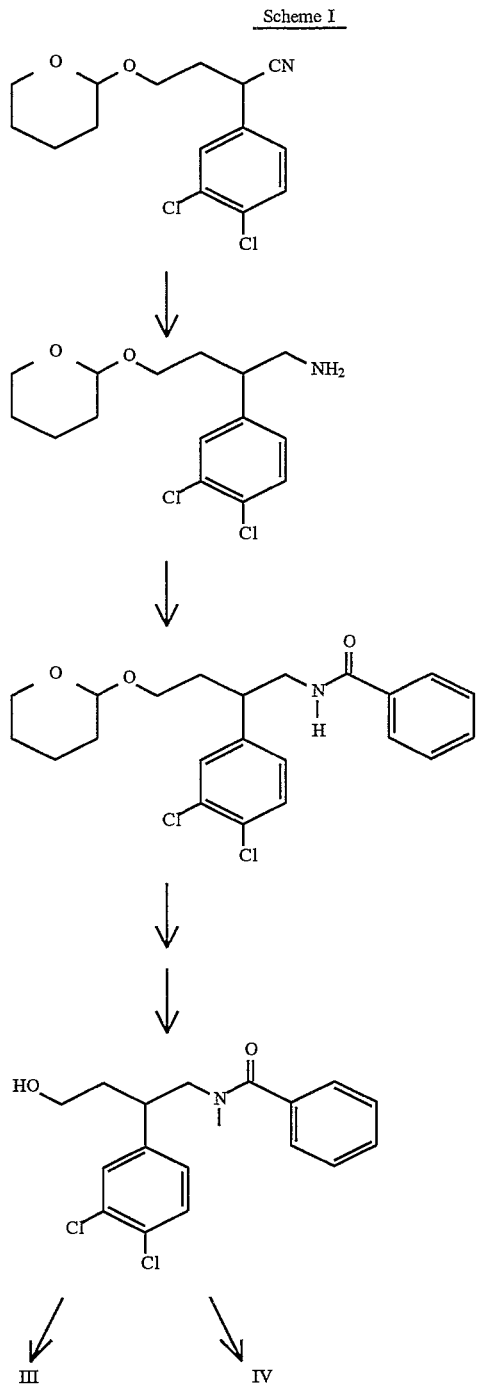
Scheme II
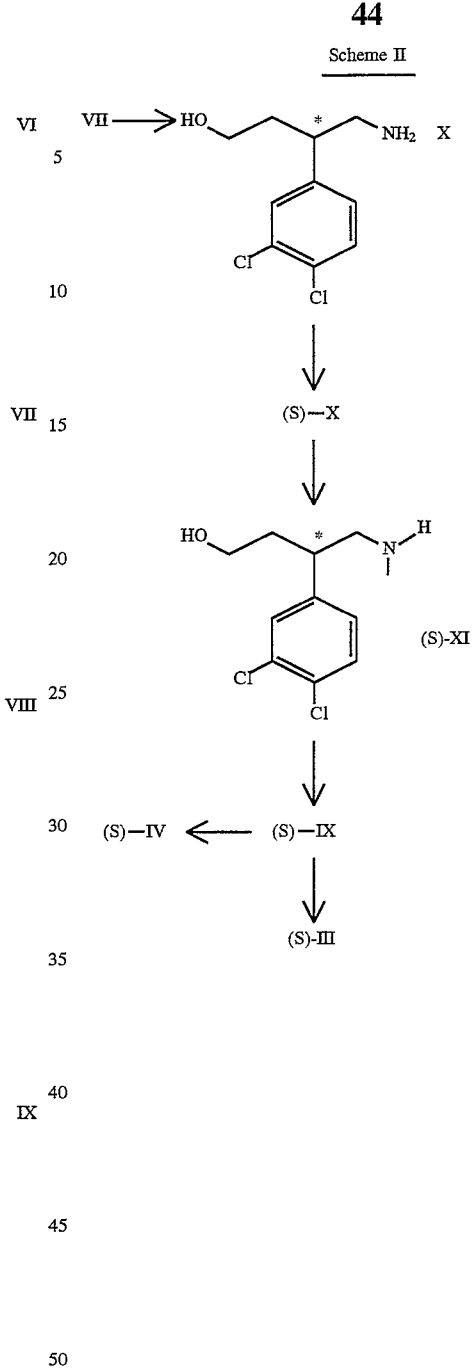

What is claimed is:

1. A method for the treatment of a disease in which Neurokinin A is implicated and antagonism of its action is desired comprising administering to a human or other mammal in need thereof an effective amount of a compound of formula I

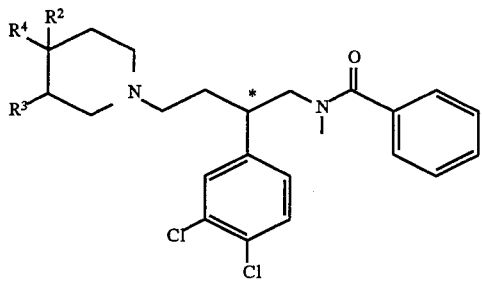

wherein $R^2$ and $R^3$ are each hydrogen or $R^2$ is hydrogen and $R^3$ is hydroxy; and $R^4$ is aryl or heteroaryl which may bear an aryl, aroyl, heteroaryl or heteroaroyl substituent and in which an aromatic or heteroaromatic portion may bear one or more subsitutents on carbon independently selected from halo, cyano, trifluoromethyl, nitro, hydroxy, (1–5C)alkoxy, (1–5C)alkanoyloxy, $NR^A R^B$, $NR^C R^D$, $C(=NR^G)NR^E R^F$, $COOR^K$, $CONR^L R^M$, mercapto, $S(O)_n R^N$, (1–5C)alkyl and (1–5C)alkanoyl wherein $NR^A R^B$ contains zero to about seven carbon atoms and each of $R^A$ and $R^B$ is independently hydrogen, (1–5C)alkyl or (3–6C)cycloalkyl, or $NR^A R^B$ forms a pyrrolidino, piperidino, morpholino, thiomorpholino (or its S-oxide) or piperazinyl group (which piperazinyl group may bear a methyl or ethyl group at the 4-position) any of which cyclic groups may further bear one or more methyl substituents; and wherein $R^C$ is hydrogen or (1–5C)alkyl and $R^D$ is (1–5C)alkanoyl, aroyl or heteroaroyl; or $R^D$ is a group of formula $C(=J)NR^E R^F$ in which J is oxygen, sulfur, $NR^G$ or $CHR^H$; and wherein $NR^E R^F$ contains zero to about seven carbon atoms and each of $R^E$ and $R^F$ is independently hydrogen, (1–5C)alkyl or (3–6C)cycloalkyl, or $NR^E R^F$ forms a pyrrolidino, piperidino, morpholino, thiomorpholino (or its S-oxide) or piperazinyl group (which piperazinyl group may bear a methyl or ethyl group at the 4-position) any of which cyclic groups may further bear one or more methyl substituents; or $R^E$ is hydrogen or (1–5C)alkyl, and $R^F$ together with $R^G$ forms an ethylene or trimethylene group; $R^G$ is hydrogen, (1–5C)alkyl or together with $R^F$ forms an ethylene or trimethylene group; $R^H$ is cyano, nitro or $SO_2 R^J$ in which $R^J$ is (1–5C)alkyl or phenyl; $R^K$ is hydrogen, (1–5C)alkyl, aryl, heteroaryl, arylmethyl or heteroarylmethyl; $NR^L R^M$ contains zero to about seven carbon atoms and each of $R^L$ and $R^M$ is independently hydrogen, (1–5C)alkyl or (3–6C)cycloalkyl, or $NR^L R^M$ forms a pyrrolidino, piperidino, morpholino, thiomorpholino (or its S-oxide) or piperazinyl group (which piperazinyl group may bear a methyl or ethyl group at the 4-position) any of which cyclic groups may further bear one or more methyl substituents; $R^N$ is (1–6C) alkyl, (3–6C)cycloalkyl, aryl or heteroaryl, and n is the integer 0, 1 or 2; and wherein a heteroaromatic nitrogen may bear a (1–5C)alkyl substituent; and further wherein a (1–5C)alkyl, (1–5C)alkoxy or (1–5C) alkanoyl substituent or portion of $R^4$ may bear a hydroxy, a (1–3C)alkoxy or one or more halo substituents provided that a carbon bound to nitrogen or oxygen does not bear a hydroxy or alkoxy substituent and that the α-carbon of an alkanoyl group does not bear a chloro, bromo or iodo substituent;

or $R^3$ is hydrogen and $R^2$ and $R^4$ together with a diradical $X^1$ and the piperidino 4-carbon to which they are attached form a spirocyclic ring wherein $R^4$ is phenyl which is joined to $R^2$ by an ortho-substituent diradical $X^1$ in which the phenyl $R^4$ may bear a further substituent selected from halo, (1–3C)alkyl, (1–3C)alkoxy, hydroxy, (1–3C)alkylthio, (1–3C)alkylsulfinyl and (1–3C)alkylsulfonyl; the diradical $X^1$ is methylene, carbonyl or sulfonyl; and $R^2$ is oxy or imino of formula $—NR^Q—$ in which $R^Q$ is hydrogen or (1–3C)alkyl;

or a pharmaceutically acceptable salt thereof.

2. A method as claimed in claim 1 in which aryl is phenyl, indenyl or naphthyl; heteroaryl is furyl, thienyl, pyrrolyl, pyridyl, pyrimidinyl, 1,3,4-oxadiazol-2-yl, 2-imidazolyl, or benz[d]isoxazol-3-yl; an optional substituent on an aromatic or heteroaromatic carbon of $R^4$ is fluoro, chloro, cyano, trifluoromethyl, hydroxy, methoxy, ethoxy, acetoxy, amino, methylamino, dimethylamino, acetamido, imidazolin-2-yl, carboxy, methoxycarbonyl, benzyloxycarbonyl, ethoxycarbonyl, carbamoyl, N,N-dimethylcarbamoyl, pyrrolidinocarbonyl, N-methylcarbamoyl, methylthio, methylsulfinyl, methylsulfonyl, methyl, ethyl, propyl, butyl, isopropyl, 2-methylpropyl, tert-butyl, formyl, acetyl, propionyl; a substituent on a heteroaromatic nitrogen of $R^4$ is methyl or ethyl; and a substituent on a (1–5C)alkyl, (1–5C)alkoxy or (1–5C)alkanoyl substituent or portion of $R^4$ is hydroxy, methoxy, ethoxy, chloro, fluoro or trifluoro.

3. A method as claimed in claim 1 in which $R^2$ and $R^3$ are each hydrogen and $R^4$ is phenyl which may bear a fluoro, chloro, hydroxy, methoxy, acetoxy, amino, acetamido, methoxycarbonyl, carbamoyl, methyl, ethyl or acetyl substituent.

4. A method as claimed in claim 3 in which $R^4$ is phenyl which bears a hydroxy substituent.

5. A method as claimed in claim 1 in which $R^2$ is hydrogen, $R^3$ is hydroxy which is trans- to $R^4$, and $R^4$ is phenyl which may bear a methoxy, hydroxy, methylthio or methylsulfinyl substituent.

6. A method as claimed in claim 1 in which $R^3$ is hydrogen and $R^2$ and $R^4$ together with a diradical $X^1$ and the piperidino 4-carbon to which they are attached form a spirocyclic ring wherein $R^4$ is phenyl which is joined to $R^2$ by an ortho-substituent diradical $X^1$ in which the phenyl $R^4$ may bear a further substituent selected from methoxy, hydroxy, methylthio, and methylsulfinyl; the diradical $X^1$ is methylene or carbonyl; and $R^2$ is oxy.

7. A method as claimed in claim 1 in which the substituted piperidino moiety of the compound of formula I is selected from 4-phenylpiperidino, 4-(2-methoxyphenyl)piperidino, 4-(3-methoxyphenyl)piperidino, 4-(4-methoxyphenyl)piperidino, 4-(2-hydroxyphenyl)piperidino, 4-(3-hydroxyphenyl)piperidino, 4-(4-hydroxyphenyl)piperidino, 4-(5-methyl-1,3,4-oxadiazol-2-yl)piperidino, 4-(4-ethoxycarbonylimidazol-2-yl)piperidino, 4-(3-pyridyl)piperidino, 4-(2-pyridyl)piperidino, 4-(2-fluoropyrid-3-yl)piperidino, (3R*,4R*)-3-hydroxy-4-phenylpiperidino, (3S, 4S)-3-hydroxy-4-phenylpiperidino, 4-(2-methylthiophenyl)piperidino, 4-(4-methylthiophenyl)piperidino, 4-(2-methylsulfinylphenyl)piperidino, 4-(4-methylsulfinylphenyl)piperidino, 4-(2,4-dihydroxyphenyl)piperidino, 4-(2,5-dimethoxyphenyl)piperidino, 4-(2,5-dihydroxyphenyl)piperidino, spiro[isobenzofuran-1(3H),4'-piperidin]-4'-yl, 3-oxospiro[isobenzofuran-1(3H),4'-piperidin]-1'-yl, and 4-(4-N-methylcarbamoylphenyl)piperidino.

8. A method as claimed in claim 1 wherein the method is for the treatment of asthma or a related disorder.

9. A pharmaceutical composition comprising a pharmaceutically acceptable diluent or carrier and a compound of formula I

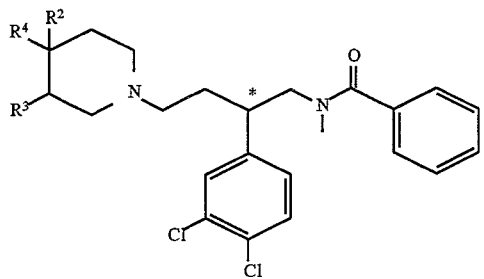

wherein $R^2$ and $R^3$ are each hydrogen or $R^2$ is hydrogen and $R^3$ is hydroxy; and $R^4$ is aryl or heteroaryl which may bear an aryl, aroyl, heteroaryl or heteroaroyl substituent and in which an aromatic or heteroaromatic portion may bear one or more subsitutents on carbon independently selected from halo, cyano, trifluoromethyl, nitro, hydroxy, (1–5C)alkoxy, (1–5C)alkanoyloxy, $NR^AR^B$, $NR^CR^D$, $C(=NR^G)NR^ER^F$, $COOR^K$, $CONR^LR^M$, mercapto, $S(O)_nR^N$, (1–5C)alkyl and (1–5C)alkanoyl wherein $NR^AR^B$ contains zero to about seven carbon atoms and each of $R^A$ and $R^B$ is independently hydrogen, (1–5C)alkyl or (3–6C)cycloalkyl, or $NR^AR^B$ forms a pyrrolidino, piperidino, morpholino, thiomorpholino (or its S-oxide) or piperazinyl group (which piperazinyl group may bear a methyl or ethyl group at the 4-position) any of which cyclic groups may further bear one or more methyl substituents; and wherein $R^C$ is hydrogen or (1–5C)alkyl and $R^D$ is (1–5C)alkanoyl, aroyl or heteroaroyl; or $R^D$ is a group of formula $C(=J)NR^ER^F$ in which J is oxygen, sulfur, $NR^G$ or $CHR^H$; and wherein $NR^ER^F$ contains zero to about seven carbon atoms and each of $R^E$ and $R^F$ is independently hydrogen, (1–5C)alkyl or (3–6C)cycloalkyl, or $NR^ER^F$ forms a pyrrolidino, piperidino, morpholino, thiomorpholino (or its S-oxide) or piperazinyl group (which piperazinyl group may bear a methyl or ethyl group at the 4-position) any of which cyclic groups may further bear one or more methyl substituents; or $R^E$ is hydrogen or (1–5C)alkyl, and $R^F$ together with $R^G$ forms an ethylene or trimethylene group; $R^G$ is hydrogen, (1–5C)alkyl or together with $R^F$ forms an ethylene or trimethylene group; $R^H$ is cyano, nitro or $SO_2R^J$ in which $R^J$ is (1–5C)alkyl or phenyl; $R^K$ is hydrogen, (1–5C)alkyl, aryl, heteroaryl, arylmethyl or heteroarylmethyl; $NR^LR^M$ contains zero to about seven carbon atoms and each of $R^L$ and $R^M$ is independently hydrogen, (1–5C)alkyl or (3–6C)cycloalkyl, or $NR^LR^M$ forms a pyrrolidino, piperidino, morpholino, thiomorpholino (or its S-oxide) or piperazinyl group (which piperazinyl group may bear a methyl or ethyl group at the 4-position) any of which cyclic groups may further bear one or more methyl substituents; $R^N$ is (1–6C)alkyl, (3–6C)cycloalkyl, aryl or heteroaryl, and n is the integer 0, 1 or 2; and wherein a heteroaromatic nitrogen may bear a (1–5C)alkyl substituent; and further wherein a (1–5C)alkyl, (1–5C)alkoxy or (1–5C)alkanoyl substituent or portion of $R^4$ may bear a hydroxy, a (1–3C)alkoxy or one or more halo substituents provided that a carbon bound to nitrogen or oxygen does not bear a hydroxy or alkoxy substituent and that the α-carbon of an alkanoyl group does not bear a chloro, bromo or iodo substituent;

or $R^3$ is hydrogen and $R^2$ and $R^4$ together with a diradical $X^1$ and the piperidino 4-carbon to which they are attached form a spirocyclic ring wherein $R^4$ is phenyl which is joined to $R^2$ by an ortho-substituent diradical $X^1$ in which the phenyl $R^4$ may bear a further substituent selected from halo, (1–3C)alkyl, (1–3C)alkoxy, hydroxy, (1–3C)alkylthio, (1–3C)alkylsulfinyl and (1–3C)alkylsulfonyl; the diradical $X^1$ is methylene, carbonyl or sulfonyl; and $R^2$ is oxy or imino of formula —$NR^Q$— in which $R^Q$ is hydrogen or (1–3C)alkyl;

or a pharmaceutically acceptable salt thereof.

10. A pharmaceutical composition as claimed in claim 9 in which aryl is phenyl, indenyl or naphthyl; heteroaryl is furyl, thienyl, pyrrolyl, pyridyl, pyrimidinyl, 1,3,4-oxadiazol-2-yl, 2-imidazolyl, or benz[d]isoxazol-3-yl; an optional substituent on an aromatic or heteroaromatic carbon of $R^4$ is fluoro, chloro, cyano, trifluoromethyl, hydroxy, methoxy, ethoxy, acetoxy, amino, methylamino, dimethylamino, acetamido, imidazolin-2-yl, carboxy, methoxycarbonyl, benzyloxycarbonyl, ethoxycarbonyl, carbamoyl, N,N-dimethylcarbamoyl, pyrrolidinocarbonyl, N-methylcarbamoyl, methylthio, methylsulfinyl, methylsulfonyl, methyl, ethyl, propyl, butyl, isopropyl, 2-methylpropyl, tert-butyl, formyl, acetyl, propionyl; a substituent on a heteroaromatic nitrogen of $R^4$ is methyl or ethyl; and a substituent on a (1–5C)alkyl, (1–5C)alkoxy or (1–5C)alkanoyl substituent or portion of $R^4$ is hydroxy, methoxy, ethoxy, chloro, fluoro or trifluoro.

11. A pharmaceutical composition as claimed in claim 9 in which $R^2$ and $R^3$ are each hydrogen and $R^4$ is phenyl which may bear a fluoro, chloro, hydroxy, methoxy, acetoxy, amino, acetamido, methoxycarbonyl, carbamoyl, methyl, ethyl or acetyl substituent.

12. A pharmaceutical composition as claimed in claim 11 in which $R^4$ is phenyl which bears a hydroxy substituent.

13. A pharmaceutical composition as claimed in claim 9 in which $R^2$ is hydrogen, $R^3$ is hydroxy which is trans- to $R^4$, and $R^4$ is phenyl which may bear a methoxy, hydroxy, methylthio or methylsulfinyl substituent.

14. A pharmaceutical composition as claimed in claim 9 in which $R^3$ is hydrogen and $R^2$ and $R^4$ together with a diradical $X^1$ and the piperidino 4-carbon to which they are attached form a spirocyclic ring wherein $R^4$ is phenyl which is joined to $R^2$ by an ortho-substituent diradical $X^1$ in which the phenyl $R^4$ may bear a further substituent selected from methoxy, hydroxy, methylthio, and methylsulfinyl; the diradical $X^1$ is methylene or carbonyl; and $R^2$ is oxy.

15. A pharmaceutical composition as claimed in claim 9 in which the substituted piperidino moiety of the compound of formula I is selected from 4-phenylpiperidino, 4-(2-methoxyphenyl)piperidino, 4-(3-methoxyphenyl)piperidino, 4-(4-methoxyphenyl)piperidino, 4-(2-hydroxyphenyl)piperidino, 4-(3-hydroxyphenyl)piperidino, 4-(4-hydroxyphenyl)piperidino, 4-(5-methyl-1,3,4-oxadiazol-2-yl)piperidino, 4-(4-ethoxycarbonylimidazol-2-yl)piperidino, 4-(3-pyridyl)piperidino, 4-(2-pyridyl)piperidino, 4-(2-fluoropyrid-3-yl)piperidino, (3R*,4R*)-3-hydroxy-4-phenylpiperidino, (3S,4S)-3-hydroxy-4-phenylpiperidino, 4-(2-methylthiophenyl)piperidino, 4-(4-methylthiophenyl)piperidino, 4-(2-methylsulfinylphenyl)piperidino, 4-(4-methylsulfinylphenyl)piperidino, 4-(2,4-dihydroxyphenyl)piperidino, 4-(2,5-dimethoxyphenyl)piperidino, 4-(2,5-dihydroxyphenyl)piperidino, spiro[isobenzofuran-1(3H),4'-piperidin]-1'-yl, 3-oxospiro[isobenzofuran-1(3H),4'-piperidin]-1'-yl, and 4-(4-N-methylcarbamoylphenyl)piperidino.

16. A pharmaceutical composition as claimed in claim 9 in which the pharmaceutically acceptable salt is one made with hydrochloric, sulfuric, phosphoric, methanesulfonic, or para-toluenesulfonic acid.

17. A compound of formula I

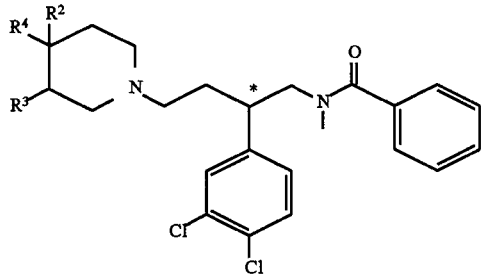

wherein $R^2$ and $R^3$ are each hydrogen or $R^2$ is hydrogen and $R^3$ is hydroxy; and $R^4$ is aryl or heteroaryl which may bear an aryl, aroyl, heteroaryl or heteroaroyl substituent and in which an aromatic or heteroaromatic portion may bear one or more subsitutents on carbon independently selected from halo, cyano, trifluoromethyl, nitro, hydroxy, (1–5C)alkoxy, (1–5C)alkanoyloxy, $NR^AR^B$, $NR^CR^D$, $C(=NR^G)NR^ER^F$, $COOR^K$, $CONR^LR^M$, mercapto $S(O)_nR^N$, (1–5C)alkyl and (1–5C)alkanoyl wherein $NR^AR^B$ contains zero to about seven carbon atoms and each of $R^A$ and $R^B$ is independently hydrogen, (1–5C)alkyl or (3–6C)cycloalkyl, or $NR^AR^B$ forms a pyrrolidino, piperidino, morpholino, thiomorpholino (or its S-oxide) or piperazinyl group (which piperazinyl group may bear a methyl or ethyl group at the 4-position) any of which cyclic groups may further bear one or more methyl substituents; and wherein $R^C$ is hydrogen or (1–5C)alkyl and $R^D$ is (1–5C)alkanoyl, aroyl or heteroaroyl; or $R^D$ is a group of formula $C(=J)NR^ER^F$ in which J is oxygen, sulfur, $NR^G$ or $CHR^H$; and wherein $NR^ER^F$ contains zero to about seven carbon atoms and each of $R^E$ and $R^F$ is independently hydrogen, (1–5C)alkyl or (3–6C)cycloalkyl, or $NR^ER^F$ forms a pyrrolidino, piperidino, morpholino, thiomorpholino (or its S-oxide) or piperazinyl group (which piperazinyl group may bear a methyl or ethyl group at the 4-position) any of which cyclic groups may further bear one or more methyl substituents; or $R^E$ is hydrogen or (1–5C)alkyl, and $R^F$ together with $R^G$ forms an ethylene or trimethylene group; $R^G$ is hydrogen, (1–5C)alkyl or together with $R^F$ forms an ethylene or trimethylene group; $R^H$ is cyano, nitro or $SO_2R^J$ in which $R^J$ is (1–5C)alkyl or phenyl; $R^K$ is hydrogen, (1–5C)alkyl, aryl, heteroaryl, arylmethyl or heteroarylmethyl; $NR^LR^M$ contains zero to about seven carbon atoms and each of $R^L$ and $R^M$ is independently hydrogen, (1–5C)alkyl or (3–6C)cycloalkyl, or $NR^LR^M$ forms a pyrrolidino, piperidino, morpholino, thiomorpholino (or its S-oxide) or piperazinyl group (which piperazinyl group may bear a methyl or ethyl group at the 4-position) any of which cyclic groups may further bear one or more methyl substituents; $R^N$ is (1–6C) alkyl, (3–6C)cycloalkyl, aryl or heteroaryl, and n is the integer 0, 1 or 2; and wherein a heteroaromatic nitrogen may bear a (1–5C)alkyl substituent; and further wherein a (1–5C)alkyl, (1–5C)alkoxy or (1–5C) alkanoyl substituent or portion of $R^4$ may bear a hydroxy, a (1–3C)alkoxy or one or more halo substituents provided that a carbon bound to nitrogen or oxygen does not bear a hydroxy or alkoxy substituent and that the α-carbon of an alkanoyl group does not bear a chloro, bromo or iodo substituent;

or $R^3$ is hydrogen and $R^2$ and $R^4$ together with a diradical $X^1$ and the piperidino 4-carbon to which they are attached form a spirocyclic ring wherein $R^4$ is phenyl which is joined to $R^2$ by an ortho-substituent diradical $X^1$ in which the phenyl $R^4$ may bear a further substituent selected from halo, (1–3C)alkyl, (1–3C)alkoxy, hydroxy, (1–3C)alkylthio, (1–3C)alkylsulfinyl and (1–3C)alkylsulfonyl; the diradical $X^1$ is methylene, carbonyl or sulfonyl; and $R^2$ is oxy or imino of formula —$NR^Q$— in which $R^Q$ is hydrogen or (1–3C)alkyl;

or a pharmaceutically acceptable salt thereof.

18. A compound as claimed in claim 17 in which aryl is phenyl, indenyl or naphthyl; heteroaryl is furyl, thienyl, pyrrolyl, pyridyl, pyrimidinyl, 1,3,4-oxadiazol-2-yl, 2-imidazolyl, or benz[d]isoxazol-3-yl; an optional substituent on an aromatic or heteroaromatic carbon of $R^4$ is fluoro, chloro, cyano, trifluoromethyl, hydroxy, methoxy, ethoxy, acetoxy, amino, methylamino, dimethylamino, acetamido, imidazolin-2-yl, carboxy, methoxycarbonyl, benzyloxycarbonyl, ethoxycarbonyl, carbamoyl, N,N-dimethylcarbamoyl, pyrrolidinocarbonyl, N-methylcarbamoyl, methylthio, methylsulfinyl, methylsulfonyl, methyl, ethyl, propyl, butyl, isopropyl, 2-methylpropyl, tert-butyl, formyl, acetyl, propionyl; a substituent on a heteroaromatic nitrogen of $R^4$ is methyl or ethyl; and a substituent on a (1–5C)alkyl, (1–5C)alkoxy or (1–5C)alkanoyl substituent or portion of $R^4$ is hydroxy, methoxy, ethoxy, chloro, fluoro or trifluoro.

19. A compound as claimed in claim 17 in which $R^2$ and $R^3$ are each hydrogen and $R^4$ is phenyl which may bear a fluoro, chloro, hydroxy, methoxy, acetoxy, amino, acetamido, methoxycarbonyl, carbamoyl, methyl, ethyl or acetyl substituent.

20. A compound as claimed in claim 19 in which $R^4$ is phenyl which bears a hydroxy substituent.

21. A compound as claimed in claim 17 in which $R^2$ is hydrogen, $R^3$ is hydroxy which is trans- to $R^4$, and $R^4$ is phenyl which may bear a methoxy, hydroxy, methylthio or methylsulfinyl substituent.

22. A compound as claimed in claim 17 in which $R^3$ is hydrogen and $R^2$ and $R^4$ together with a diradical $X^1$ and the piperidino 4-carbon to which they are attached form a spirocyclic ring wherein $R^4$ is phenyl which is joined to $R^2$ by an ortho-substituent diradical $X^1$ in which the phenyl $R^4$ may bear a further substituent selected from methoxy, hydroxy, methylthio, and methylsulfinyl; the diradical $X^1$ is methylene or carbonyl; and $R^2$ is oxy.

23. A compound as claimed in claim 17 in which the substituted piperidino moiety of the compound of formula I is selected from 4-phenylpiperidino, 4-(2-methoxyphenyl)piperidino, 4-(3-methoxyphenyl)piperidino, 4-(4-methoxyphenyl)piperidino, 4-(2-hydroxyphenyl)piperidino, 4-(3-hydroxyphenyl)piperidino, 4-(4-hydroxyphenyl)piperidino, 4-(5-methyl-1,3,4-oxadiazol-2-yl)piperidino, 4-(4-ethoxycarbonylimidazol-2-yl)piperidino, 4-(3-pyridyl)piperidino, 4-(2-pyridyl)piperidino, 4-(2-fluoropyrid-3-yl)piperidino, (3R*,4R*)-3-hydroxy-4-phenylpiperidino, (3S,4S)-3-hydroxy-4-phenylpiperidino, 4-(2-methylthiophenyl)piperidino, 4-(4-methylthiophenyl)piperidino, 4-(2-methylsulfinylphenyl)piperidino, 4-(4-methylsulfinylphenyl)piperidino, 4-(2,4-dihydroxyphenyl)piperidino, 4-(2,5-dimethoxyphenyl)piperidino, 4-(2,5-dihydroxyphenyl)piperidino, spiro[isobenzofuran-1(3H),4'-piperidin]-1'-yl, 3-oxospiro[isobenzofuran-1(3H),4'-piperidin]-1'-yl, and 4-(4-N-methylcarbamoylphenyl)piperidino.

24. A compound of formula I

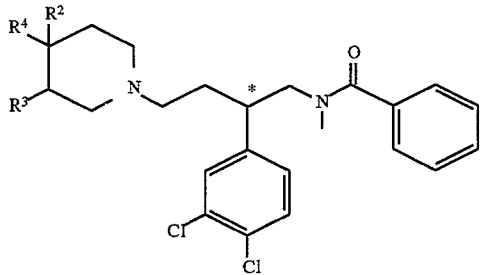

wherein $R^2$ and $R^3$ are each hydrogen and $R^4$ is phenyl which bears a methylthio or methylsulfinyl substituent, or a pharmaceutically acceptable salt thereof.

25. A compound as claimed in claim 24 in which the substituted piperidino moiety of the compound of formula I is selected from 4-(4-methylthiophenyl)piperidino, 4-(2-methylsulfinylphenyl)piperidino, and 4-(4-methylsulfinylphenyl)piperidino.

26. A pharmaceutically acceptable salt as claimed in claim 24 which is a salt made with hydrochloric, sulfuric, phosphoric, methanesulfonic, or para-toluenesulfonic acid.

27. A pharmaceutical composition comprising a pharmaceutically acceptable diluent or carrier and a compound of formula I as claimed in claim 24.

28. A method for the treatment of a disease in which Neurokinin A is implicated and antagonism of its action is desired comprising administering to a human or other mammal in need thereof an effective amount of a compound of formula I as claimed in claim 24.

29. A method as claimed in claim 28 wherein the method is for the treatment of asthma or a related disorder.

30. A compound of formula I

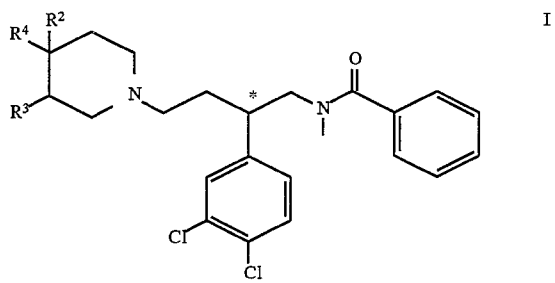

wherein $R^2$ and $R^3$ are each hydrogen and $R^4$ is pyridyl, or a pharmaceutically acceptable salt thereof.

31. A compound as claimed in claim 30 in which $R^4$ is 3-pyridyl.

32. A pharmaceutically acceptable salt as claimed in claim 30 which is a salt made with hydrochloric, sulfuric, phosphoric, methanesulfonic, or para-toluenesulfonic acid.

33. A pharmaceutical composition comprising a pharmaceutically acceptable diluent or carrier and a compound of formula I as claimed in claim 30.

34. A method for the treatment of a disease in which Neurokinin A is implicated and antagonism of its action is desired comprising administering to a human or other mammal in need thereof an effective amount of a compound of formula I as claimed in claim 30.

35. A method as claimed in claim 34 wherein the method is for the treatment of asthma or a related disorder.

36. A compound of formula II, or an acid addition salt thereof,

wherein $R^2$ and $R^3$ are each hydrogen and $R^4$ is selected from 2-methylsulfinylphenyl, 4-methylthiophenyl, 4-methylsulfinylphenyl, and 3-pyridyl.

* * * * *

SEQUENCE LISTING
( 1 ) GENERAL INFORMATION:
( i i i ) NUMBER OF SEQUENCES: 2
( 2 ) INFORMATION FOR SEQ ID NO:1:

```
( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1:

GCGCAAGCTT ATGGG                                                    15

( 2 ) INFORMATION FOR SEQ ID NO:2:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2:

GTCCCATAA GCTTGCGC                                                  18
```